(12) United States Patent
Sack et al.

(10) Patent No.: US 9,572,615 B2
(45) Date of Patent: Feb. 21, 2017

(54) DETACHABLE FRONT DELIVERY ASSEMBLY FOR A TISSUE REPAIR SYSTEM

(75) Inventors: James A. Sack, Elverson, PA (US); Jack Y. Yeh, North Potomac, MD (US)

(73) Assignee: JMEA Corporation, Rockville, MD (US)

( * ) Notice: Subject to any disclaimer, the term of this patent is extended or adjusted under 35 U.S.C. 154(b) by 1160 days.

(21) Appl. No.: 13/552,098

(22) Filed: Jul. 18, 2012

(65) Prior Publication Data

US 2014/0025107 A1    Jan. 23, 2014

(51) Int. Cl.
*A61B 17/88* (2006.01)
*A61B 17/04* (2006.01)
(Continued)

(52) U.S. Cl.
CPC ....... *A61B 17/8875* (2013.01); *A61B 17/0401* (2013.01); *A61B 17/0466* (2013.01); *A61B 17/068* (2013.01); *A61B 17/0642* (2013.01); *A61B 17/844* (2013.01); *A61B 17/86* (2013.01); *A61B 17/8625* (2013.01); *A61B 2017/0046* (2013.01); *A61B 2017/00367* (2013.01); *A61B 2017/00464* (2013.01); *A61B 2017/00473* (2013.01); *A61B 2017/00535* (2013.01); *A61B 2017/00734* (2013.01); *A61B 2017/042* (2013.01); *A61B 2017/044* (2013.01); *A61B 2017/0409* (2013.01); *A61B 2017/0412* (2013.01); *A61B 2017/0414* (2013.01);
(Continued)

(58) Field of Classification Search
CPC .............. A61B 17/0401; A61B 17/844; A61B 17/8625; A61B 17/8875; A61B 17/86;A61B 17/32053; A61B 5/15146; A61B 5/150977; A61B 2017/044; A61B 17/0409; A61B 17/0419
See application file for complete search history.

(56) References Cited

U.S. PATENT DOCUMENTS

| 472,913 A | 4/1892 | Taylor |
| 1,808,318 A | 6/1931 | Pleister |
(Continued)

FOREIGN PATENT DOCUMENTS

| EP | 0507605 A1 | 10/1992 |
| EP | 0589306 A2 | 3/1994 |
(Continued)

OTHER PUBLICATIONS

Office Action mailed May 5, 2014 in U.S. Appl. No. 13/552,130.
(Continued)

*Primary Examiner* — Julian W Woo
*Assistant Examiner* — Lucas Paez
(74) *Attorney, Agent, or Firm* — Plumsea Law Group, LLC

(57) ABSTRACT

A deployment device for a tissue repair system includes a front delivery assembly that is detachable from a base assembly of the deployment device. The front delivery assembly includes at least one prosthesis and at least one driven assembly that actuates the at least one prosthesis. The base assembly includes a driving assembly that may engage the at least one driven assembly of the at least one prosthesis. The front delivery assembly can be rotated so that the position of a prosthesis in the front delivery assembly is moved in and out of alignment with the driving assembly. A kit of parts may be provided that includes a base assembly as well as two or more detachable front delivery assemblies.

28 Claims, 62 Drawing Sheets

(51) Int. Cl.
*A61B 17/064* (2006.01)
*A61B 17/068* (2006.01)
*A61B 17/84* (2006.01)
*A61B 17/86* (2006.01)
*A61B 17/00* (2006.01)

(52) U.S. Cl.
CPC ......... *A61B 2017/0424* (2013.01); *A61B 2017/0427* (2013.01); *A61B 2017/0438* (2013.01); *A61B 2017/0646* (2013.01); *A61B 2090/037* (2016.02)

(56) References Cited

U.S. PATENT DOCUMENTS

| | | |
|---|---|---|
| 2,108,842 A | 2/1938 | Bazzoni |
| 2,222,125 A | 11/1940 | Stehlik |
| 2,680,246 A | 6/1954 | Rambo |
| 2,765,463 A | 10/1956 | De Anguera |
| 3,172,329 A | 3/1965 | Setzler |
| 3,566,739 A | 3/1971 | Lebar |
| 3,765,295 A | 10/1973 | Ptak |
| 3,906,832 A | 9/1975 | Lunn et al. |
| 3,918,130 A | 11/1975 | Poe |
| 3,974,735 A | 8/1976 | Berner |
| 4,013,071 A | 3/1977 | Rosenberg |
| 4,073,212 A | 2/1978 | Lerich |
| 4,085,651 A | 4/1978 | Koscik |
| 4,112,814 A | 9/1978 | Schafers |
| 4,203,446 A | 5/1980 | Hofert et al. |
| 4,223,674 A | 9/1980 | Fluent et al. |
| 4,312,614 A | 1/1982 | Palmer et al. |
| 4,488,843 A | 12/1984 | Achille |
| 4,577,400 A | 3/1986 | Morgan |
| 4,738,255 A | 4/1988 | Goble et al. |
| 4,790,304 A | 12/1988 | Rosenberg |
| 5,028,187 A | 7/1991 | Sato |
| 5,042,888 A | 8/1991 | Shinjo |
| 5,258,010 A | 11/1993 | Green et al. |
| 5,332,346 A | 7/1994 | Shinjo |
| 5,441,502 A | 8/1995 | Bartlett |
| 5,464,427 A | 11/1995 | Curtis et al. |
| 5,480,403 A | 1/1996 | Lee et al. |
| 5,486,197 A | 1/1996 | Le et al. |
| 5,501,695 A | 3/1996 | Anspach, Jr. et al. |
| 5,582,615 A | 12/1996 | Foshee et al. |
| 5,618,314 A | 4/1997 | Harwin et al. |
| 5,628,579 A | 5/1997 | Forster |
| 5,643,321 A | 7/1997 | McDevitt |
| 5,645,589 A | 7/1997 | Li |
| 5,649,963 A | 7/1997 | McDevitt |
| 5,662,658 A | 9/1997 | Wenstrom, Jr. |
| 5,690,455 A | 11/1997 | Fischer et al. |
| 5,690,639 A | 11/1997 | Lederer et al. |
| 5,704,746 A | 1/1998 | Leib et al. |
| 5,713,903 A | 2/1998 | Sander et al. |
| 5,720,753 A | 2/1998 | Sander et al. |
| 5,725,541 A | 3/1998 | Anspach, III et al. |
| 5,741,268 A | 4/1998 | Schutz |
| 5,741,282 A | 4/1998 | Anspach, III et al. |
| 5,741,300 A | 4/1998 | Li |
| 5,797,963 A | 8/1998 | McDevitt |
| 5,814,071 A | 9/1998 | McDevitt et al. |
| 5,830,231 A | 11/1998 | Geiges, Jr. |
| 5,860,983 A | 1/1999 | Wenstrom, Jr. |
| 5,881,942 A | 3/1999 | Bergamini |
| 5,893,850 A | 4/1999 | Cachia |
| 5,904,284 A | 5/1999 | Lin |
| 5,928,244 A | 7/1999 | Tovey et al. |
| RE36,289 E | 8/1999 | Le et al. |
| 5,944,739 A | 8/1999 | Zlock et al. |
| 5,957,953 A | 9/1999 | DiPoto et al. |
| 5,980,558 A | 11/1999 | Wiley |
| 6,010,513 A | 1/2000 | Tormala et al. |
| 6,022,373 A | 2/2000 | Li |
| 6,074,395 A | 6/2000 | Trott et al. |
| 6,129,762 A | 10/2000 | Li |
| 6,146,387 A | 11/2000 | Trott et al. |
| 6,187,008 B1 | 2/2001 | Hamman |
| 6,273,893 B1 | 8/2001 | McAllen, III et al. |
| 6,280,448 B1 | 8/2001 | Trott et al. |
| 6,319,252 B1 | 11/2001 | McDevitt et al. |
| 6,319,269 B1 | 11/2001 | Li |
| 6,319,271 B1 | 11/2001 | Schwartz et al. |
| 6,328,746 B1 | 12/2001 | Gambale |
| 6,328,758 B1 | 12/2001 | Tornier et al. |
| 6,348,053 B1 | 2/2002 | Cachia |
| 6,387,113 B1 | 5/2002 | Hawkins et al. |
| 6,402,759 B1 | 6/2002 | Strong et al. |
| 6,425,900 B1 | 7/2002 | Knodel et al. |
| 6,457,625 B1 | 10/2002 | Tormala et al. |
| 6,530,933 B1 | 3/2003 | Yeung et al. |
| 6,540,770 B1 | 4/2003 | Tornier et al. |
| 6,544,281 B2 | 4/2003 | ElAttrache et al. |
| 6,575,976 B2 | 6/2003 | Grafton |
| 6,599,295 B1 | 7/2003 | Tornier et al. |
| 6,623,492 B1 | 9/2003 | Berube et al. |
| 6,641,596 B1 | 11/2003 | Lizardi |
| 6,648,890 B2 | 11/2003 | Culbert et al. |
| 6,652,561 B1 | 11/2003 | Tran |
| 6,656,183 B2 | 12/2003 | Colleran et al. |
| 6,673,094 B1 | 1/2004 | McDevitt et al. |
| 6,685,706 B2 | 2/2004 | Padget et al. |
| 6,733,506 B1 | 5/2004 | McDevitt et al. |
| 6,769,849 B2 | 8/2004 | Yoneoka |
| 6,770,073 B2 | 8/2004 | McDevitt et al. |
| 6,779,701 B2 | 8/2004 | Bailly et al. |
| 6,846,313 B1 | 1/2005 | Rogers et al. |
| 6,942,666 B2 | 9/2005 | Overaker et al. |
| 6,942,668 B2 | 9/2005 | Padget et al. |
| 6,986,781 B2 | 1/2006 | Smith |
| 7,008,428 B2 | 3/2006 | Cachia et al. |
| 7,033,380 B2 | 4/2006 | Schwartz et al. |
| 7,037,324 B2 | 5/2006 | Martinek |
| 7,144,415 B2 | 12/2006 | Del Rio et al. |
| 7,309,337 B2 | 12/2007 | Colleran et al. |
| 7,381,213 B2 | 6/2008 | Lizardi |
| 7,438,718 B2 | 10/2008 | Milliman et al. |
| 7,547,326 B2 | 6/2009 | Bhatnagar et al. |
| 7,559,449 B2 | 7/2009 | Viola |
| 7,572,283 B1 | 8/2009 | Meridew |
| 7,597,230 B2 | 10/2009 | Racenet et al. |
| 7,608,108 B2 | 10/2009 | Bhatnagar et al. |
| 7,621,927 B2 | 11/2009 | Messerly et al. |
| 7,632,284 B2 | 12/2009 | Martinek et al. |
| 7,632,313 B2 | 12/2009 | Bhatnagar et al. |
| 7,637,926 B2 | 12/2009 | Foerster et al. |
| 7,648,524 B2 | 1/2010 | Zhang et al. |
| 7,713,285 B1 | 5/2010 | Stone et al. |
| 7,717,921 B2 | 5/2010 | Rezach |
| 7,780,701 B1 | 8/2010 | Meridew et al. |
| 7,794,484 B2 | 9/2010 | Stone et al. |
| 7,846,181 B2 | 12/2010 | Schwartz et al. |
| 7,862,272 B2 | 1/2011 | Nakajima |
| 7,867,251 B2 | 1/2011 | Colleran et al. |
| 7,867,264 B2 | 1/2011 | McDevitt et al. |
| 7,896,907 B2 | 3/2011 | McDevitt et al. |
| 7,976,565 B2 | 7/2011 | Meridew |
| 8,070,818 B2 | 12/2011 | Bhatnagar et al. |
| 8,177,847 B2 | 5/2012 | Bhatnagar et al. |
| 8,211,126 B2 | 7/2012 | Yeh et al. |
| 8,403,944 B2 | 3/2013 | Pain et al. |
| 8,627,553 B2 | 1/2014 | Kuhm et al. |
| 9,089,379 B2 | 7/2015 | Sack et al. |
| 2001/0010008 A1 | 7/2001 | Gellman et al. |
| 2001/0049489 A1 | 12/2001 | Kenison et al. |
| 2002/0121539 A1 | 9/2002 | Strong et al. |
| 2002/0156500 A1 | 10/2002 | Storz-Irion et al. |
| 2003/0109900 A1 | 6/2003 | Martinek |
| 2003/0129040 A1 | 7/2003 | Arisaka |
| 2003/0158604 A1 | 8/2003 | Cauthen, III et al. |
| 2005/0143734 A1 | 6/2005 | Cachia et al. |
| 2005/0149122 A1 | 7/2005 | McDevitt et al. |
| 2005/0220561 A1 | 10/2005 | Okada |
| 2006/0235413 A1 | 10/2006 | Denham et al. |

(56) References Cited

U.S. PATENT DOCUMENTS

| | | |
|---|---|---|
| 2006/0247643 A1 | 11/2006 | Bhatnagar et al. |
| 2006/0247644 A1 | 11/2006 | Bhatnagar et al. |
| 2007/0032793 A1 | 2/2007 | Del Rio et al. |
| 2008/0033486 A1 | 2/2008 | Whittaker et al. |
| 2008/0281325 A1 | 11/2008 | Stone et al. |
| 2008/0288003 A1 | 11/2008 | McKinley |
| 2009/0005792 A1 | 1/2009 | Miyamoto et al. |
| 2009/0105798 A1 | 4/2009 | Koch |
| 2009/0118734 A1 | 5/2009 | Bhatnagar et al. |
| 2009/0299386 A1 | 12/2009 | Meridew |
| 2009/0318964 A1 | 12/2009 | Lombardo et al. |
| 2010/0016869 A1 | 1/2010 | Paulk et al. |
| 2010/0016902 A1 | 1/2010 | Paulk et al. |
| 2010/0049215 A1 | 2/2010 | Kayan et al. |
| 2010/0100135 A1 | 4/2010 | Phan |
| 2010/0121355 A1 | 5/2010 | Gittings et al. |
| 2010/0152773 A1 | 6/2010 | Lunn et al. |
| 2010/0198258 A1 | 8/2010 | Heaven et al. |
| 2010/0292712 A1 | 11/2010 | Nering et al. |
| 2010/0292713 A1 | 11/2010 | Cohn et al. |
| 2010/0331881 A1 | 12/2010 | Hart |
| 2011/0004258 A1 | 1/2011 | Stone et al. |
| 2011/0046682 A1 | 2/2011 | Stephan et al. |
| 2011/0082476 A1 | 4/2011 | Furnish et al. |
| 2011/0106013 A1 | 5/2011 | Whittaker et al. |
| 2011/0112550 A1 | 5/2011 | Heaven et al. |
| 2011/0152885 A1 | 6/2011 | McDevitt et al. |
| 2011/0264227 A1 | 10/2011 | Boyajian et al. |
| 2012/0016373 A1 | 1/2012 | Impellizzeri |
| 2012/0022586 A1 | 1/2012 | Whitman et al. |
| 2012/0109132 A1 | 5/2012 | Ellis et al. |
| 2012/0172885 A1 | 7/2012 | Drapeau et al. |
| 2013/0138152 A1 | 5/2013 | Stone et al. |
| 2013/0296640 A1 | 11/2013 | Goldman et al. |
| 2014/0025125 A1 | 1/2014 | Sack et al. |
| 2014/0046369 A1 | 2/2014 | Heaven et al. |

FOREIGN PATENT DOCUMENTS

| | | |
|---|---|---|
| EP | 0990450 A2 | 4/2000 |
| WO | 9627332 A1 | 9/1996 |
| WO | 9831288 A1 | 7/1998 |

OTHER PUBLICATIONS

Interview Summary mailed Mar. 2, 2015 in U.S. Appl. No. 13/552,181.
Notice of Allowance mailed Mar. 23, 2015 in U.S. Appl. No. 13/552,181.
Interview Summary mailed Jul. 9, 2015 in U.S. Appl. No. 13/552,072.
Amendment filed Jul. 13, 2015 in U.S. Appl. No. 13/552,072.
Notice of Allowance mailed Jul. 28, 2015 in U.S. Appl. No. 13/552,072.
Office Action mailed Jul. 29, 2015 in U.S. Appl. No. 13/552,163.
Interview Summary mailed Sep. 22, 2014 in U.S. Appl. No. 13/552,130.
Amendment After Final Rejection filed May 11, 2015 in U.S. Appl. No. 13/552,130.
Final Office Action mailed Jan. 9, 2015 in U.S. Appl. No. 13/552,130.
Amendment filed Oct. 6, 2014 in U.S. Appl. No. 13/552,130.
Office Action mailed Oct. 1, 2014 in U.S. Appl. No. 13/552,181.
International Search Report and Written Opinion dated Nov. 13, 2013 in International Application No. PCT/US2013/050441.
Dr. Stephen J. Snyder, "The Rotator Cuff Repair System Surgical Technique," Linvatec Corporation, Largo, Florida 34643, 1993.
Office Action mailed Feb. 11, 2015 in U.S. Appl. No. 13/552,072.
Amendment filed Mar. 2, 2015 in U.S. Appl. No. 13/552,181.
Response to Official Communication under Rule 161, filed Nov. 24, 2015 in European Patent Application No. 13 820 667.7.
Office Action mailed Oct. 2, 2015 in U.S. Appl. No. 13/552,130.
Amendment filed Feb. 2, 2016 in U.S. Appl. No. 13/552,130.
Amendment filed Dec. 22, 2015 in U.S. Appl. No. 13/552,163.
Extended European Search Report dated Apr. 29, 2016 in European Patent Application No. 13820667.7.
Final Office Action mailed Mar. 11, 2016 in U.S. Appl. No. 13/552,130.
Interview Summary mailed May 11, 2016 in U.S. Appl. No. 13/552,130.
Notice of Allowance mailed May 6, 2016 in U.S. Appl. No. 13/552,163.

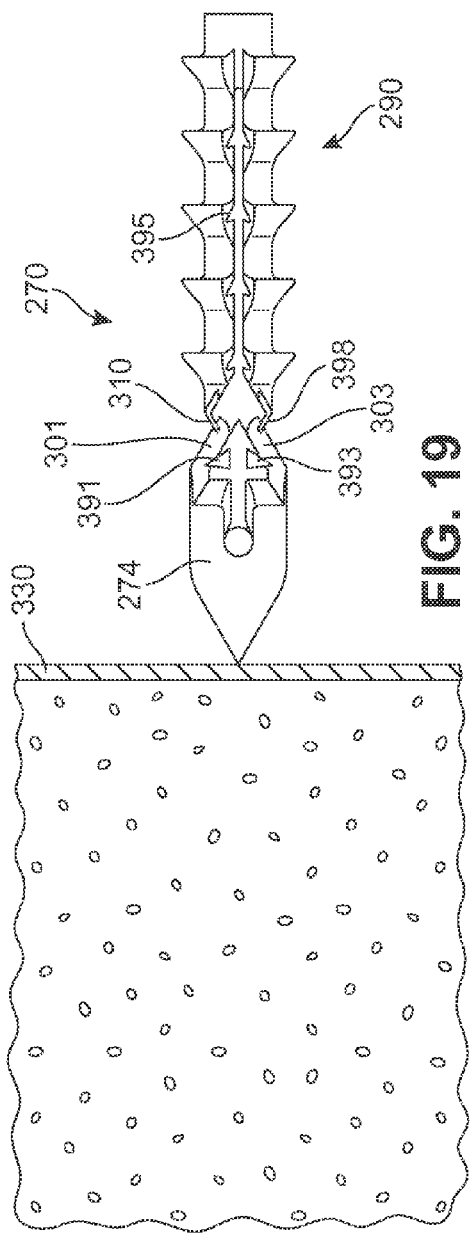
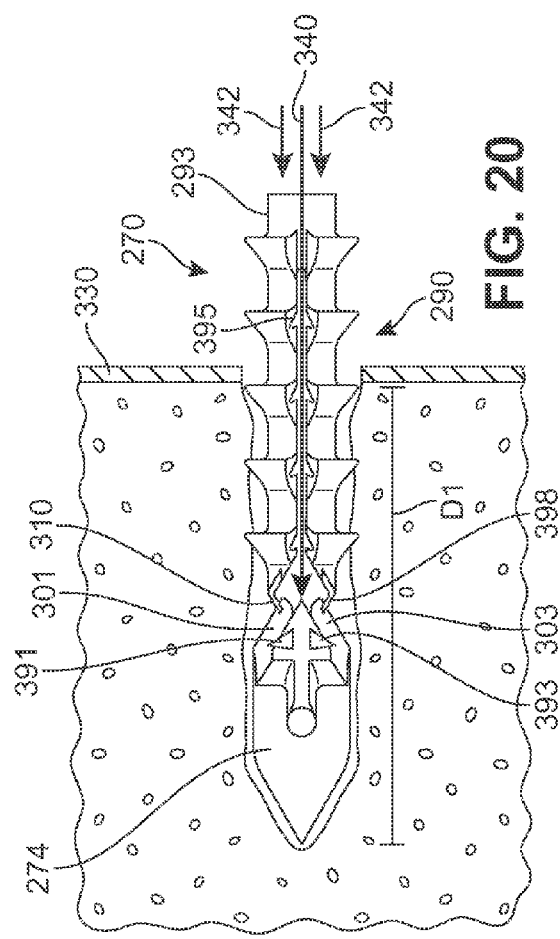

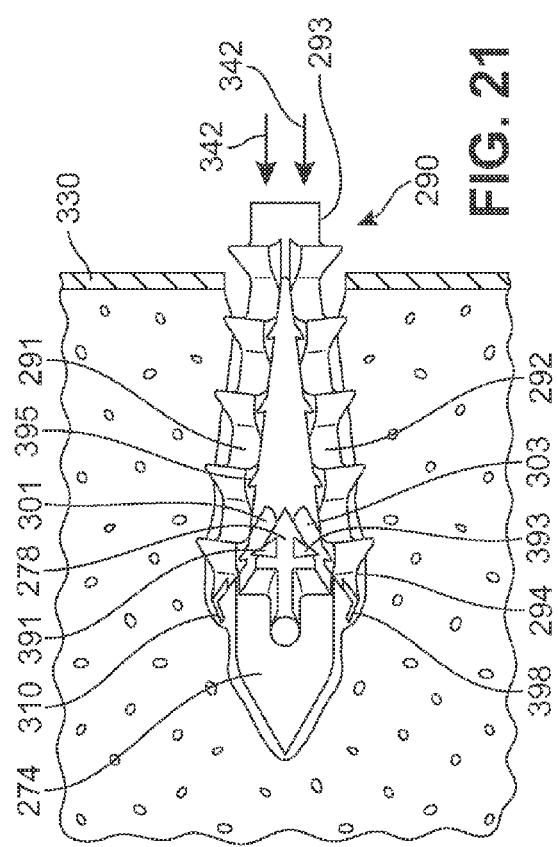
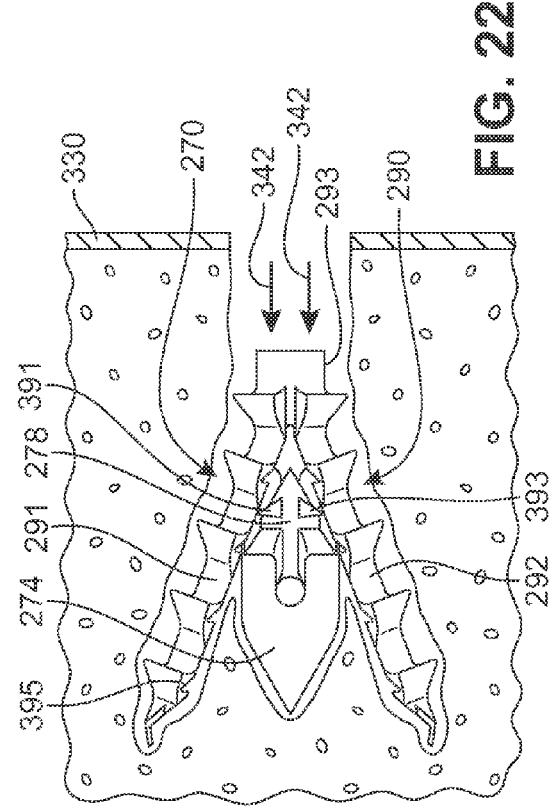

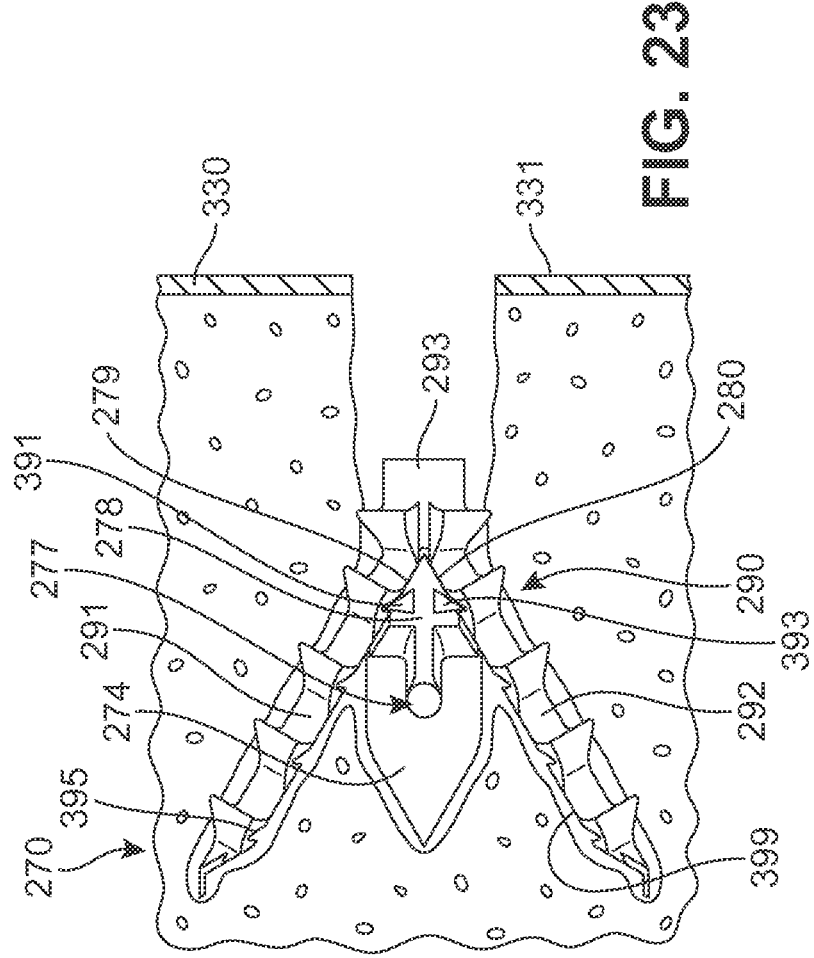

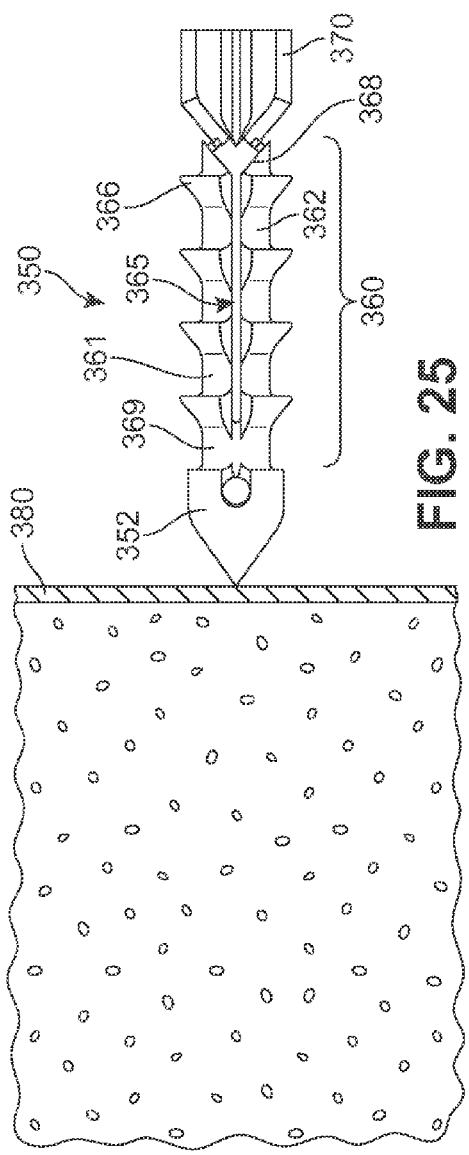
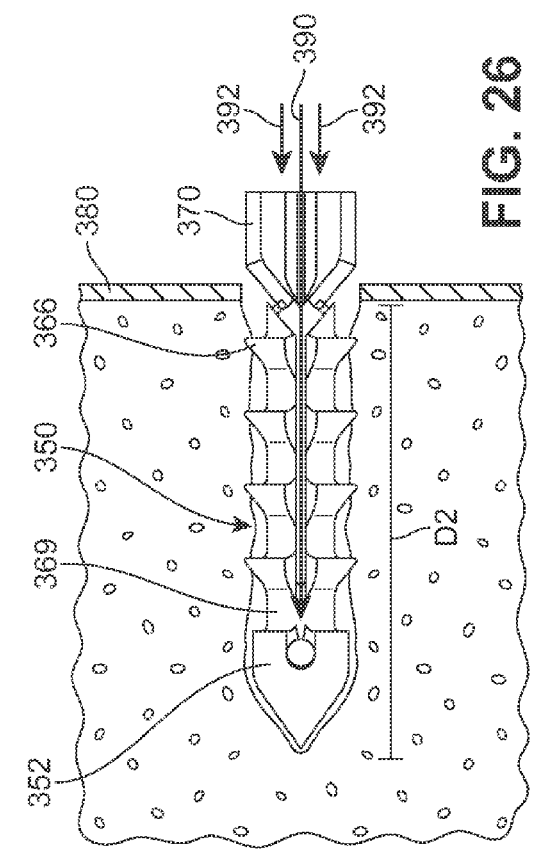

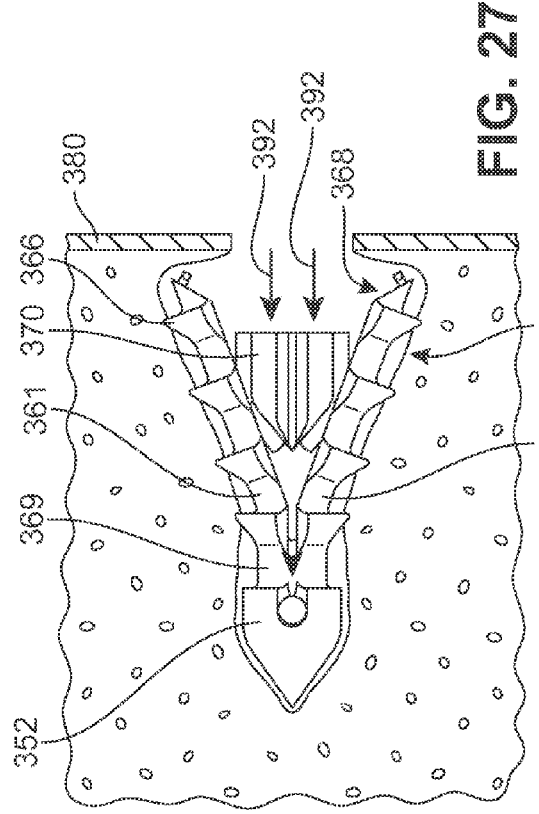
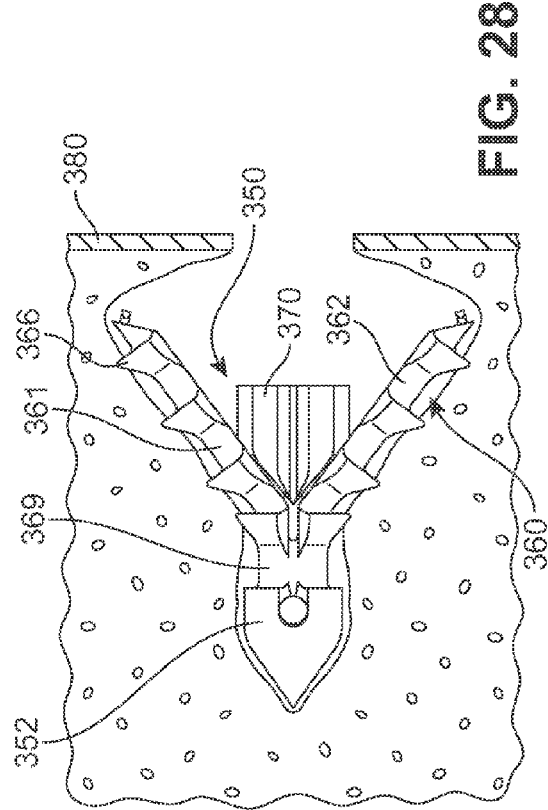

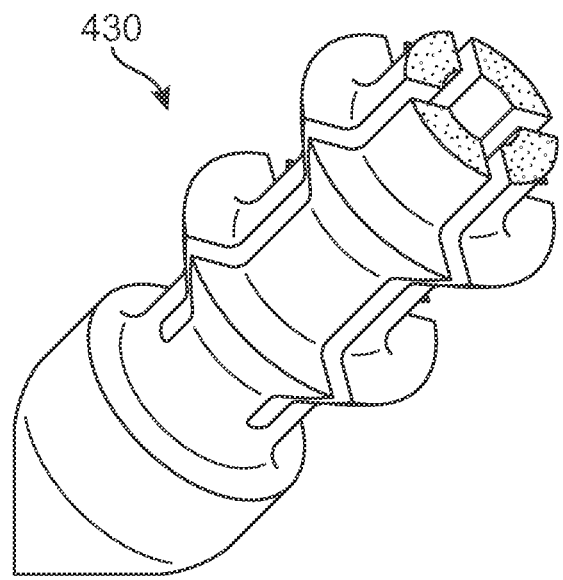
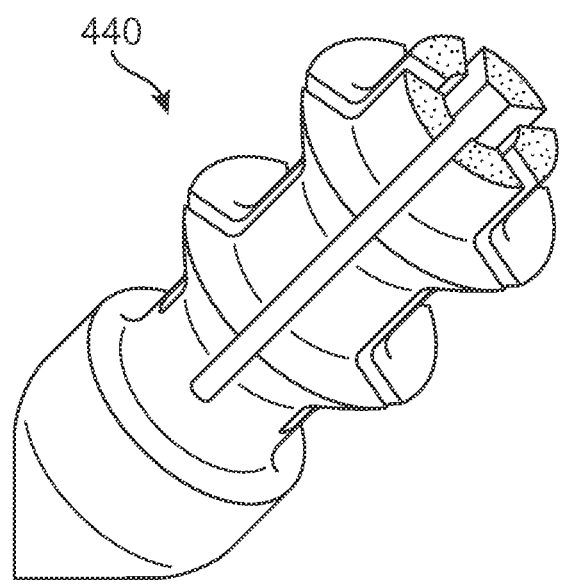
FIG. 31

DETACHABLE FRONT DELIVERY ASSEMBLY FOR A TISSUE REPAIR SYSTEM

RELATED APPLICATIONS

This application is related to the following commonly owned applications: U.S. Patent Publication Number US2014/0025082, published Jan. 23, 2014 (U.S. patent application Ser. No. 13/552,072, filed Jul. 18, 2012), titled "Impact And Drive System For Prosthesis Deployment Device"; U.S. Patent Publication Number US2014/0025125, published Jan. 23, 2014 (U.S. patent application Ser. No. 13/552,130, filed Jul. 18, 2012), titled "Expandable Prosthesis For A Tissue Repair System"; U.S. Patent Publication Number US2014/0025108, published Jan. 23, 2014 (U.S. patent application Ser. No. 13/552,163, filed Jul. 18, 2012), titled "Method And System For Implanting Multiple Prostheses"; and U.S. Patent Publication Number US2014/0025109, published Jan. 23, 2014 (U.S. patent application Ser. No. 13/552,181, filed Jul. 18, 2012), titled "Multi-Impact System For Prosthesis Deployment Device", which are all herein incorporated by reference.

BACKGROUND

The present embodiments relate generally to systems and methods for repairing tissue.

Sutures are often used to repair various imperfections in tissue. For example, flaws, holes, tears, bulges, a deliberate cut or incision may all be repaired using sutures. In the case of a rotator cuff tendon tear, sutures may be used to help re-attach the torn or receded portion of the rotator cuff tendon to the humerus bone. Sutures are also used to repair glenoid labrum tears and superior labrum anterior and posterior (SLAP) tears.

SUMMARY

In one aspect, a deployment device for a prosthesis includes a driven assembly configured to apply a force to the prosthesis. The driven assembly includes a driven tube including a hollow longitudinal cavity and the driven assembly also includes a driven pin. The deployment device also includes a driving assembly configured to drive the driven pin and the driven tube. The driven pin can move through the hollow longitudinal cavity of the driven tube.

In another aspect, a deployment device for a prosthesis includes a driven assembly configured to apply a force to the prosthesis. The driven assembly includes a driven tube including a hollow longitudinal cavity and the driven assembly also includes a driven pin. The driven pin is configured to move through the hollow longitudinal cavity of the driven tube. The driven tube is configured to move a first distance and the driven pin is configured to move a second distance. The first distance is substantially greater than the second distance.

In another aspect, a deployment device for a prosthesis includes a driving assembly comprising a driving pin and a driving tube. The driving tube includes a first hollow longitudinal cavity, where the driving pin can move through the first hollow longitudinal cavity. The deployment device also includes a driven assembly to apply a force to the prosthesis, where the driven assembly also includes a driven tube including a second hollow longitudinal cavity and where the driven assembly also includes a driven pin. The driven pin is configured to move through the second hollow longitudinal cavity of the driven tube and the driving tube, the driving pin, the driven tube, and the driven pin are all aligned along a longitudinal axis.

In another aspect, a kit of parts for tissue repair includes a first front delivery assembly including at least one prosthesis configured for implantation and a second front delivery assembly including at least one prosthesis configured for implantation. The kit of parts also includes a base assembly, where the first front delivery assembly can be removably attached to the base assembly and where the second front delivery assembly can be removably attached to the base assembly. The base assembly is configured to provide power assistance for implanting prostheses.

In another aspect, a deployment device for tissue repair includes a first prosthesis and a second prosthesis. The deployment device also includes a driving assembly configured to provide a driving force. The first prosthesis and the second prosthesis can be positioned within the deployment device at a first configuration and a second configuration. The first prosthesis is aligned with the driving assembly in the first configuration and the second prosthesis is out of alignment with the driving assembly in the first configuration. The second prosthesis is aligned with the driving assembly in the second configuration and the first prosthesis is out of alignment with the driving assembly in the second configuration.

In another aspect, a method of operating a deployment device for tissue repair includes attaching a front delivery assembly including at least one prosthesis to a base assembly. The method also includes aligning the front delivery assembly with a desired region of tissue. The method also includes implanting the at least one prosthesis using the deployment device and detaching the front delivery assembly from the base assembly.

In another aspect, a prosthesis configured for implantation into tissue includes a driving portion including a driving tip portion and a wedge portion as well as a base portion including a forward portion and a rearward portion, where the forward portion being associated with the driving portion. The base portion includes a first longitudinal portion that extends along the length of the base portion and a second longitudinal portion that extends along the length of the base portion. The first longitudinal portion and the second longitudinal portion are attached at the rearward portion, and the first longitudinal portion and the second longitudinal portion are separable at the forward portion. The first longitudinal portion is associated with a first surface of the wedge portion, and the second longitudinal portion is associated with a second surface of the wedge portion. The first longitudinal portion and the second longitudinal portion are configured to engage the wedge portion and spread apart from one another during the implantation of the prosthesis.

In another aspect, a prosthesis for tissue repair includes a driving portion including a driving tip portion and a wedge portion and a base portion including a forward portion and a rearward portion, where the forward portion is disposed adjacent to the wedge portion. The base portion is configured to expand when the forward portion is engaged by the wedge portion. The forward portion is connected to the wedge portion prior to implantation into a tissue and the forward portion and the wedge portion are configured to separate during an implantation process.

In another aspect, a prosthesis configured for implantation into tissue includes a driving portion and a base portion including a forward portion and a rearward portion, where the forward portion being associated with the driving portion. The prosthesis also includes a wedge portion associated with the rearward portion of the base portion. The base portion includes a first longitudinal portion that extends along the length of the base portion and a second longitudinal portion that extends along the length of the base portion. The first longitudinal portion and the second longitudinal portion are attached at the forward portion and the first longitudinal portion and the second longitudinal portion are separable at the rearward portion. The first longitudinal portion and the second longitudinal portion are configured to engage the wedge portion and spread apart from one another during the implantation of the prosthesis.

In another aspect, a prosthesis for tissue repair includes a driving portion. The prosthesis also includes a base portion including a forward portion and a rearward portion, where the forward portion is associated with the driving portion. The prosthesis also includes a wedge portion associated with the rearward portion of the base portion. The base portion is configured to expand when the rearward portion is engaged by the wedge portion. The rearward portion is connected to the wedge portion prior to implantation into a tissue and the rearward portion and the wedge portion are configured to separate during an implantation process.

In one aspect, a tissue repair system includes a deployment device configured to house two or more prostheses, where the deployment device provides two prosthesis positions including a driving position and a storage position. The tissue repair system also includes a first prosthesis, a second prosthesis, and at least one connecting member. The deployment device has an initial configuration where the first prosthesis is in the driving position, the second prosthesis is in the storage position, and the at least one connecting member joins the first prosthesis and the second prosthesis. The deployment device is configured to implant the first prosthesis and the second prosthesis in multiple stages. A first stage includes the first prosthesis being implanted from the driving position such that the at least one connecting member extends from the implanted first prosthesis to the second prosthesis in the storage position. A second stage includes the second prosthesis being moved from the storage position to the driving position. And a third stage includes the second prosthesis being implanted from the driving position with the connecting member still joining the first prosthesis and the second prosthesis.

In another aspect, a tissue repair system includes a deployment device configured to house two or more prostheses, where the deployment device provides two prosthesis positions including a driving position and a storage position. The tissue repair system also includes a plurality of prostheses and at least one connecting member. The deployment device has an initial configuration in which one of the plurality of prostheses is in the driving position, one or more other prostheses of the plurality of prostheses is in the storage position, and the connecting member joins together each prosthesis of the plurality of prostheses. The deployment device is configured to implant each prosthesis of the plurality of prostheses in multiple stages. The multiple stages include a stage of implanting the one prosthesis from the driving position. The multiple stages also include a stage of moving at least one of the one or more other prostheses from the storage position to the driving position.

In another aspect, a method of implanting multiple prostheses into a tissue using a deployment device includes aligning an end of the deployment device in a first location, where the deployment device includes an energy storage system that provides power to implant prostheses. The method also includes releasing energy of the energy storage system such that the deployment device implants a first prosthesis in the first location, where the implanted first prosthesis is attached by at least one connecting member to a second prosthesis inside the deployment device. The method also includes adjusting the position of the second prosthesis within the deployment device so that the second prosthesis is configured for implantation. The method also includes aligning the end of the deployment device in a second location that is different from the first location. The method also includes releasing energy of the energy storage system such that the deployment device implants the second prosthesis in the second location, where the first prosthesis and the second prosthesis are joined by the at least one connecting member extending from the first location to the second location.

In one aspect, a deployment device for repairing tissue includes a front delivery assembly including a driven assembly configured to hold a prosthesis, a base assembly including a driving assembly that is configured to impact the driven assembly and a trigger assembly for activating the driving assembly. The deployment device is configured such that the driving assembly is adapted to impact the driven assembly multiple times by engaging the trigger assembly multiple times. Subsequent impacts of the driving assembly with the driven assembly are configured to drive the prosthesis farther into the tissue.

In another aspect, a deployment device includes a front delivery assembly including a driven assembly configured to hold a prosthesis, a base assembly including a driving assembly, and a trigger assembly for activating the driving assembly. The deployment device is operable in an initial state in which the driving assembly is at rest and the driving assembly and the driven assembly are spaced apart by a first distance. The deployment device is also operable in an intermediate state in which the driving assembly is at rest and the driving assembly and the driven assembly are spaced apart by a second distance. The deployment device is also operable in a final state in which the driving assembly is at rest and the driving assembly and the driven assembly are spaced apart by a third distance. The third distance is greater than the second distance and wherein the second distance is greater than the first distance.

In another aspect, a method of implanting a prosthesis into tissue using a deployment device includes actuating a driving assembly so that the driving assembly engages a driven assembly corresponding to the prosthesis, observing a position of a depth indicator that is associated with a depth to which the prosthesis has been implanted within the tissue, and actuating the driving assembly a second time if the position of the depth indicator is spaced apart from a predetermined depth position.

Other systems, methods, features and advantages of the embodiments will be, or will become, apparent to one of ordinary skill in the art upon examination of the following figures and detailed description. It is intended that all such additional systems, methods, features and advantages be included within this description and this summary, be within the scope of the embodiments, and be protected by the following claims.

BRIEF DESCRIPTION OF THE DRAWINGS

The embodiments can be better understood with reference to the following drawings and description. The components in the figures are not necessarily to scale, emphasis instead being placed upon illustrating the principles of the embodiments. Moreover, in the figures, like reference numerals designate corresponding parts throughout the different views.

FIG. 19 a schematic diagram illustrating a schematic view of a prosthesis being aligned with a tissue according to one embodiment;

FIG. 20 is a schematic diagram illustrating another schematic view of the prosthesis of FIG. 19, in which the prosthesis has been driven into the tissue;

FIG. 21 is a schematic diagram illustrating another schematic view of the prosthesis of FIG. 19, in which a base portion of the prosthesis has started to expand;

FIG. 22 is a schematic diagram illustrating another schematic view of the prosthesis of FIG. 21, in which the base portion continues to expand;

FIG. 23 is a schematic diagram illustrating another schematic view of the prosthesis of FIG. 22, in which the base portion is fully expanded;

FIG. 25 is a schematic diagram illustrating a schematic view of a prosthesis being aligned with a tissue according to one embodiment;

FIG. 26 is a schematic diagram illustrating another schematic view of the prosthesis of FIG. 25, in which the prosthesis has been driven into the tissue;

FIG. 27 is a schematic diagram illustrating another schematic view of the prosthesis of FIG. 26, in which a base portion of the prosthesis has started to expand;

FIG. 28 is a schematic diagram illustrating another schematic view of the prosthesis of FIG. 26, in which the base portion continues to expand;

FIG. 31 is a schematic diagram of two different configurations for a prosthesis according to various embodiments;

DETAILED DESCRIPTION

Figure 1:
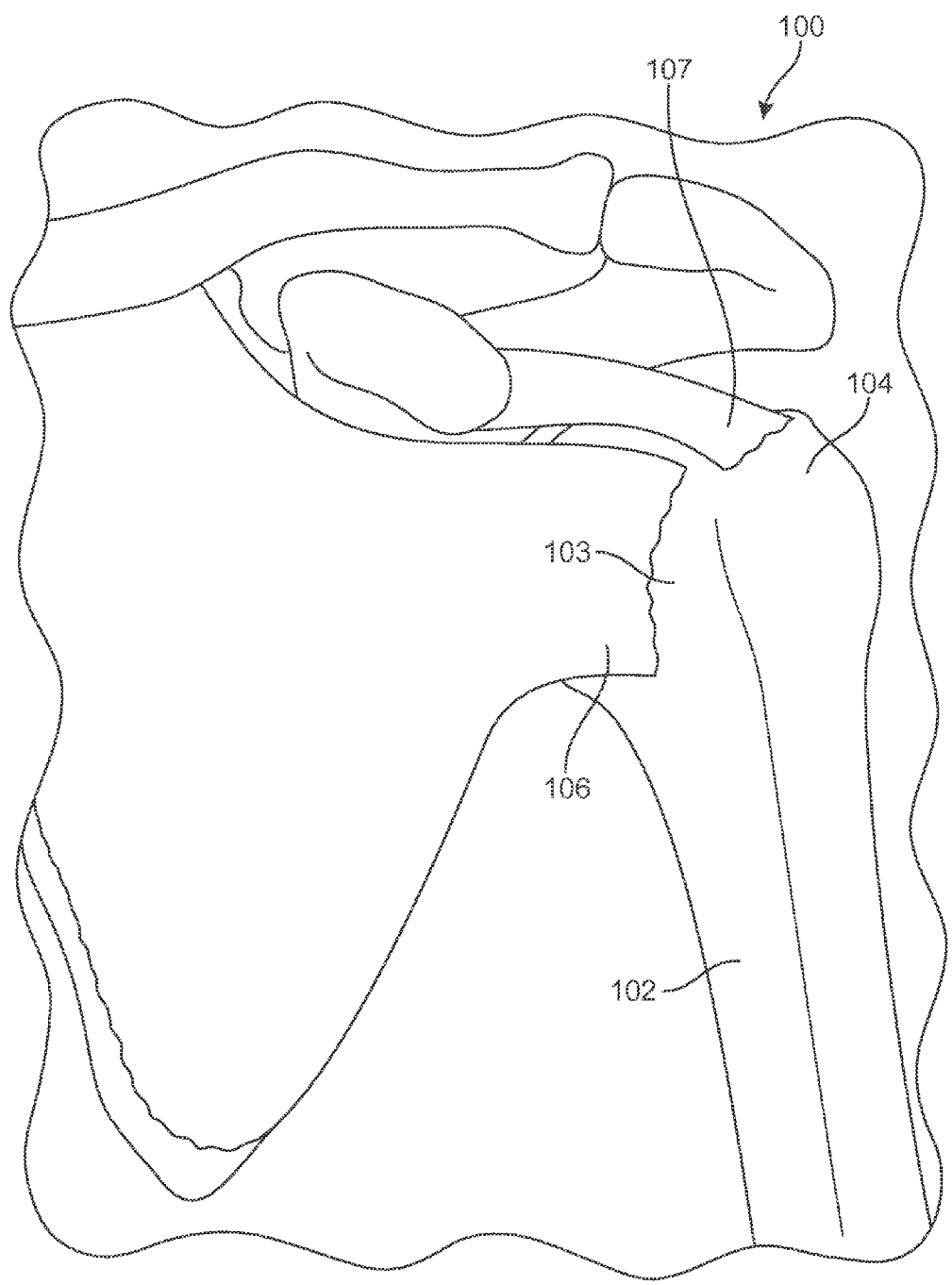
FIG. 1 is a schematic diagram of an example of a shoulder joint including the attachment of rotator cuff tendons to the greater tuberosity of the humerus.

FIG. 1 illustrates a schematic view of an embodiment of some elements of shoulder joint 100. More generally, shoulder joint 100 may comprise a ball and socket joint formed by the humerus and scapula bones. Shoulder joint 100 may generally comprise various muscles and tendons that help with stabilization of the joint. For example, shoulder joint 100 may include four muscles including the supraspinatus muscle, the infraspinatus muscle, the teres minor muscle and the subscapularis muscle. These muscles may be attached to the greater tuberosity 104 and lesser tuberosity 103 of humerus 102 by various groups of tendons. The fusion of the tendons associated with each of the muscle groups forms the rotator cuff. As one example, subscapularis tendon 106, also referred to simply as tendon 106, provides attachment of the subscapularis muscles to lesser tuberosity 103 of humerus 102. Additionally, the current embodiment also clearly illustrates supraspinatus tendon 107, which attaches the supraspinatus muscles to greater tuberosity 104 of humerus 102.

Figure 2:
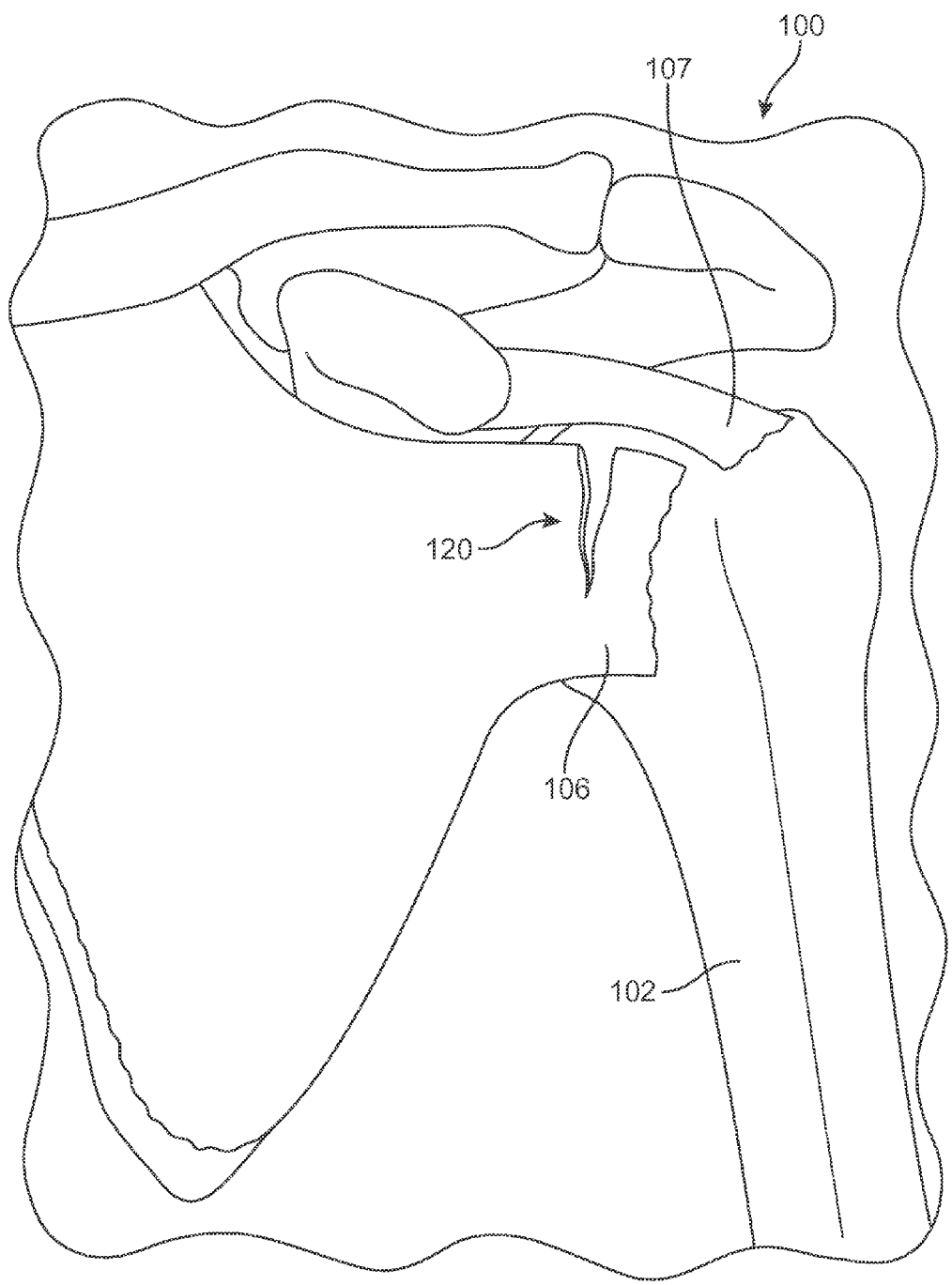
FIG. 2 is a schematic diagram of an example of a shoulder joint in which a rotator cuff tendon has partially torn.

At times, a tendon of the rotator cuff, such as tendon 106 may be ruptured or torn, a condition commonly referred to as a "torn rotator cuff." Rotator cuff tears may be classified as partial thickness tears or full thickness tears, as well as by whether the tendon has completely detached from the greater tuberosity 104 or lesser tuberosity 103 of humerus 102. By way of example, FIG. 2 illustrates a schematic view of an embodiment of shoulder joint 100 in which tendon 106 has been torn. In particular, tear 120 is a partial tear that occurs adjacent to the region where tendon 106 attaches to humerus 102.

Although FIG. 2 illustrates one possible location for a rotator cuff tear, it will be understood that tears can occur at any location along tendon 106. Other examples of tears include glenoid labrum tears and SLAP (superior labrum anterior and posterior) tears. It will be understood that this is not intended to be an exhaustive list of possible tears. The method and system discussed below for repairing tears is not limited to tears of the kind illustrated in FIG. 2. Instead, FIG. 2 is meant to illustrate one possible example of a tear for purposes of clarifying the general method and system for repair disclosed throughout the remainder of this detailed description. As discussed in further detail below, the method and system discussed in these embodiments may be utilized for repairing a wide variety of tears or other imperfections in various different kinds of tissues.

Figure 3:
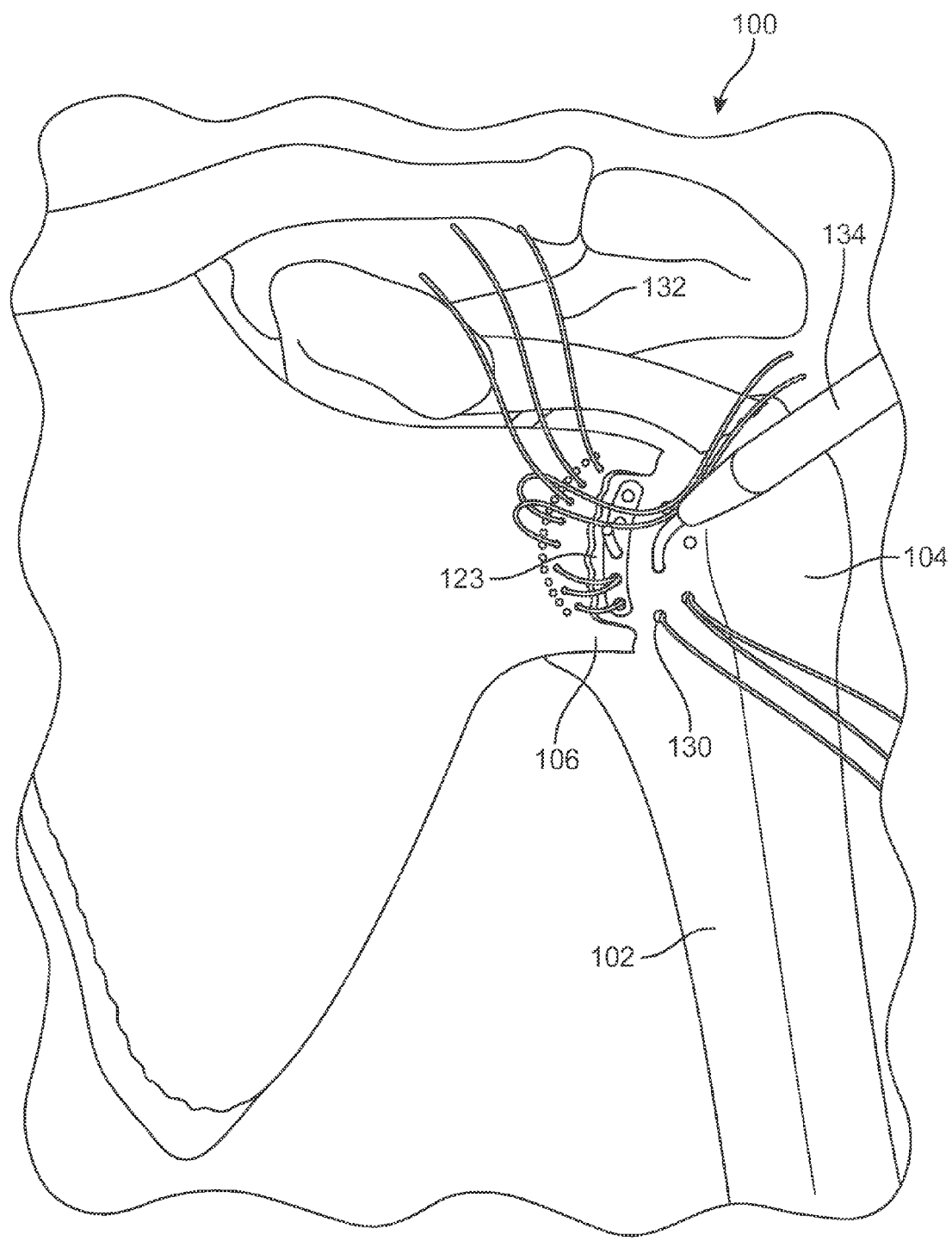
FIG. 3 is a schematic diagram of a conventional method of repairing a torn rotator cuff tendon.

FIG. 3 is intended to illustrate a schematic view of one possible method of repairing a rotator cuff tear 123, in which an end portion of tendon 106 has been fully detached from humerus 102. The method illustrated in FIG. 3 for repairing rotator cuff tears may be complex and may require many steps that could be difficult to perform by surgeons. In some cases, one step of the repair surgery involves passing sutures 132 through tendon 106 to form a predetermined stitch. These stitches can be complicated to ensure the end of the tendon is properly anchored. In another step, the surgeon may form bone tunnels 130 in humerus 102, typically through the use of a cortical gauge punch or similar tool (not shown). As many bone tunnels are necessary, the cortical gauge punch may be used many times in succession. With the stitches made in tendon 106 and bone tunnels 130 formed in humerus 102, sutures 132 must then be threaded through bone tunnels 130. This may be achieved using a plunger 134 or similar tool. Finally, once all sutures 132 have been passed through bone tunnels 130, the ends of sutures 132 must be matched with corresponding ends and tied together with knots (not shown). This process may be time consuming and laborious due to the large number of steps. Moreover, the complexity of the process may limit the number of surgeons able to perform the operation. Other methods for repairing a tear in a tendon may use anchors. These other methods may also require sutures to be tied together during surgery (following implantation of anchors into the bone), which can be a time consuming and laborious process.

System and Method for Implanting Multiple Prostheses

Figure 4:
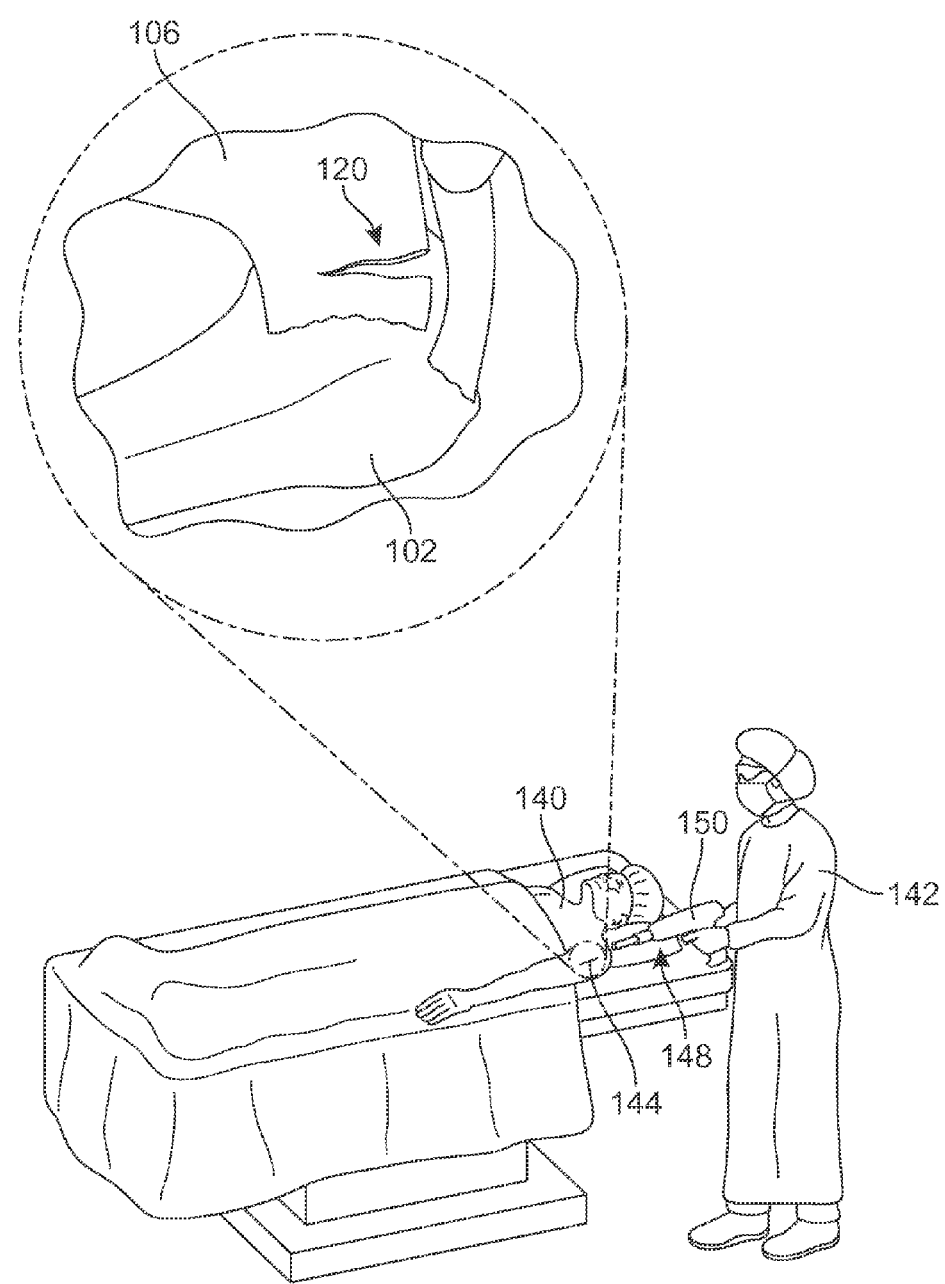
FIG. 4 is a schematic diagram that shows a surgeon preparing to repair a torn rotator cuff tendon according to one embodiment.
Figure 73:
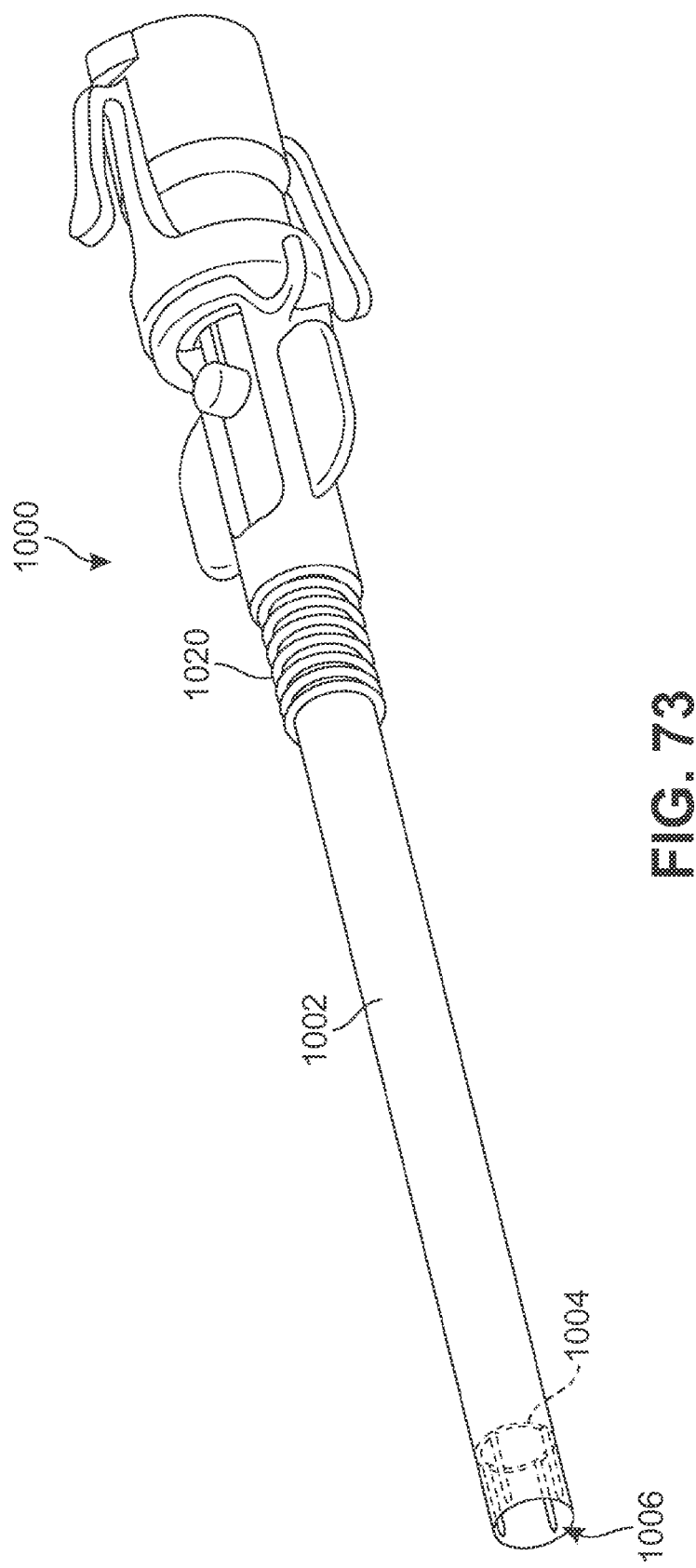
FIG. 73 is a schematic diagram illustrating an isometric view of an embodiment of a front delivery assembly in which a plurality of holding members may be hidden within a retractable cannula of the front delivery assembly.

In contrast to the embodiment shown in FIG. 3, FIGS. 4 through 73 are directed towards embodiments of a system and method that simplifies the repair of a rotator cuff tendon by limiting the complexity of the repair as well as the number of steps involved. The system and method described below may be generally characterized by a plurality of prostheses and an associated deployment device for implanting the plurality of prostheses. In some embodiments, the plurality of prostheses could be physically attached through some joining mechanism, or simply intended for use together. In some cases, for example, a plurality of prostheses may comprise a plurality of suturing anchors that are joined using one or more suture threads. However, in other embodiments, a plurality of prostheses could comprise other kinds of prostheses known in the art. Moreover, the term "prosthesis" as used throughout this detailed description and in the claims refers to any device, component, or other element that is configured to be implanted into a portion of the body. It will be understood that the term prosthesis is not intended to designate a particular structure, material, location, or function.

FIG. 4 illustrates a schematic view of patient 140 undergoing rotator cuff repair surgery. Specifically, surgeon 142 may perform a surgical procedure that attempts to repair tear 120 of tendon 106. Surgeon 142 may be provided with tissue repair system 148 according to one embodiment. In some embodiments, tissue repair system 148 may comprise plurality of prostheses 160 (see FIG. 5) that may be implanted into tendon 106 and/or humerus 102 in order to repair tear 120. In some embodiments, tissue repair system 148 may also comprise deployment device 150, which is used to implant plurality of prostheses 160 at the location of tear 120.

For purposes of clarity, patient 140 is shown with a single incision 144 through which deployment device 150 may be inserted to facilitate the implantation of one or more prostheses. However, in some cases, additional incisions may be made at the shoulder to facilitate the use of other instrumentation. For example, an arthroscope may be inserted into a second incision simultaneously with the insertion of deployment device 150 into incision 144. This may allow surgeon 142 to inspect tear 120 carefully and may also be used to guide the implantation of one or more prostheses using deployment device 150. Moreover, it will also be understood that in other situations, tissue repair system 148 could be used in conjunction with any other surgical technique including open surgery, in which the shoulder joint may be fully exposed during implantation.

Although the following embodiments describe the use of tissue repair system 148 for repairing tears in a rotator cuff tendon, the applications of tissue repair system 148 are not limited to this particular use. Instead, this particular application simply highlights how one type of tissue repair may be improved through the use of tissue repair system 148. Moreover, this method could be utilized in repairing a wide range of imperfections or irregularities in tissue including, but not limited to: flaws, holes, tears, bulges, a deliberate cut or incision, as well as any other imperfections.

Figure 5:
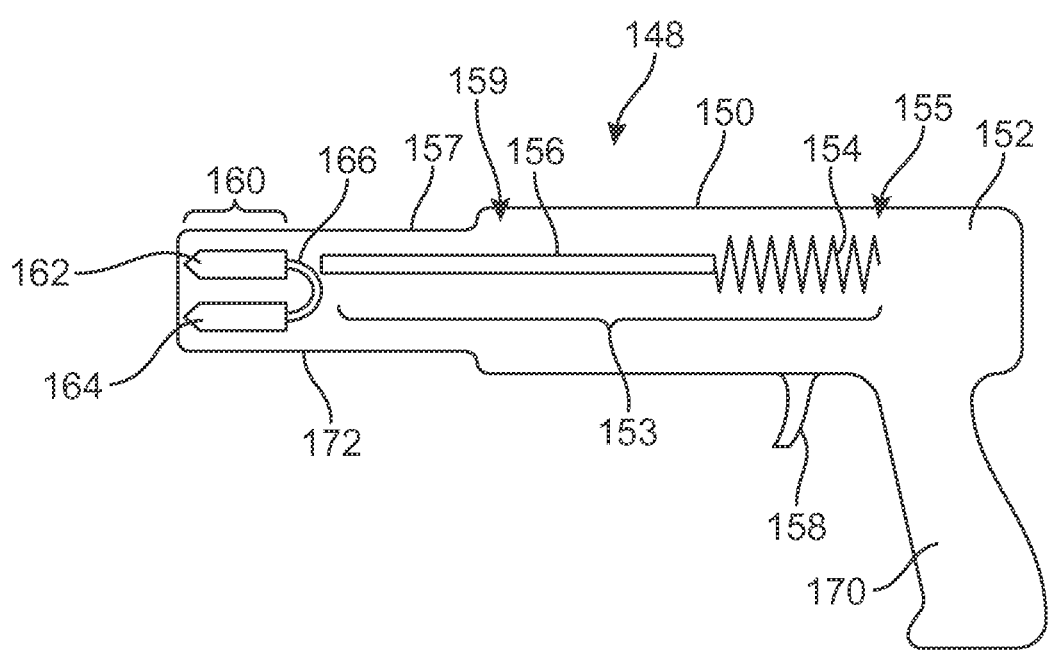
FIG. 5 is a schematic diagram of an embodiment of a deployment device as well as various components of the deployment device.

FIG. 5 illustrates a schematic view of one possible embodiment of tissue repair system 148. For purposes of clarity, deployment device 150, plurality of prostheses 160, and their corresponding sub-components are shown schematically in FIGS. 5 through 13. Referring to FIG. 5, each prosthesis of plurality of prostheses 160 may be joined by connecting member 166 while housed within deployment device 150. In some embodiments, connecting member 166 may be a suture thread. However, in other embodiments, connecting member 166 could comprise a more rigid member. In another embodiment, for example, connecting member 166 could comprise a plastic connecting member that is substantially stiffer than a suture thread. In still other embodiments, the structural properties of connecting member 166 may vary in any manner and may generally be determined according to the type of repair needed. For example, in situations where tissue repair system 148 may be used to fasten different portions of bone together, a connecting member that is substantially more rigid than suture thread may be used to help fasten the portions of bone together. Still other examples of connecting members include, but are not limited to nets and meshes.

In one embodiment, plurality of prostheses 160 includes first prosthesis 162 and second prosthesis 164. In some embodiments, first prosthesis 162 and/or second prosthesis 164 may comprise anchors that are intended for implantation into one or more kinds of tissue. This configuration may allow first prosthesis 162 and second prosthesis 164 to act as anchors for connecting member 166, which may comprise a suture thread as previously discussed.

In different embodiments, the general form or structure of deployment device 150 may vary. In one embodiment, for example, housing 152 of deployment device 150 may take the form of a handheld device. In some cases, housing 152 may include a handgrip portion 170. This general shape allows deployment device 150 to be easily handled and used. Although the current embodiment illustrates a generic shape for handgrip portion 170, other embodiments could include additional provisions to enhance handling and use. For example, some embodiments could incorporate contours that conform to the natural shape and position of fingers along handgrip portion 170. Still other embodiments could use pads or similar provisions to enhance grip and/or cushioning.

In some embodiments, deployment device 150 may be configured to temporarily house plurality of prostheses 160 up until the time of implantation. In some cases, therefore, housing 152 may include delivery portion 172 that extends away from handgrip portion 170. With handgrip portion 170 held by the surgeon, delivery portion 172 may be configured to insert through an incision or other opening in order to align plurality of prostheses 160 with the desired region of tissue. In some cases, therefore, delivery portion 172 may be configured with a narrow tube-like, or barrel, shape. This shape for delivery portion 172 may help to reduce the footprint of deployment device 150 at the intended implantation site in order to improve precision of the deployment. In still other embodiments, delivery portion 172 could be configured with any other geometry. Other suitable geometries for a delivery portion may be selected according to various factors including the type of incision, the number, and/or arrangement of prostheses as well as other factors.

Deployment device 150 may include provisions for assisting a surgeon with implanting plurality of prostheses 160 into tissue. In some cases, deployment device 150 may include actuating system 153. Generally, actuating system 153 could utilize any kind of actuators known in the art. In some cases, actuating system 153 may include an energy storage system 155. In some cases, actuating system 153 may further include driving system 159. Using power generated by energy storage system 155, driving system 159 may generally apply the necessary impact and driving forces to implant first prosthesis 162 and/or second prosthesis 164.

As one possible example, actuating system 153 is depicted schematically in FIG. 5 as comprising spring 154 and driving rod 156, which may be particular components of energy storage system 155 and driving system 159, respectively. As spring 154 expands, the mechanical energy stored within spring 154 generates the linear motion of driving rod 156, which further acts to deploy one or more of plurality of prostheses 160 from deployment device 150. Other embodiments could use any other kind of energy storage systems for generating the required force to implant plurality of prostheses 160 into tissue. In another embodiment, for example, energy storage system 155 could comprise a chemical energy storage system, such as a battery. Still other embodiments could use hydraulic energy, pneumatic energy, and/or electrical energy to generate the necessary impact and driving forces for implanting prostheses. In still another embodiment, combustion could be used to generate power for implanting prostheses. It should be understood that deployment device 150 could include additional provisions for charging, or otherwise supplying sources of stored energy, for energy storage system 155. For example, in embodiments where energy storage system 155 includes a battery, deployment device 150 could include provisions for recharging and/or interchanging a battery. As another example, in embodiments where energy storage system 155 uses combustion to actuate driving system 159, deployment device 150 could include provisions for replacing the source of the combustion energy (such as an explosive powder).

For purposes of clarity, driving system 159 is illustrated schematically as comprising a single driving rod 156 that acts to propel plurality of prostheses 160 into a tissue. In other embodiments, driving system 159 could comprise multiple components. For example, some embodiments could incorporate one or more driven rods that mediate the transfer of forces between a driving rod and a prosthesis. Still other cases may include multiple driving components and multiple driven components. For example, one embodiment described in detail below includes a driving assembly with a driving pin and a driving tube that houses the driving pin. The driving pin and driving tube may further interact with one or more driven assemblies, where each driven assembly includes a driven pin and a corresponding driven tube.

In some embodiments, driving system 159 may be designed to facilitate the implantation of plurality of prostheses 160 in a precisely controlled manner. For example, driving system 159 may be designed to deliver a predetermined amount of force to plurality of prostheses 160. Additionally, in some embodiments, driving system 159 may be designed to vary the location at which force is applied to plurality of prostheses 160. In some embodiments, driving system 159 may also be designed to deliver force to plurality of prostheses 160 in multiple stages, rather than at a single instance. It will therefore be understood that other embodiments of driving system 159 could incorporate any other components or systems that facilitate increased control over the implantation process.

Deployment device 150 can also include provisions that allow a user (such as a surgeon) to activate actuating system 153. In some cases, deployment device 150 may include user activation device 158. In FIG. 5, user activation device 158 is shown schematically as a trigger. In other embodiments, deployment device 150 could include other kinds of activation devices, including, but not limited to: mechanical push buttons, electronic buttons, knobs, dials, and switches, as well as any other activation devices known in the art. Moreover, some embodiments could include various devices for modifying the operating properties of actuating system 153. For example, some embodiments could include a control knob or dial for varying the magnitude of the impact force generated by actuating system 153. An example of such a control knob is described below.

Using the configuration described here, deployment device 150 may be capable of providing assistance to a surgeon when implanting one or more prostheses. In particular, energy storage system 155, which can include components such as spring 154, may provide assistance in generating the amount of force required to insert a prosthesis into various kinds of tissue, including bone. This power assistance can greatly increase ease of use over systems that may require the surgeon to generate an impact force directly. Furthermore, the force generated by an energy storage system such as a spring may facilitate a more controlled impact and driving motion for driving system 159 in comparison to systems that may use mechanical energy generated directly by a surgeon.

It will be understood that in some embodiments user activation device 158 may be used to both store energy in energy storage system 155 and release energy from energy storage system 155. For example, in some embodiments user activation device 158 may be a trigger that is used to load spring 154 and to release spring 154. In some cases, both loading and releasing of spring 154 may occur as a surgeon fully squeezes user activation device 158. In other cases, however, user activation device 158 may only be used to release energy from energy storage system 155. In such cases, deployment device 150 could incorporate additional provisions for loading spring 154.

Some embodiments of deployment device 150 can also include provisions for implanting multiple prostheses in a sequential manner. In some embodiments, deployment device 150 includes provisions for aligning multiple prostheses with driving rod 156 in a sequential manner. In one embodiment, this may be accomplished through the use of rotating portion 157. In some cases, rotating portion 157 comprises a portion of delivery portion 172 that is configured to rotate the positions of plurality of prostheses 160. In one embodiment, rotating portion 157 may be rotated to align driving rod 156 with different prostheses.

For consistency and convenience, reference is made to a forward-most end of a deployment device and a rearward-most end of a deployment device. The forward-most end of a deployment device may be the end where a prosthesis is configured to exit the deployment device. The rearward-most end may be the opposing end of the deployment device. In general use, the forward-most end may be disposed farthest from a surgeon, while the rearward-most end may be disposed closest to the surgeon. Moreover, the terms "forward end" or "forward end portion" may describe portions of a component that are closer to the forward-most end of a deployment device. Likewise, the terms "rearward end" or "rearward end portion" may describe portions of a component that are closer to the rearward-most end of a deployment device.

Figure 6:
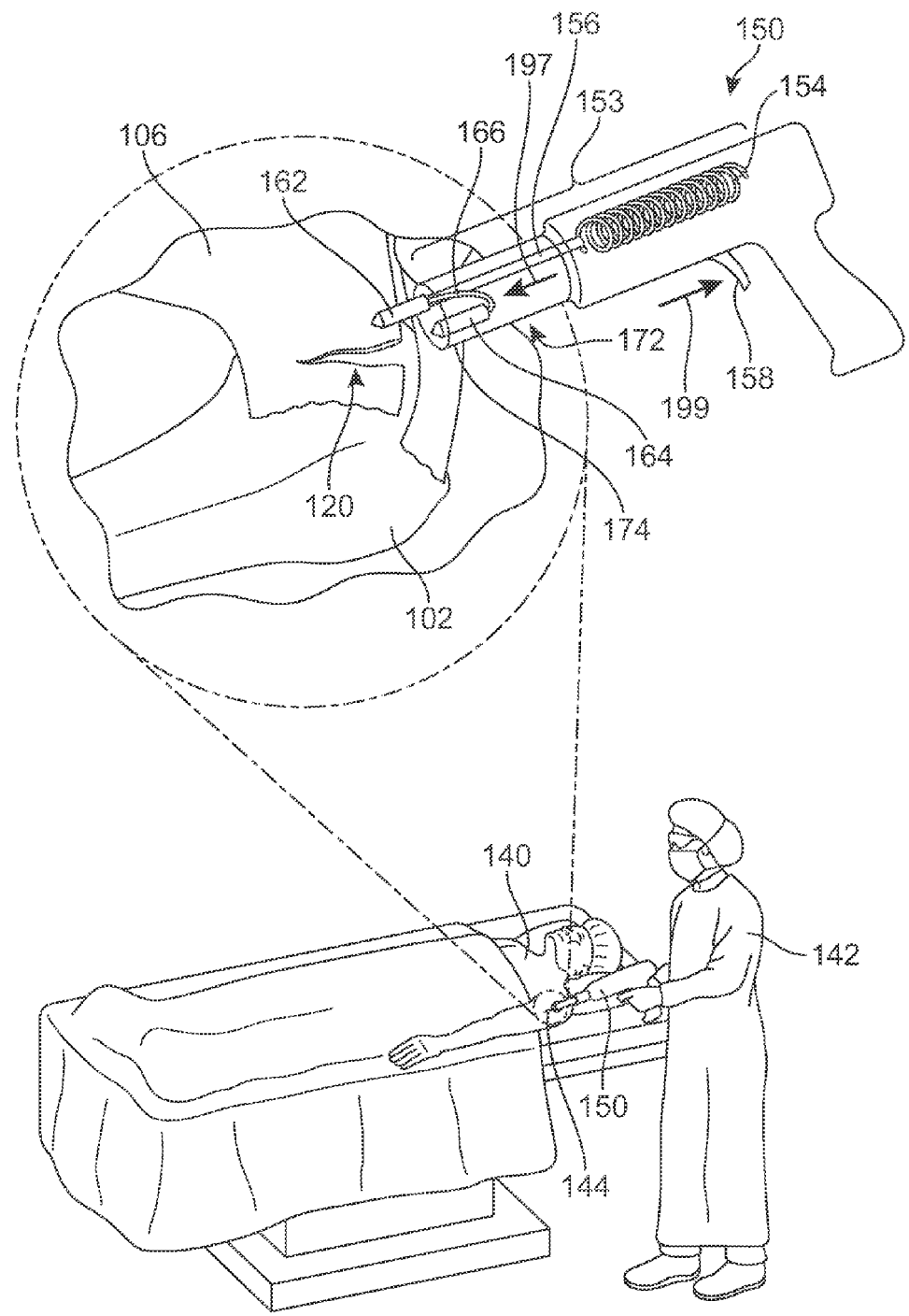
FIG. 6 is a schematic diagram that shows a surgeon using a deployment device to install a first prosthesis according to one embodiment.
Figure 7:
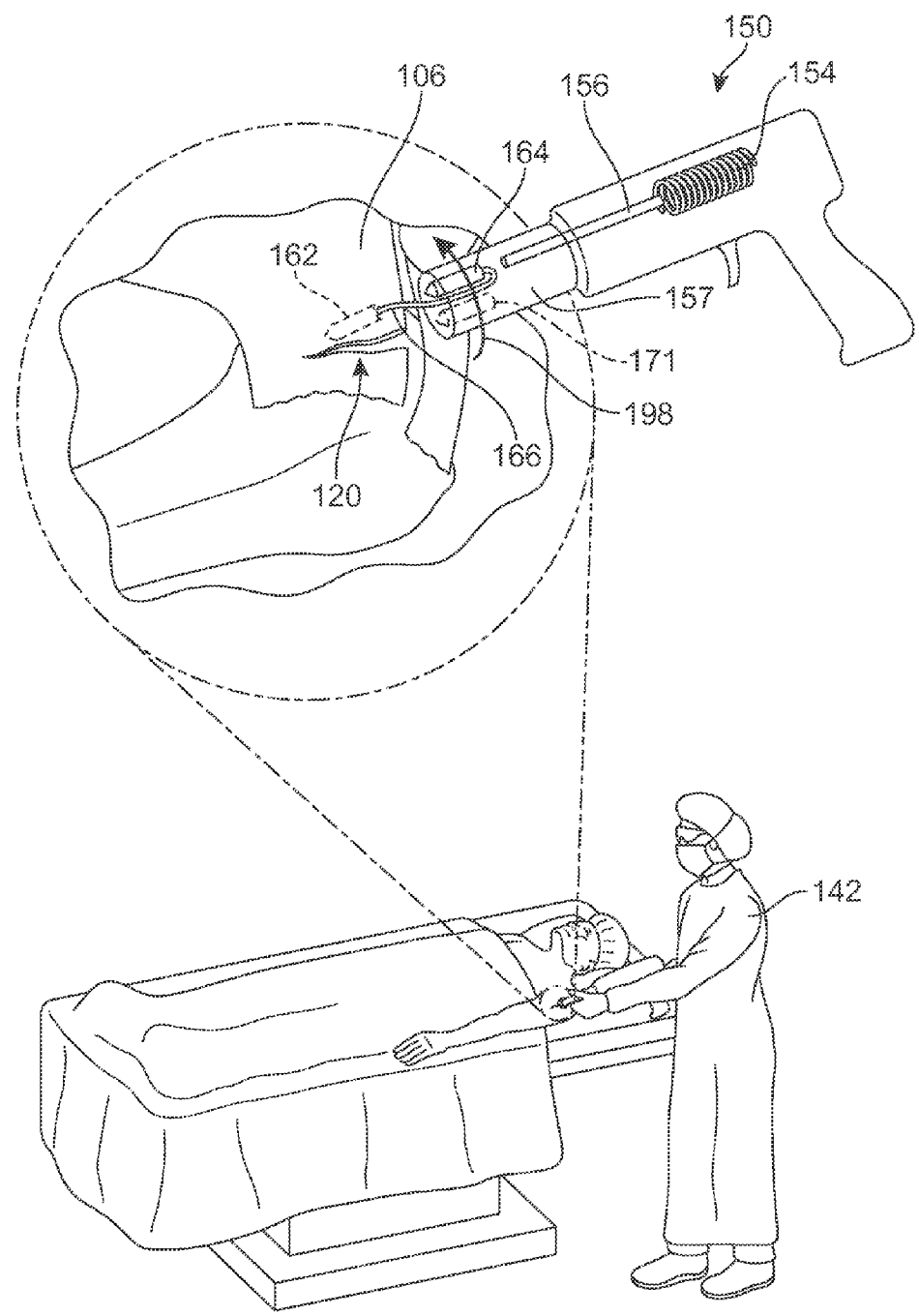
FIG. 7 is a schematic diagram that shows a surgeon adjusting a deployment device to align a second prosthesis with a driving device according to one embodiment.
Figure 8:
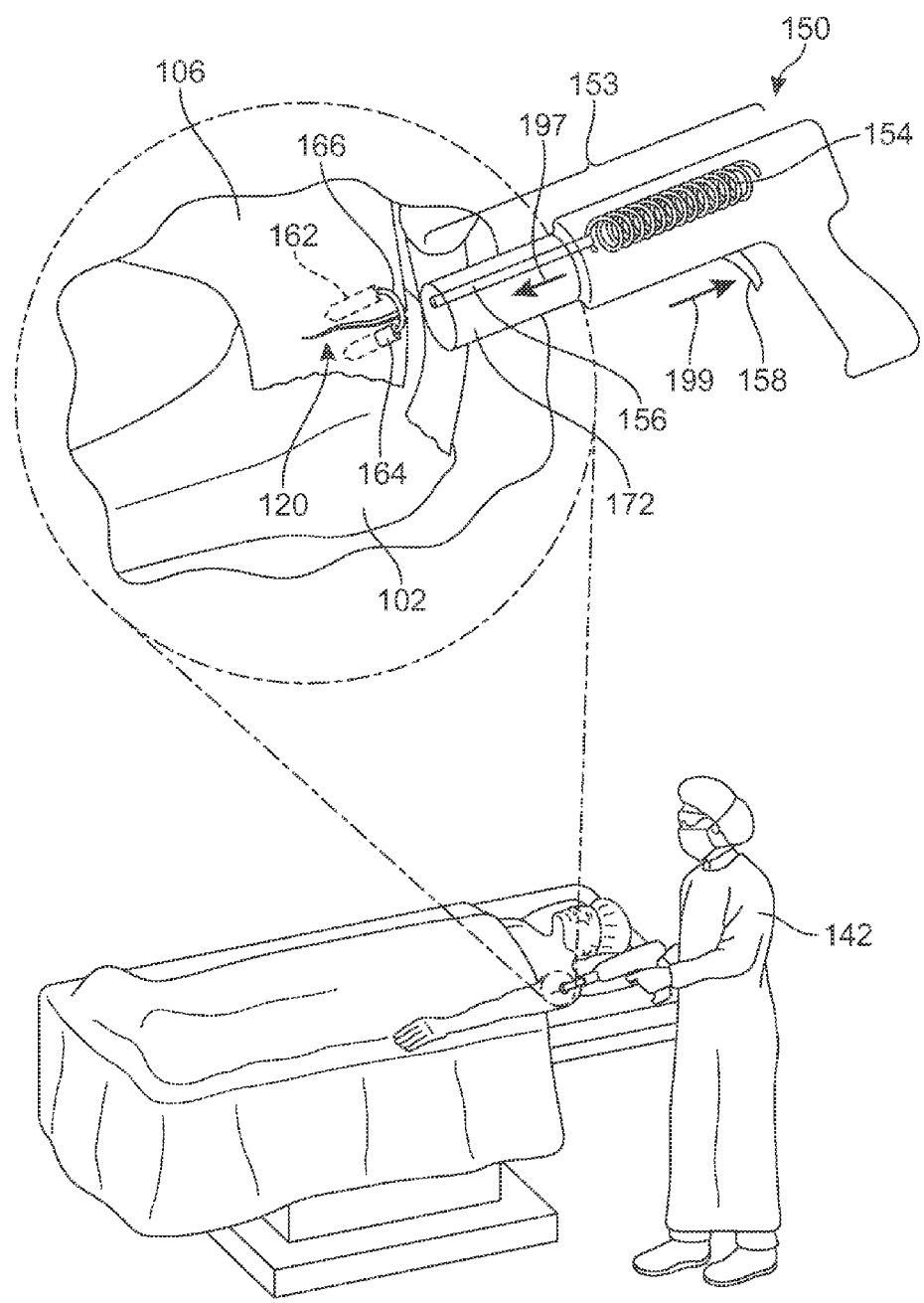
FIG. 8 is a schematic diagram that shows a surgeon using a deployment device to install a second prosthesis according to one embodiment.

FIGS. 6 through 8 illustrate views of a process for repairing a rotator cuff tendon using tissue repair system 148 (see FIG. 5) according to one embodiment. More specifically, each figure illustrates one possible step, or set of steps, in the process. As seen in FIG. 6, surgeon 142 may insert delivery portion 172 of deployment device 150 into incision 144. Generally, surgeon 142 may attempt to align forward end 174 of delivery portion 172 at a first location associated with tear 120. In some cases, as discussed above, surgeon 142 may use an arthroscope or similar device to guide forward end 174 to the first location of tear 120. In addition, in some cases, deployment device 150 may include provisions that allow surgeon 142 to manipulate one or more portions of tendon 106. For example, deployment device 150 could include provisions for grasping tendon 106 on either side (or both sides) of tear 120. Some embodiments, for example, could include pin-like members that project outwardly from forward end 174 and help to hold down the tendon during implantation. An example of such an embodiment is described in detail below and shown in FIGS. 71 through 73.

As represented by arrow 199, as surgeon 142 squeezes user activation device 158, actuating system 153 is activated and applies a driving force to first prosthesis 162. As user activation device 158 is depressed, energy may be released from energy storage system 155 (see FIG. 5). In particular, spring 154 is released from a compressed state and expands rapidly, which acts to propel driving rod 156 and first prosthesis 162. In FIG. 6, arrow 197 represents the motion of driving rod 156 and first prosthesis 162 as spring 154 expands. First prosthesis 162 is then driven through tendon 106 and into greater tuberosity 104 of humerus 102. Thus, the implantation of first prosthesis 162 facilitates the joining of the opposing edges of tear 120 of tendon 106. Once implanted into humerus 102, first prosthesis 162 serves as an anchor for one end of connecting member 166.

The amount of force applied by actuating system 153 may vary in different embodiments. Generally, the amount of force applied can be selected according to various different factors. For example, the amount of force applied can vary according to the type of tissue into which a plurality of prostheses is implanted. In particular, in some cases, a greater degree of force may be necessary for harder tissues such as bone. Less force may be necessary for implanting prostheses into softer tissue. As another example, the amount of force applied by actuating system 153 can vary according to size, material composition, and/or geometry of one or more prostheses. In some embodiments, for example, the amount of force applied may vary according to the geometry of the driving head of an anchor-type prosthesis.

In different embodiments, various different methods could be used to vary the force applied by actuating system 153. In embodiments including a spring for storing energy, for example, the amount of pre-compression of the spring could be changed through a dial or other mechanism. An example of a control knob for adjusting the compression of a spring is discussed in further detail below. In systems using electrical energy storage systems, the amount of electrical energy stored and/or applied could be adjustable. In still other embodiments, any other methods known in the art for modifying the amount of force delivered, or otherwise produced, by an actuating system could be used.

Referring now to FIG. 7, once first prosthesis 162 has been implanted, surgeon 142 may prepare deployment device 150 to implant second prosthesis 164. In the current embodiment, rotating portion 157 of deployment device 150 may be rotated in a direction represented by arrow 198 until second prosthesis 164 comes into alignment with driving rod 156. In FIG. 7, the initial position 171 of second prosthesis 164 prior to the rotation is indicated schematically in order to clearly show how the position of second prosthesis 164 changes. It is contemplated that the adjustment of the position of second prosthesis 164 could be accomplished through either a manual adjustment (as shown in FIG. 7) or an automatic adjustment. FIG. 7 illustrates the rotation of rotating portion 157 as occurring in the direction represented by arrow 198. However, it will be understood that in some embodiments rotating portion 157 may be rotated in an opposing direction to the direction represented by arrow 198. In other words, rotating portion 157 could be configured to rotate in a clockwise and/or counterclockwise direction.

Referring now to FIG. 8, once second prosthesis 164 is aligned with driving rod 156, surgeon 142 may associate delivery portion 172 with a second location along tear 120. The second location may be disposed adjacent to the location of first prosthesis 164 in some cases. At this point, surgeon 142 may squeeze user activation device 158 (as represented by arrow 199) to release energy from energy storage system 155 (see FIG. 5). This activates actuating system 153 and drives second prosthesis 164 through tendon 106 and into humerus 102. In particular, second prosthesis 164 is impacted by driving rod 156, which moves in a direction indicated by arrow 197 during the expansion of spring 154. After first prosthesis 162 and second prosthesis 164 have been fully implanted, connecting member 166, which may comprise a suture thread, may be taut against tendon 106. This arrangement may facilitate the closing of tear 120 of tendon 106 by anchoring connecting member 166 at a first location and a second location of tendon 106.

It may be useful to characterize the above sequence of operations in terms of various configurations and/or stages of operation. For example, FIG. 5 may be seen to illustrate an initial configuration of deployment device 150. In this initial configuration, first prosthesis 162 may be in a driving position while second prosthesis 164 may be in a storage position. The driving position is a position within deployment device 150 associated with implantation and may be further characterized as a position in which a prosthesis is generally aligned, or otherwise associated with, actuating system 153. In some cases, first prosthesis 162 may protrude sufficiently to be in contact with tissue for accurate implantation (see FIGS. 15 and 16, for example). Therefore, a prosthesis can be directly implanted from the driving position through the operation of actuating system 153. The storage position is a position within deployment device 150 that is generally out of alignment with actuating system 153, including driving rod 156. Therefore, a prosthesis cannot be implanted directly from the storage position, but must be moved from the storage position to the driving position prior to implantation. It should also be noted that in this initial configuration, connecting member 166 joins first prosthesis 162 and second prosthesis 164, as discussed above.

FIGS. 6 through 8 are seen to illustrate various stages of implantation during the operation of deployment device 150. For example, in FIG. 6, first prosthesis 162 is implanted from a driving position into tendon 106. Moreover, in this situation, connecting member 166 is seen to join prosthesis 162 (now disposed outside of deployment device 150) and second prosthesis 164 (which remains within deployment device 150). Referring to FIG. 7, second prosthesis 164 may be moved from the storage position into the driving position as described above. Finally, as seen in FIG. 8, second prosthesis 164 may be implanted from the driving position.

The method described here for implanting multiple prostheses may facilitate improvements in surgical techniques for repairing various types of tissue imperfections, including, for example, rotator cuff tears. By housing multiple prostheses in a single hand-held deployment device, a surgeon can install multiple prostheses in relatively quick succession.

For purposes of clarity, the embodiments shown in FIGS. 5 through 8 illustrate a plurality of prostheses 160 including two prostheses. However, other embodiments may include any other number of prostheses housed within a single deployment device. In some cases, for example, a deployment device may be configured to house a single prosthesis. In still other cases, a deployment device may be configured to simultaneously house three or more prostheses.

Figure 9:
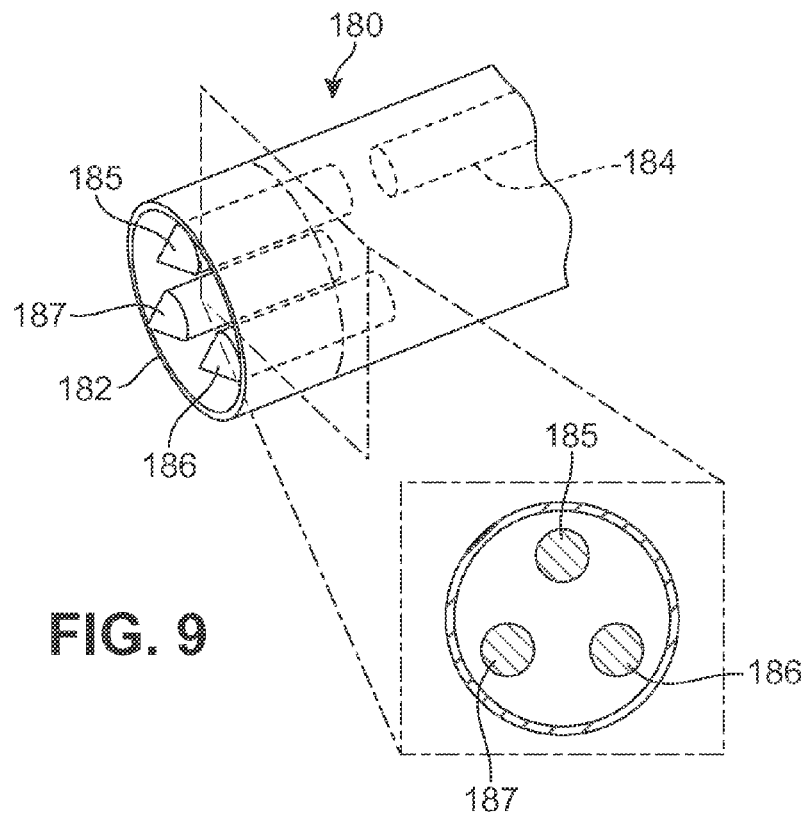
FIG. 9 is a schematic diagram of another embodiment of a portion of a deployment device that is configured to house three prostheses.
Figure 10:
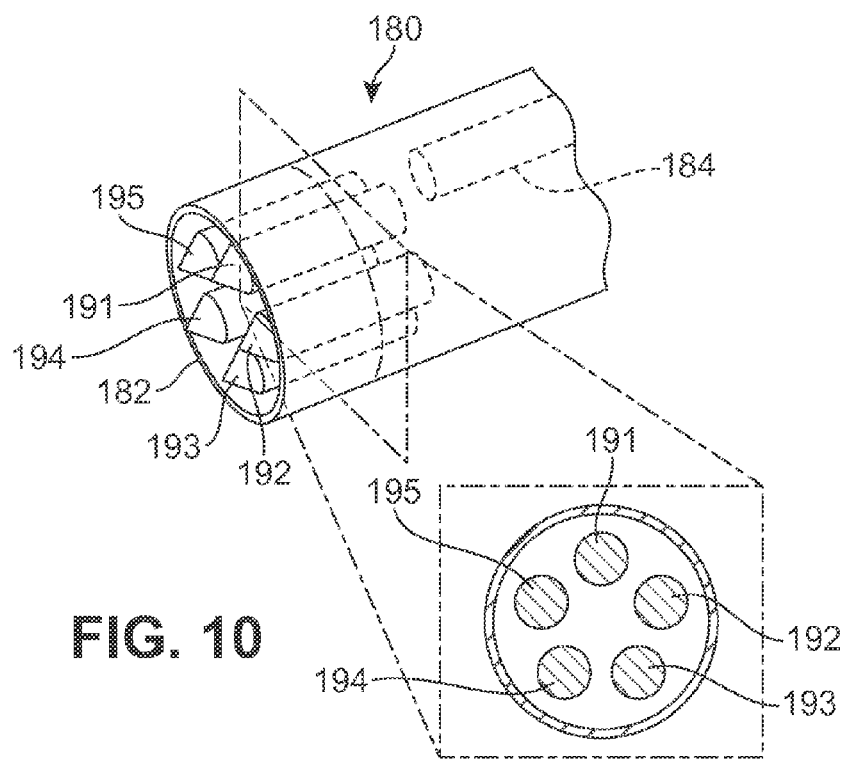
FIG. 10 is a schematic diagram of another embodiment of a portion of a deployment device that is configured to house five prostheses.
Figure 11:
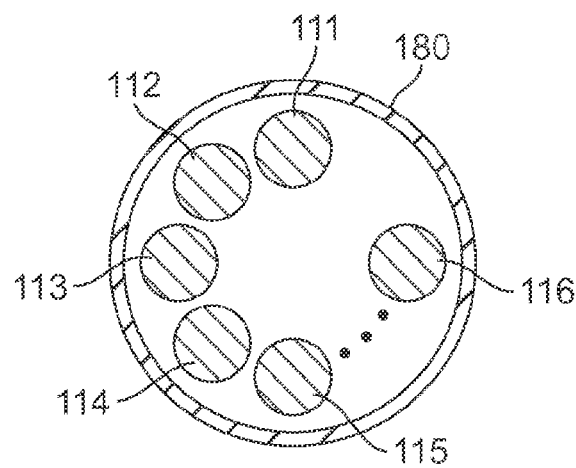
FIG. 11 is a schematic diagram of another embodiment of a portion of a deployment device that is configured to house any desired number of prostheses.

FIGS. 9 through 11 illustrate embodiments of various possible configurations for housing multiple prostheses in a deployment device. In particular, FIGS. 9 and 10 both illustrate schematic views of a forward end 182 of a deployment device 180 as well as corresponding cross-sectional views. FIG. 11 shows a schematic cross-sectional view of deployment device 180 when configured to house any other number of prostheses. Referring first to FIG. 9, deployment device 180 may be configured to simultaneously house three different prostheses. In particular, deployment device 180 houses first prosthesis 185, second prosthesis 186, and third prosthesis 187. Moreover, deployment device 180 may also include driving device 184 that may be used to drive each prosthesis into tissue. As with the embodiment discussed above and shown in FIGS. 5 through 8, each of first prosthesis 185, second prosthesis 186, and third prosthesis 187 can be brought into alignment with driving device 184 in order to implant each prosthesis in succession.

In some embodiments, two or more of first prosthesis 185, second prosthesis 186, and third prosthesis 187 could be connected to one another. In other embodiments, none of the prostheses may be connected. In still other embodiments, each prosthesis may be connected to at least one other prosthesis. In one embodiment, first prosthesis 185 may be joined to second prosthesis 186. Also, second prosthesis 186 may be joined to third prosthesis 187. This provides three prostheses that are daisy-chained to one another. The connections discussed here could be suture threads or any other provisions for connecting two or more prostheses.

Referring next to FIG. 10, in another embodiment, deployment device 180 may be configured to simultaneously house five different prostheses. In particular, deployment device 180 houses first prosthesis 191, second prosthesis 192, third prosthesis 193, fourth prosthesis 194, and fifth prosthesis 195. As with the embodiment discussed above and shown in FIGS. 5 through 8, each of first prosthesis 191, second prosthesis 192, third prosthesis 193, fourth prosthesis 194, and fifth prosthesis 195 can be brought into alignment with driving device 184 in order to implant each prosthesis in succession.

FIG. 11 illustrates an embodiment including N prostheses that are housed within deployment device 180 (shown only in schematic cross section). In particular, this embodiment includes first prosthesis 111, second prosthesis 112, third prosthesis 113, fourth prosthesis 114, and fifth prosthesis 115. Additionally, Nth prosthesis 116 is also shown. It will be understood that N may be any number. Moreover, it is to be understood that the general operation of implanting N prostheses housed within a single deployment device may proceed in a manner similar to that discussed above.

Figure 12:
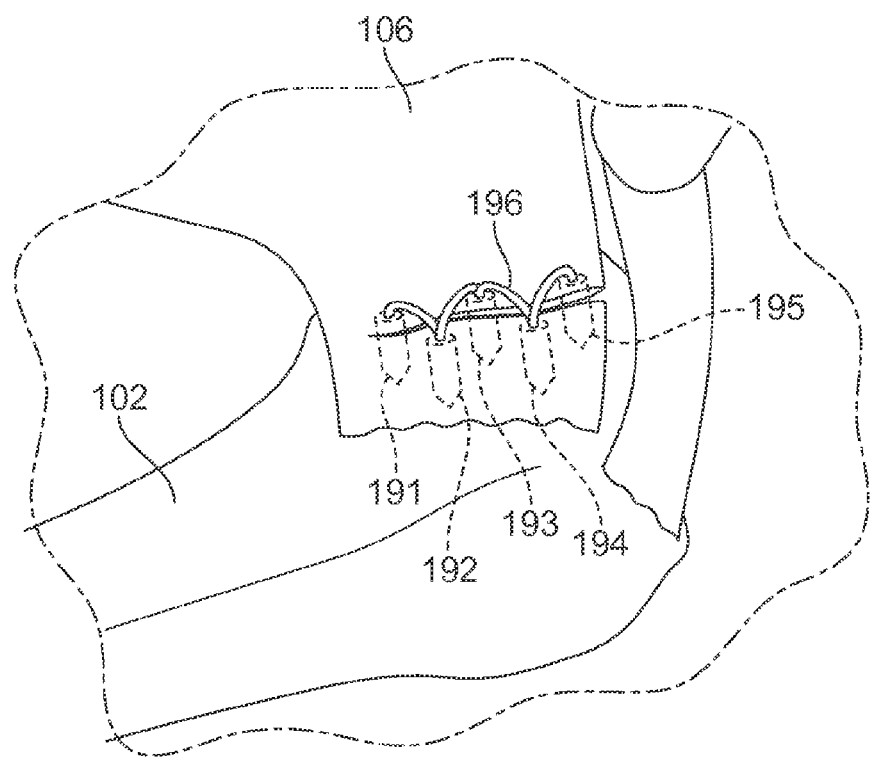
FIG. 12 is a schematic diagram of an embodiment of a plurality of prostheses being used to repair a portion of a rotator cuff tendon.

In some embodiments comprising multiple prostheses housed within a single deployment device, the prostheses could be connected through the use of one or more connecting members. For example, FIG. 12 illustrates a schematic view of an embodiment where first prosthesis 191, second prosthesis 192, third prosthesis 193, fourth prosthesis 194, and fifth prosthesis 195 have been implanted through tendon 106 and into humerus 102. In some embodiments, these prostheses may be connected to one another through connecting member 196. In this particular example, first prosthesis 191, second prosthesis 192, third prosthesis 193, fourth prosthesis 194, and fifth prosthesis 195 may be daisy-chained together using connecting member 196. In some embodiments, connecting member 196 may comprise a suture thread that helps to tie down a portion of tendon 106 against humerus 102. In some cases, first prosthesis 191, second prosthesis 192, third prosthesis 193, fourth prosthesis 194, and fifth prosthesis 195 serve as suture anchors for connecting member 196.

Although the current embodiment illustrates an embodiment where five different prostheses are connected to one another using a single connecting member, other embodiments could use two or more separate connecting members. In some cases, for example, adjacent pairs of prostheses could be attached by distinct connecting members. For example, in an alternative embodiment, first prosthesis 191 and second prosthesis 192 may be connected to one another using a first connecting member, while second prosthesis 192 and third prosthesis 193 may be connected to one another using a different second connecting member. Furthermore, although the approximate arrangement of prostheses in FIG. 12 is generally an alternating or zig-zag configuration, other embodiments may utilize any other suitable arrangement of prostheses in order to repair tissue. Examples of other possible arrangements for two or more anchors include, but are not limited to: lines, curves, various shapes including triangular, rectangular as well as any other kind contour and/or shape. The type of anchor arrangement could be selected according to various factors including the type of imperfection or tear, the location of the imperfection, the type of surgical procedure, preferences of the surgeon, the type of connecting members being used as well as possibly other factors.

General Overview of Tissue Repair System

Figure 13:
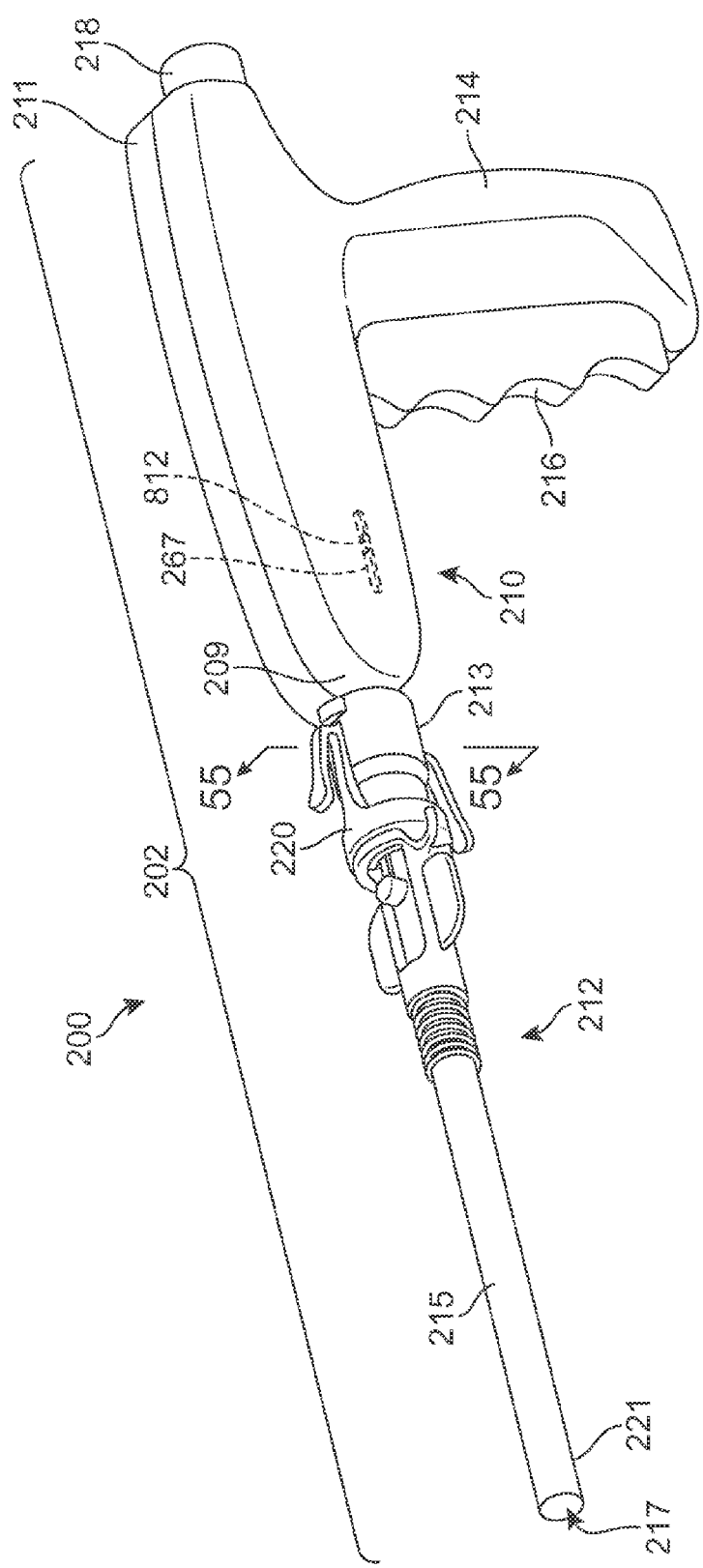
FIG. 13 is a schematic diagram illustrating an isometric view of an embodiment of a tissue repair system.
Figure 14:
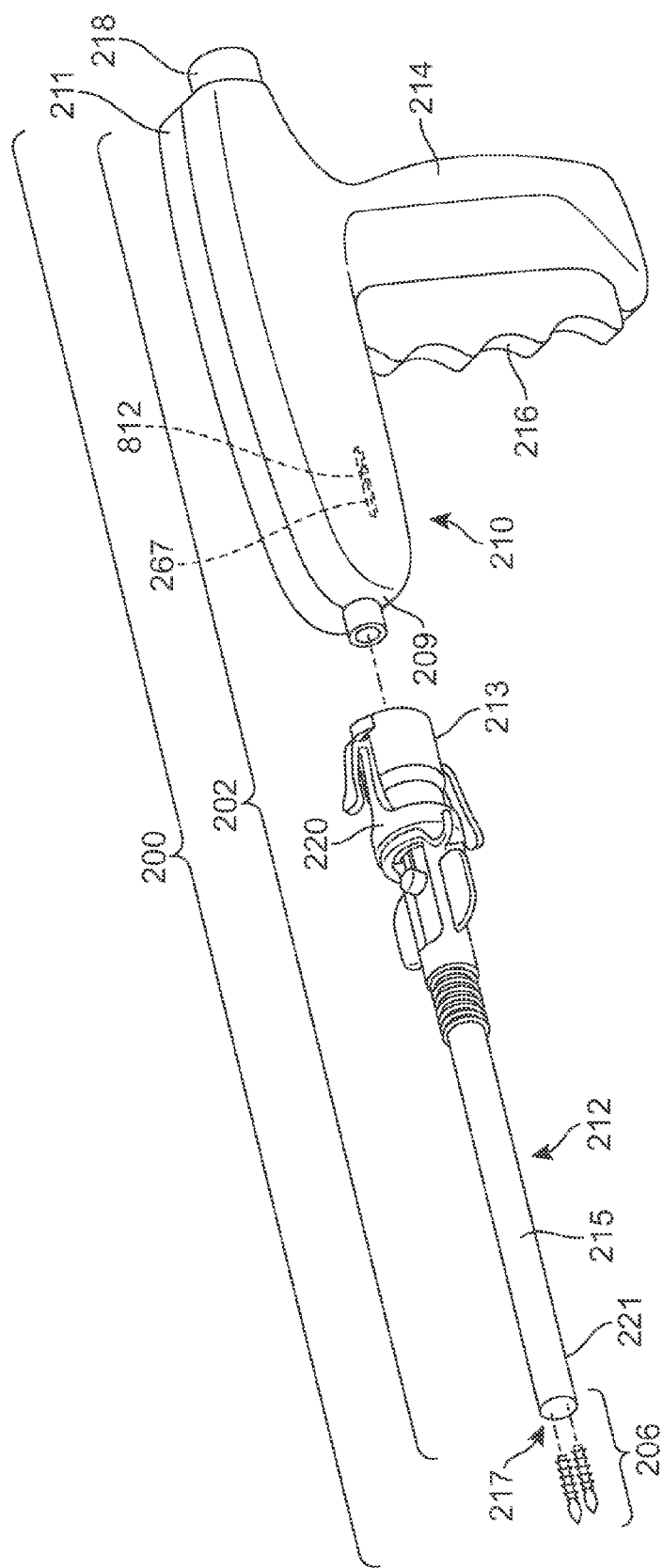
FIG. 14 is a schematic diagram illustrating an isometric exploded view of an embodiment of a tissue repair system that includes a base assembly, a front delivery assembly and a plurality of prostheses.
Figure 15:
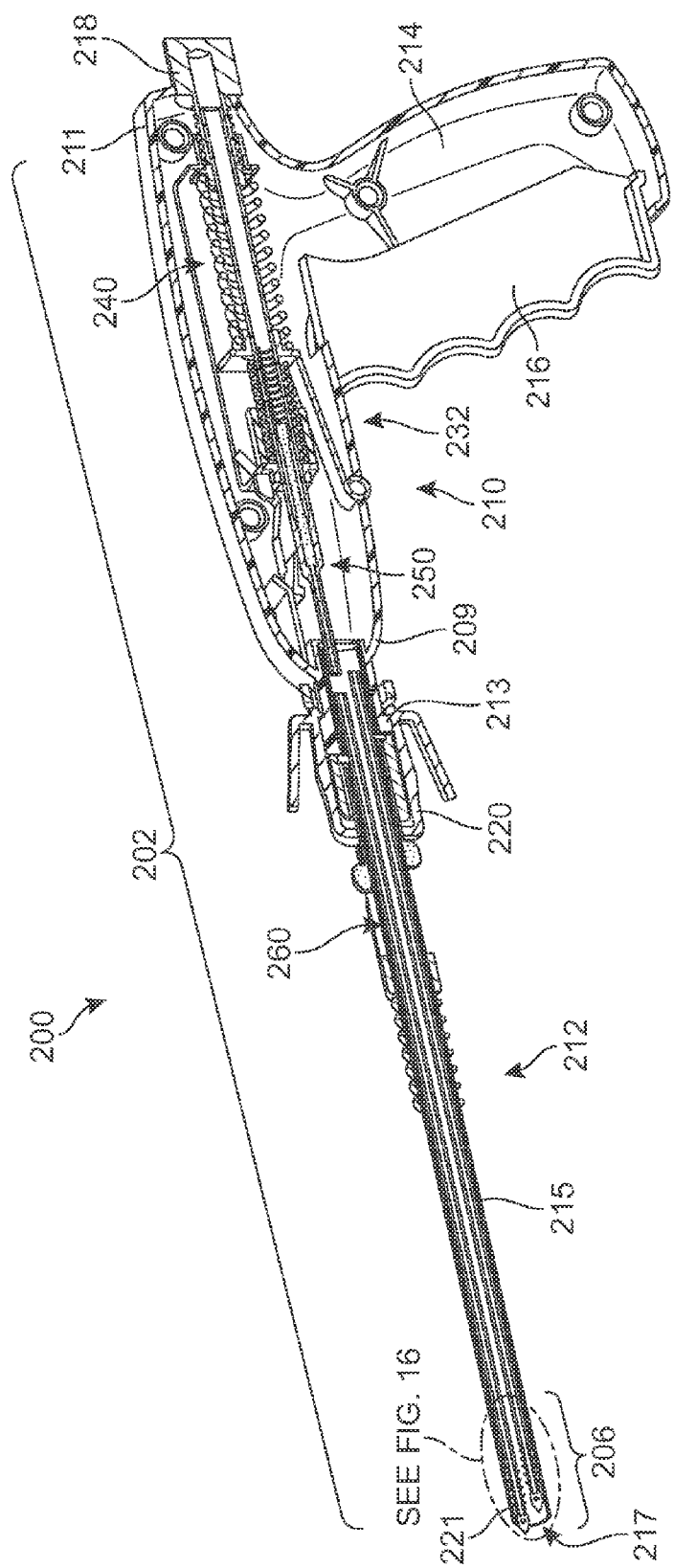
FIG. 15 is a schematic diagram illustrating an isometric cut-away view of an embodiment of a tissue repair system that illustrates various internal components of a deployment device.

FIGS. 13 through 15 illustrate isometric views of one embodiment of tissue repair system 200. In particular, FIGS. 13 and 14 illustrate an isometric view and an isometric partial exploded view, respectively, of tissue repair system 200, while FIG. 15 illustrates a cut-away view of tissue repair system 200.

Referring to FIGS. 13 through 15, tissue repair system 200 may comprise various sub-components including deployment device 202 and plurality of prostheses 206. Deployment device 202 may comprise a body that includes a number of elements to assist in inserting and installing plurality of prostheses 206. In some cases, deployment device 202 includes provisions to move one or more of plurality of prostheses 206 into position. Moreover, in some cases, deployment device 202 includes provisions that associate one or more end portions of plurality of prostheses 206 with tissue such as tendon 106 (see FIGS. 1 and 2). In embodiments where prostheses may articulate in some manner following installation (for example, by expanding inside the implanted tissue), deployment device 202 may further include provisions to facilitate articulation of plurality of prostheses 206.

Deployment device 202 may generally be a hand-held device. In some cases, deployment device 202 may be configured for one-handed operation so that all of the various functions can be controlled with one hand. This arrangement allows plurality of prostheses 206 to be implanted using a single hand.

Deployment device 202 may be further divided into two sub-assemblies, including a reusable base assembly 210 and a detachable front delivery assembly 212. In some cases, base assembly 210 may comprise various components for generating an impact force that is used to deploy plurality of prostheses 206. In some cases, front delivery assembly 212 may include various components for transmitting forces generated within base assembly 210 to plurality of prostheses 206. As seen in FIG. 14, front delivery assembly 212 can be separated from base assembly 210. This allows base assembly 210 to be used with multiple different detachable front delivery systems, as discussed in further detail below.

Base assembly 210 may comprise various provisions to enhance usability. In some cases, base assembly 210 may include handgrip portion 214. Handgrip portion 214 may accommodate either the left or right hand of a surgeon. Although the design of handgrip portion 214 is shown generically in these embodiments, other embodiments could be configured with various additional features. For example, in some other embodiments, the geometry of handgrip portion 214 may be contoured to improve grip. In still other embodiments, handgrip portion 214 could comprise various pads or similar portions that enhance traction and comfort, as well as any other characteristics that improve usability.

Base assembly 210 may incorporate one or more activation devices that help to initiate implantation of a prosthesis. In one embodiment, base assembly 210 may include trigger portion 216. Trigger portion 216 may be squeezed by one or more fingers in order to initiate implantation. As described in further detail below, trigger portion 216 may initiate a sequence of actuating events that act to deploy and implant a prosthesis in a tissue such as bone.

In some embodiments, base assembly 210 can include provisions that allow a surgeon to adjust the magnitude of the impact force generated by components of base assembly 210. For example, some embodiments could include control knob 218. In some cases, control knob 218 may be disposed at a rearward portion 211 of base assembly 210. In other cases, control knob 218 may be disposed along any other portion of base assembly 210.

By turning control knob 218, a surgeon can modify the force generated by deployment device 202. For example, a surgeon may turn control knob 218 in a first direction in order to generally increase the force generated by deployment device 202. Similarly, a surgeon may turn control knob 218 in a second direction in order to generally decrease the force generated by deployment device 202. In some cases, control knob 218 can be adjusted between discrete settings. In other cases, control knob 218 can be adjusted between continuous settings.

Base assembly 210 can include provisions for constraining the motion of one or more components, assemblies or systems disposed internally to base assembly 210. As seen in FIGS. 13 and 14, base assembly 210 may be configured with retaining slot 267 (shown in phantom), which receives a protruding portion 812 that is discussed in further detail below.

Although a single adjustment knob is shown in this example, other embodiments could include still other adjustment devices. In particular, it will be understood that any other kinds of control devices could be used with base assembly 210. Examples of other types of control devices include, but are not limited to: buttons, switches, knobs, touch displays, as well as any other devices or components. Moreover, in other embodiments, one or more control devices could be used for purposes of adjusting any other kinds of operating characteristics of deployment device 202.

Front delivery assembly 212 may extend forwards from base assembly 210. In some embodiments, front delivery assembly 212 may have an elongated geometry. In some embodiments, for example, front delivery assembly 212 has an approximately tube-like geometry. In some embodiments, rearward end portion 213 of front delivery assembly 212 may be attached to forward portion 209 of base assembly 210. In addition, forward end portion 221 of front delivery assembly 212 may be configured to house plurality of prostheses 206.

In some embodiments, front delivery assembly 212 includes attachment assembly 220 that is configured to engage with forward portion 209 of base assembly 210. In some embodiments, front delivery assembly 212 may be a detachable system that can easily be attached to, and detached from, base assembly 210. Moreover, in some embodiments, front delivery assembly 212 can be configured with additional features for changing the positions of plurality of prostheses 206. These features are described in further detail below.

Front delivery assembly 212 may also include cannula 215 that extends forwardly from attachment assembly 220. In some cases, a lumen 217 of cannula 215 may be sized to receive one or more prostheses, as well as additional components that facilitate the driving and implantation of prostheses. In some cases, cannula 215 could be an 8 mm cannula that is configured to house plurality of prostheses 206. In other cases, however, the size of cannula 215 could vary and may depend on the number and size of prostheses housed within cannula 215. Moreover, cannula 215 may be of any length necessary to achieve proper positioning for installation of plurality of prostheses 206.

Referring to FIG. 15, which illustrates some of the internal components of deployment device 202, base assembly 210 and front delivery assembly 212 house various components that generate the required impact forces to implant one or more prostheses. In some cases, base assembly 210 may include trigger assembly 232, energy storage system 240, driving assembly 250, and plurality of driven assemblies 260. The general operation of some of these components according to one embodiment is described here. Trigger assembly 232, including trigger portion 216, may be used to store energy in energy storage system 240 (for example, by compressing a spring) and/or to release mechanical energy stored within energy storage system 240 (for example by releasing a compressed spring). This mechanical energy is converted into motion of driving assembly 250. Driving assembly 250 may further impact, and drive, one or more driven assemblies of plurality of driven assemblies 260. The corresponding driven assembly may then apply a force directly to one of the plurality of prostheses 206, which serves to deploy and implant the prosthesis. The details of trigger assembly 232, energy storage system 240, driving assembly 250, and plurality of driven assemblies 260 are discussed in further detail below.

Expandable Prostheses

Figure 16:
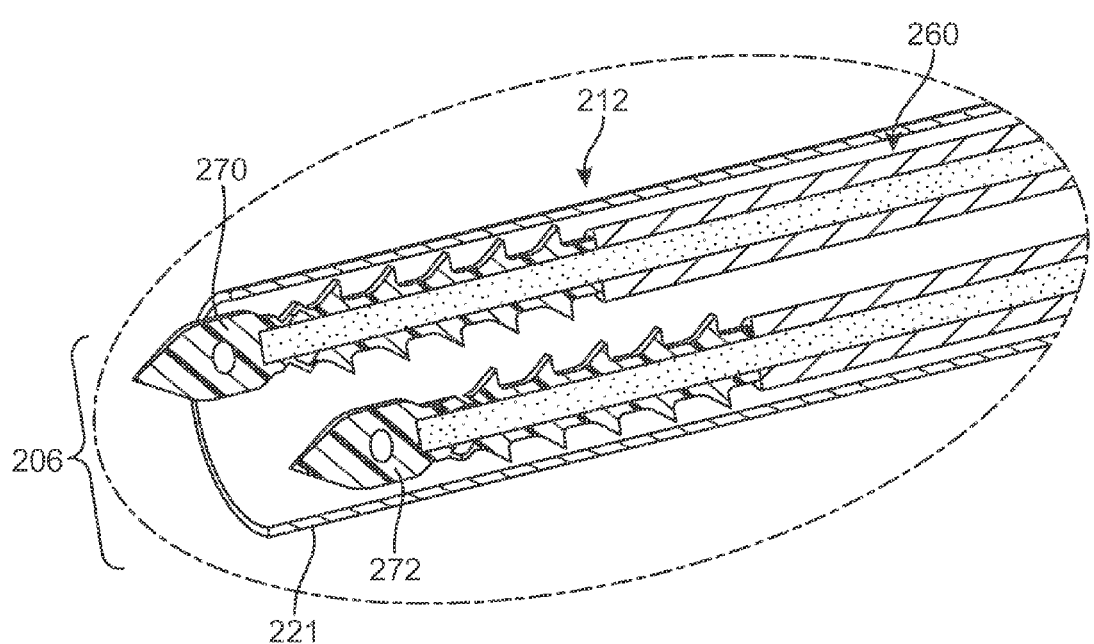
FIG. 16 is a schematic diagram illustrating an enlarged cut-away view of an embodiment of a plurality of prostheses positioned within the end of a front delivery assembly.

FIG. 16 illustrates a schematic cut-away view of an embodiment of plurality of prostheses 206 disposed within forward end portion 221 of front delivery assembly 212. As seen in FIG. 16, plurality of prostheses 206 may further include first prosthesis 270 and second prosthesis 272. In some embodiments, first prosthesis 270 and second prosthesis 272 may be substantially similar. In other embodiments, however, first prosthesis 270 and second prosthesis 272 may be substantially different in shape, size, and/or materials. For the present embodiments, it may be assumed that first prosthesis 270 and second prosthesis 272 are substantially similar. In particular, the following figures and accompanying description focus on the features of first prosthesis 270, though it should be understood that similar principles may also apply to second prosthesis 272.

Figure 61:
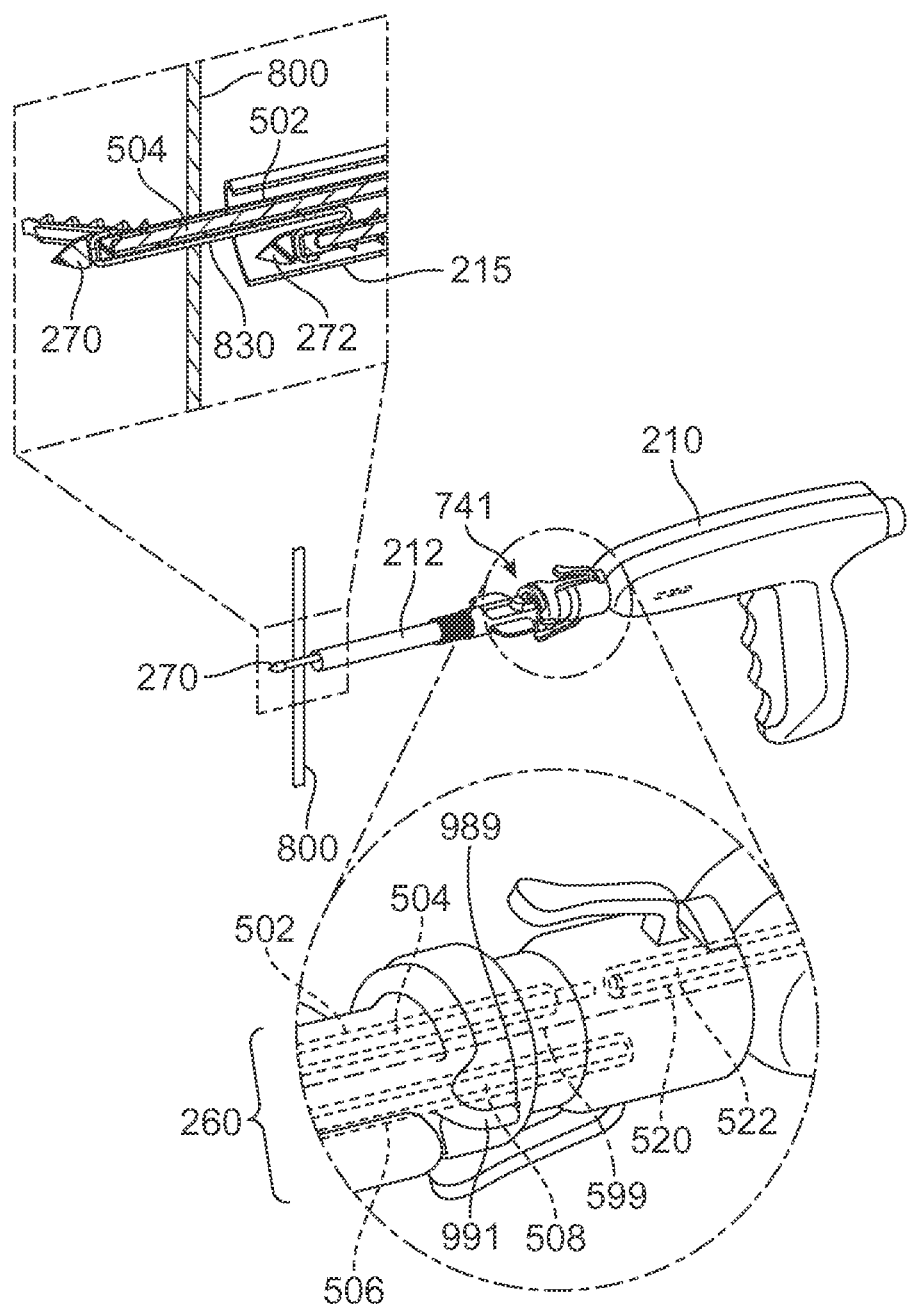
FIG. 61 is a schematic diagram illustrating a schematic view of a method of implanting multiple prostheses according to one embodiment.
Figure 62:
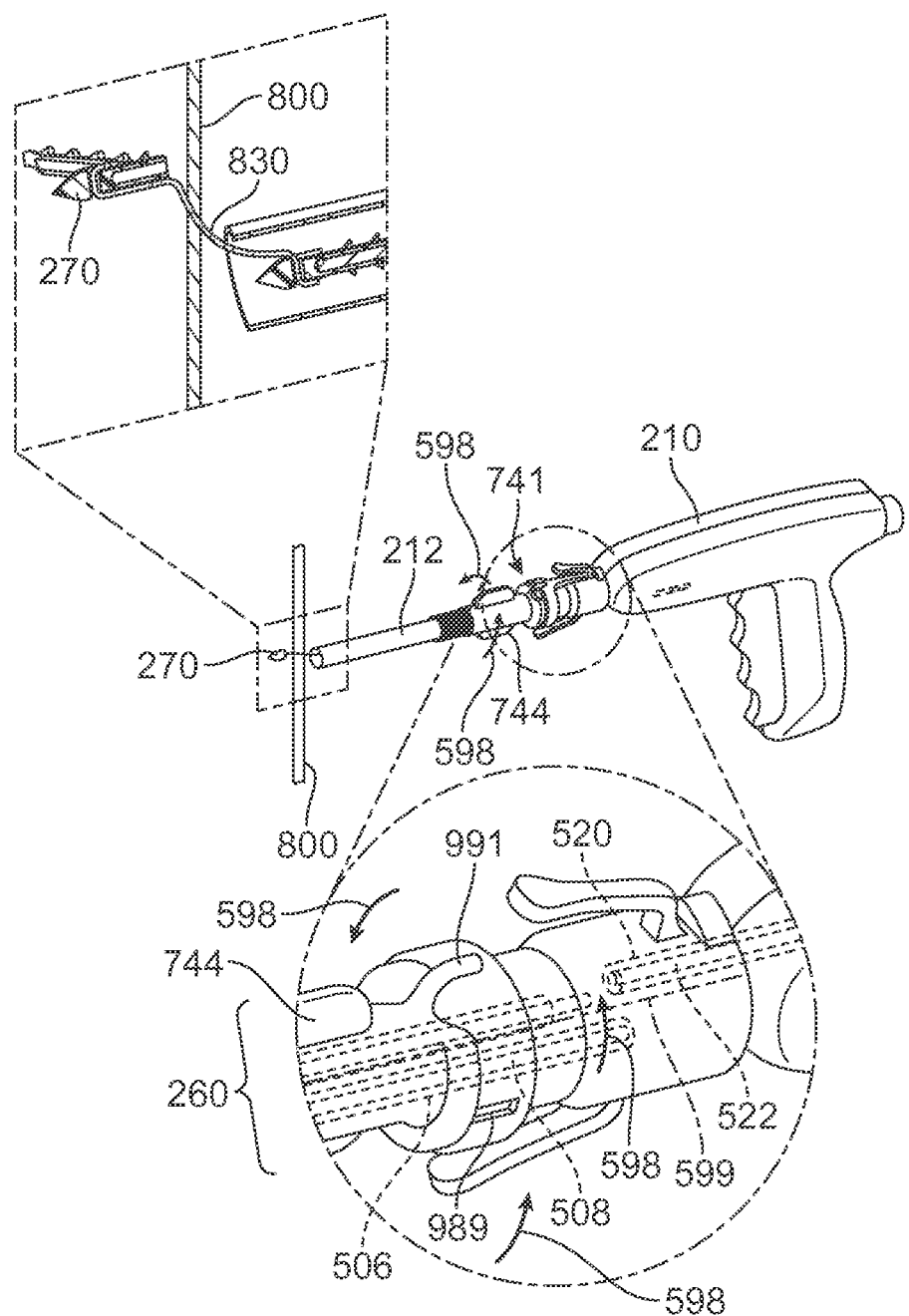
FIG. 62 is a schematic diagram illustrating another view of the method of FIG. 61, in which a rotating assembly has been rotated by 90 degrees.
Figure 63:
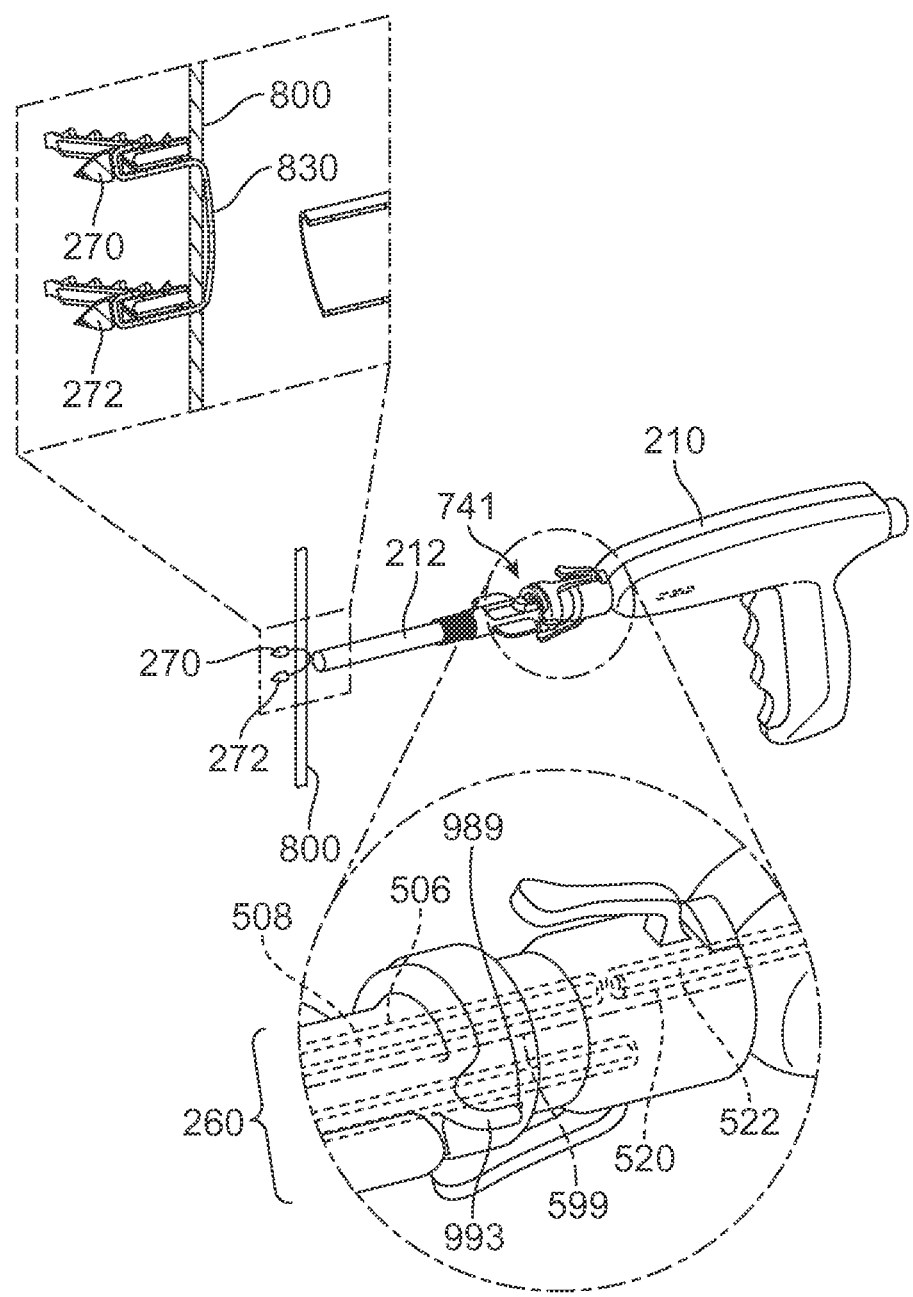
FIG. 63 is a schematic diagram illustrating another view of the method of FIG. 61, in which a rotating assembly has been rotated by 180 degrees.

Although one particular embodiment of prostheses 206 is illustrated in the figures, the size, shape, and other characteristics of prostheses 206 may be determined based on a number of factors, potentially including the size and shape of the imperfection; the condition and type of tissue into which prostheses 206 are to be deployed; and the type and amount of circumferential or other stress that is to be exerted by prostheses 206 on the surrounding tissue. The prostheses 206 may be made in a variety of shapes, as appropriate for different size incisions, cuts, holes, condition of patient, and method of repair. Additionally, although FIG. 16 illustrates an embodiment of prostheses 206 in which both first prosthesis 270 and second prosthesis 272 are of roughly equal size, other embodiments could incorporate two or more prostheses of different sizes. For example, it may be desirable to make one of first prosthesis 270 or second prosthesis 272 larger if needed to provide suitable anchoring for a detached tendon at adjacent tissue locations with varying properties such as size or density. Moreover, it should be understood that the length of any suture or other kind of connecting member that connects first prosthesis 270 and second prosthesis 272 could be varied in order to accommodate various spacings between first prosthesis 270 and second prosthesis 272 following implantation. For purposes of clarity, first prosthesis 270 and second prosthesis 272 are shown without a connecting member attached between them, though a corresponding connecting member 830 between first prosthesis 270 and second prosthesis 272 is shown in FIGS. 61 through 63.

In the embodiment shown in FIG. 16, first prosthesis 270 and second prosthesis 272 may temporarily be mounted to components of plurality of driven assemblies 260. As one of plurality of driven assemblies 260 is impacted by driving assembly 250 (see FIG. 15), first prosthesis 270 and/or second prosthesis 272 may be deployed from forward end portion 221. However, other embodiments may utilize different mechanisms for implanting first prosthesis 270 and/or second prosthesis 272 into tissue. In other words, it should be understood that the prostheses shown in the figures are not limited to use with a particular kind of deployment device.

Figure 17:
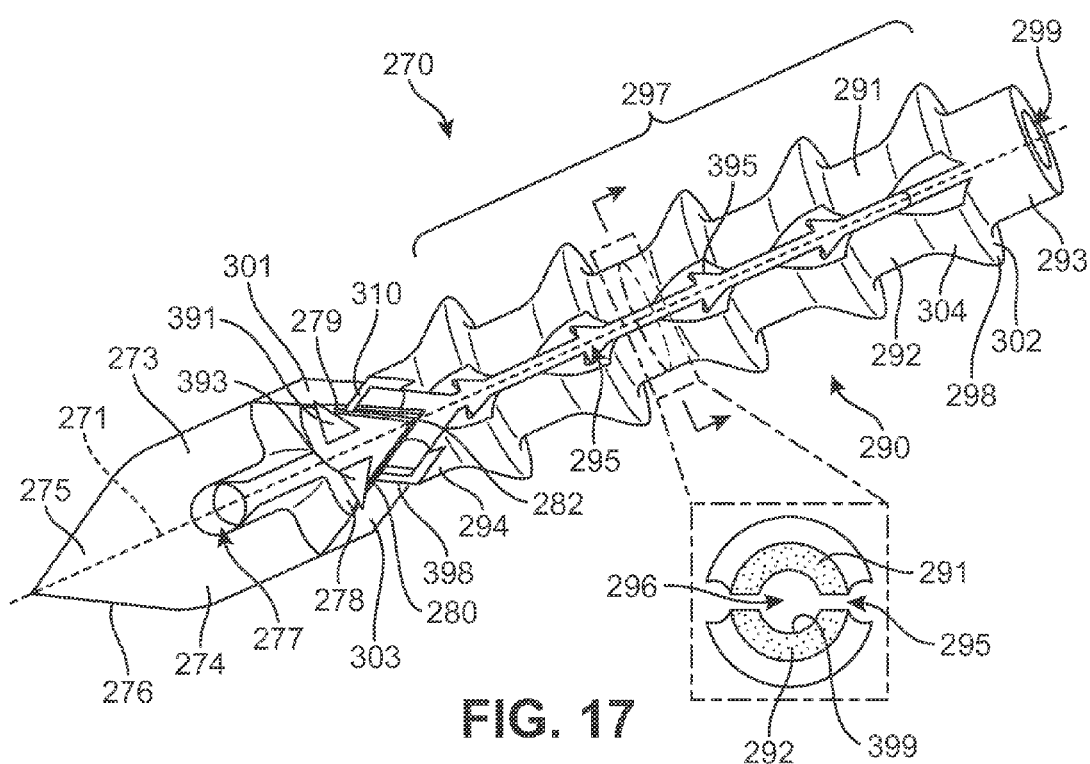
FIG. 17 is a schematic diagram illustrating an isometric view of an embodiment of a prosthesis.
Figure 18:
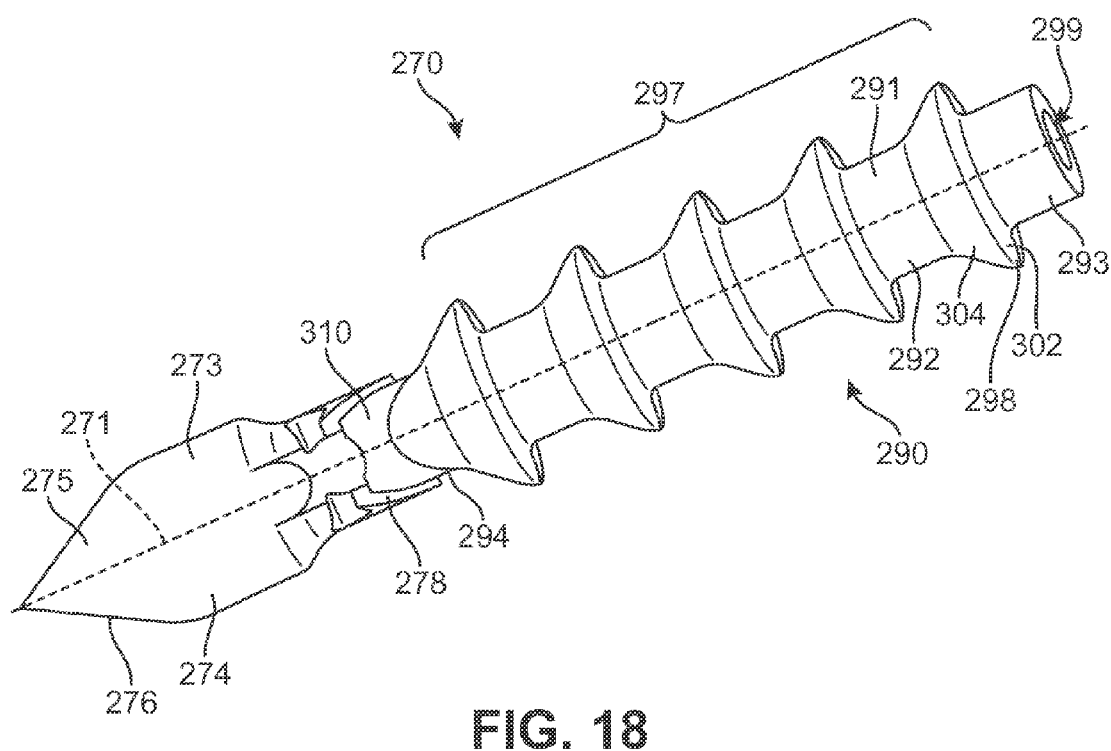
FIG. 18 is a schematic diagram illustrating another isometric view of the prosthesis of FIG. 17, in which the prosthesis has been rotated about a central axis.

FIGS. 17 and 18 illustrate isometric views of an embodiment of first prosthesis 270, or simply prosthesis 270. Specifically, FIG. 17 illustrates a first isometric view of prosthesis 270, while FIG. 18 illustrates a second isometric view of prosthesis 270 in which prosthesis 270 has been rotated approximately 90 degrees around a central axis 271. For purposes of clarity, prosthesis 270 is shown in isolation from components of a deployment device and/or additional prostheses.

As previously discussed with respect to earlier embodiments of a prosthesis, prosthesis 270 may be adapted to repair a flaw, imperfection, cut, incision, hole, or tear in a tissue or collection of tissues. One possible application is the repairing of a rotator cuff tendon tear. However, the use of prosthesis 270 is not limited to this particular application and could be generally applied in a variety of different situations. For example, prosthesis 270 could also be used to repair any other kinds of tendons, muscles, fascia, bone, cartilage, meniscus, ligaments, or skin.

In some embodiments, prosthesis 270 may function as an anchor for a suture that may facilitate repair of a tear or other kind of imperfection. In other embodiments, prosthesis 270 could function as an anchor for any other kind of prosthetic devices apart from sutures. Still other embodiments could utilize prosthesis 270 for directly attaching or otherwise fastening adjacent tissues together.

The geometry of prosthesis 270 could vary from one embodiment to another. In one embodiment, prosthesis 270 may have the approximate geometry of a screw or similar fastening device. In some embodiments, prosthesis 270 may include a driving portion 274 that is disposed at one end of an elongated base portion 290. In other embodiments, however, prosthesis 270 could have any other approximate geometry that is suitable for repairing a particular type of imperfection.

In some embodiments, driving portion 274 is configured with a driving tip portion 275. Driving tip portion 275 may have a tapered or sloped forward surface 276 that facilitates penetration. In some embodiments, driving tip portion 275 may have an approximately conical geometry that may be approximately symmetrical about central axis 271. In other embodiments, however, the geometry of driving tip portion 275 could vary. For example, in other embodiments, the geometry of driving tip portion 275 could be substantially irregular or asymmetric. Moreover, in some embodiments driving tip portion 275 could be configured with additional features such as cavities, projections, mechanical threads or any other geometric features that could enhance and/or control implantation.

In some embodiments, driving portion 274 may include hole 277. In some cases, hole 277 may be a through-hole configured to receive one or more suture threads. For example, one or more suture threads may be inserted through hole 277 in order to fasten the one or more suture threads to prosthesis 270. In some cases, the end of a suture thread may be fed through hole 277 and tied in order to anchor the end of the suture thread in place. In other cases, an intermediate portion of a suture thread could be fed through, looped around, or otherwise associated with hole 277. This arrangement may allow intermediate sections of a suture thread to be anchored in place. In still other embodiments, driving portion 274 could incorporate two or more holes. Such configurations would allow for the attachment of different connecting portions at driving portion 274.

In some embodiments, hole 277 may be disposed in central portion 273 of driving portion 274. In other embodiments, however, hole 277 could be disposed in any other portion of driving portion 274. In still other embodiments, hole 277 could be disposed in base portion 290. In embodiments where multiple suture threads may be used, prosthesis 270 could be provided with multiple holes.

In some embodiments, driving portion 274 may also include wedge portion 278. In some cases, wedge portion 278 extends away from driving tip portion 275 towards base portion 290. Wedge portion 278 may generally have a wedge-like shape that is configured to interact with an end of base portion 290, as described in further detail below. In one embodiment, wedge portion 278 can include a first wedge surface 279 and a second wedge surface 280 that meet along an edge 282.

In some embodiments, base portion 290 comprises a first longitudinal portion 291 and a second longitudinal portion 292 that extend along the length of base portion 290. First longitudinal portion 291 and second longitudinal portion 292 may be joined at a rearward portion 293 of base portion 290. In some embodiments, rearward portion 293 has a ring-like geometry that is approximately symmetric about central axis 271. In addition, in some embodiments, first longitudinal portion 291 and second longitudinal portion 292 may be separated from rearward portion 293 to a forward portion 294 of base portion 290. In some embodiments, first longitudinal portion 291 and second longitudinal portion 292 may generally remain separated at forward portion 294.

In some embodiments, base portion 290 includes longitudinal slot 295, which is clearly seen in FIG. 17. In some embodiments, longitudinal slot 295 may extend through the diameter of base portion 290 and may generally be seen as dividing first longitudinal portion 291 from second longitudinal portion 292. In some cases, longitudinal slot 295 may be characterized as oriented in a lateral direction to an implantation direction of prosthesis 270. In addition, in some embodiments, base portion 290 incorporates a longitudinal cavity 296 that extends through the entire length of base portion 290. In some embodiments, longitudinal cavity 296 may intersect longitudinal slot 295.

Longitudinal cavity 296 may facilitate various kinds of functionality for prosthesis 270. In some embodiments, longitudinal cavity 296 may be shaped and sized to receive a driven rod, pin, or similar component from a driven assembly and/or driving assembly. For example, the current embodiment illustrates a generally circular cross section for longitudinal cavity 296 and opening 299 in order to receive a generally cylindrical pin or rod that can apply a force directly to driving portion 274.

Longitudinal slot 295 may facilitate various kinds of functionality for prosthesis 270. In one embodiment, longitudinal slot 295 may facilitate the alignment of one or more suture threads along prosthesis 270. For example, in some embodiments a suture thread that is tied through hole 277 may extend within longitudinal slot 295 towards rearward portion 293 of base portion 290. An example of such an arrangement is described in detail below. This may allow for some protection of the suture thread as it is housed within a deployment device and/or during implantation into tissue and anchor expansion.

In some embodiments, base portion 290 and driving portion 274 may be attached at first connecting portion 310 and second connecting portion 398. In some embodiments, base portion 290 may be connected directly to wedge portion 278 of driving portion 274. In some embodiments, first longitudinal portion 291 and second longitudinal portion 292 may be connected to first wedge surface 279 and second wedge surface 280, respectively. In other embodiments, however, base portion 290 and driving portion 274 may not be attached, but instead may be held in relation to one another using a driving pin or similar component.

Some embodiments of prosthesis 270 may include provisions for grasping, gripping, or otherwise embedding prosthesis 270 into tissue such that prosthesis 270 resists removal from the tissue once inserted. In some embodiments, prosthesis 270 could include plurality of projecting portions 297 that extend from base portion 290. In some cases, plurality of projecting portions 297 may extend in a lateral direction to the implantation direction of prosthesis 270. For example, the present embodiments illustrate prosthesis 270 with five projecting portions 297. However, other embodiments could include any other number of projecting portions 297. For example, some other embodiments could include one, two, three, or more projecting portions.

Plurality of projecting portions 297 may include first projecting portion 298. In some embodiments, first projecting portion 298 may be representative of the remaining projecting portions in plurality of projecting portions 297. In the current embodiment, for example, each of plurality of projecting portions 297, including first projecting portion 298, may be substantially similar in geometry, size, and/or other characteristics. However, other embodiments could comprise two or more projecting portions that vary in geometry, size, and/or orientation. By varying the size, geometry, and/or orientation of two or more projecting portions, the anchoring properties of prosthesis 270 could be varied along the length of base portion 290.

In some cases, first projecting portion 298 comprises a first surface 302 and a second surface 304. First surface 302 may be oriented such that first surface 302 is approximately perpendicular to central axis 271 of prosthesis 270. In contrast, in some cases, second surface 304 may be oriented at an acute angle with respect to central axis 271. In some embodiments, second surface 304 slopes downwardly from the intersection of second surface 304 with first surface 302 towards forward portion 294 of base portion 290. In one embodiment, second surface 304 may be sloped in a manner to facilitate, or reduce resistance to, the insertion of prosthesis 270 into a tissue. In addition, first surface 302 may be oriented in a way that helps resist removal of prosthesis 270 from a tissue. This configuration helps to firmly anchor prosthesis 270 into place within a tissue.

Although the current embodiment illustrates a particular geometry for plurality of projecting portions 297, other embodiments could include any other kinds of structures that help to anchor prosthesis 270 into place following implantation. For example, in other embodiments, prosthesis 270 may include a plurality of barb-like projections. The shape, geometry, and/or other structural characteristics of projections extending from prosthesis 270 could vary according to various factors such as the type of tissue being repaired, the materials comprising prosthesis 270, as well as the method of implantation.

Some embodiments can include additional provisions for anchoring prosthesis 270 in place within bone or any other tissue. For example, some embodiments can include provisions that allow some portions of prosthesis 270 to expand as prosthesis 270 is implanted. In some embodiments, base portion 290 may be configured to expand as prosthesis 270 is implanted.

FIGS. 19 through 22 illustrate schematic side views of various configurations of prosthesis 270 during implantation into tissue 330. Tissue 330 is shown here as boney material. However, it should be understood that a similar process of implantation may occur within various other kinds of tissue, including both hard and soft tissues.

Some embodiments of a prosthesis may include provisions to help anchor the prosthesis within a tissue. In some embodiments, some portions of a prosthesis may be configured to expand once the prosthesis has been inserted into a tissue. In some embodiments, implanting a prosthesis may occur in two stages, including a first stage where the prosthesis is driven to a predetermined depth within the tissue and a second stage where at least one portion of the prosthesis expands.

Referring first to FIG. 19, prosthesis 270 may be aligned with the desired region of tissue 330 prior to implantation. In some embodiments, prosthesis 270 may be housed within deployment device 202 (not shown). However, in other embodiments, prosthesis 270 may be associated with any other device or tools for implanting prosthesis 270, including devices or tools that facilitate manual implantation. As previously discussed, in some embodiments a driven rod, pin, or similar component (not shown) may extend through longitudinal cavity 296 (see FIG. 17) of base portion 290. This allows an initial driving force to be applied directly to driving portion 274, as well as base portion 290. In other embodiments, however, the initial driving force could be applied directly to base portion 290 rather than driving portion 274. In still other embodiments, the initial driving force could be applied directly to driving portion 274 rather than base portion 290.

Referring next to FIG. 20, a first force 340 may be applied to prosthesis 270 at driving portion 274. In some embodiments, a second force 341 may simultaneously be applied to prosthesis 270 at rearward portion 293 of base portion 290. The result of first force 340 and second force 342 may be to drive prosthesis 270 into tissue 330. In some cases, first force 340 and second force 342 may act to drive prosthesis 270 to a depth D1 within tissue 330. In some cases, first force 340 and/or second force 342 may be selected to achieve a particular implantation depth. This depth can be chosen according to various factors including tissue structure, the type of repair being made, and the desired position of rearward portion 293 at the completion of the first stage of implantation. Note that while in some embodiments rearward portion 293 may extend outwardly from tissue 330 following this first stage of implantation, the final position of rearward portion 293 can change during a second stage of implantation as described below.

In some embodiments, a second stage of implantation occurs as first force 340 ceases (or is substantially reduced) while second force 342 continues to apply a driving force to base portion 290. During this second stage, driving portion 274 may remain substantially in place while base portion 290 is driven further into tissue 330 and simultaneously expands in the radial direction.

In some embodiments, first connecting portion 310 and second connecting portion 398 may be configured such that base portion 290 and driving portion 274 can separate under a predetermined amount of force, e.g., first connecting portion 310 and second connecting portion 398 may be separable. In some embodiments, the geometry and/or thickness of first connecting portion 310 and second connecting portion 398 can be controlled so that base portion 290 and driving portion 274 separate as a predetermined amount of force is applied. In other embodiments, the material composition of first connecting portion 310 and second connecting portion 398 could be selected to achieve separation of base portion 290 and driving portion 274 under the predetermined amount of force. During the first stage of implantation, the simultaneous application of first force 340 and second force 342 results in a substantially low net force in the region of first connecting portion 310 and second connecting portion 398. However, in the second stage of implantation, the decrease in first force 340 creates a net force in the region of first connecting portion 310 and second connecting portion 398, which may act to deform and eventually separate first connecting portion 310 and second connecting portion 398.

Referring to FIG. 21, second force 342 is applied at rearward portion 293 of base portion 290. The magnitude of second force 342 may be such that base portion 290 separates from driving portion 274 at first connecting portion 310 and second connecting portion 398. With base portion 290 separated, second force 342 acts to push forward portion 294 against wedge portion 278. As seen here, wedge portion 278 may drive into forward portion 294, which has the effect of driving first longitudinal portion 291 and second longitudinal portion 292 apart at forward portion 294.

In some embodiments, base portion 290 is driven further into tissue 330 under the continued application of second force 342. As base portion 290 continues to penetrate farther into tissue 330, driving portion 274, which remains approximately stationary within tissue 330, acts to further separate first longitudinal portion 291 and second longitudinal portion 292, as shown in FIG. 22.

Referring to FIG. 23, the end of the second stage of implantation may occur when wedge portion 278 is disposed directly adjacent to rearward portion 293 of base portion 290. In some cases, as seen in FIG. 23, rearward portion 293 may be recessed with respect to outer surface 331 of tissue 330. In other cases, rearward portion 293 may be approximately flush with outer surface 331. In still other cases, rearward portion 293 may extend outwardly from outer surface 331. The depth of rearward portion 293 relative to outer surface 331 may vary in different embodiments according to various factors such as the type of tissue, the magnitude of the forces applied to the prosthesis, the condition of the patient, the method of repair, the surgeon's preference, as well as the geometry and material composition of the prosthesis. Moreover, these various factors may be tuned in order to achieve a desired implantation depth.

The configuration of prosthesis 270 following the first and second stages of implantation helps anchor prosthesis 270 within tissue 330. Any suture placed within hole 277 could extend along base portion 290 and apply tension along an outward direction from tissue 330. The splayed configuration of first longitudinal portion 291 and second longitudinal portion 292 may help resist outward movement of prosthesis 270. In some cases, plurality of projecting portions 297 (FIG. 17) may further help to secure prosthesis 270 within tissue 330. In particular, each of the projecting portions may generally project outwardly from base portion 290 to increase the resistance of base portion 290 to being removed.

Some embodiments may include provisions for helping to ensure a prosthesis expands properly during implantation. In some embodiments, a prosthesis may be provided with provisions that help to maintain axial alignment of driving portion 274 and base portion 290, which may facilitate proper engagement between base portion 290 and wedge portion 278 as discussed in further detail below. Referring back to FIG. 17, in one example, wedge portion 278 may include first projecting feature 301 and second projecting feature 303, which extend from first wedge surface 279 and second wedge surface 280, respectively. Moreover, base portion 290 may comprise corresponding track-like features along interior surface 399. In some embodiments, first projecting feature 301 and second projecting feature 303 have convex rounded cross-sectional shapes that correspond with the concave cross-sectional shapes of interior surface 399 of base portion 290. Thus, as first wedge surface 279 and second wedge surface 280 engage base portion 290 and begin splitting first longitudinal portion 291 and second longitudinal portion 292 apart, first projecting feature 301 and second projecting feature 303 may enter corresponding tracks or channels along interior surface 399 of base portion 290. This may help to maintain the desired axial alignment between driving portion 274 and base portion 290 throughout implantation.

In some embodiments, driving portion 274 and base portion 290 may include cooperating features to help resist back-out, or any tendency for base portion 290 to move rearwardly away from driving portion 274. In particular, these features may help lock driving portion 274 and base portion 290 together at various stages of implantation and especially once prosthesis 270 has been fully implanted (i.e. base portion has fully expanded). In some embodiments, wedge portion 278 could be configured with surface features that engage corresponding recesses or notches in base portion 290 in order to restrict any tendency of base portion 290 to back away from driving portion 274, as well as to lock driving portion 274 and base portion 290 together at the end of the implantation process. Some embodiments could include notches within base portion 290 that receive corresponding features or protrusions on driving portion 274 in order to resist rearward motion of base portion 290 during implantation. Examples of various cooperating or corresponding surfaces and/or surface features may include, but are not limited to, protrusions that engage corresponding recesses, corresponding ridged surfaces, corresponding teeth, as well as any other features. In some embodiments, this arrangement may have the effect of preventing driving portion 274 from moving further into tissue 330 (see FIG. 23). Additionally, this arrangement may also help prevent base portion 290 from moving in a direction opposite of implantation.

In one embodiment, as seen in FIG. 17 and FIG. 19, prosthesis 270 may comprise first barbed portion 391 and second barbed portion 393 that are disposed on driving portion 274. In some embodiments, first barbed portion 391 and second barbed portion 393 may be configured to engage plurality of notch-like portions 395 that are disposed on interior surfaces of plurality of projecting portions 297. As shown in FIGS. 21 through 23, as prosthesis 270 expands, first barbed portion 391 and second barbed portion 393 may engage notch-like portions 395 of rearward portion 293 of base portion 290.

In some embodiments, the features described here may work together to help prosthesis 270 to expand in the desired manner during implantation. For example, as prosthesis 270 begins to expand, first projecting feature 301 and second projecting feature 303 may engage corresponding tracks or grooves of interior surface 399 of base portion 290 in order to guide and prevent the separation of driving portion 274 and base portion 290 and maintain the desired axial alignment. Simultaneously, as base portion 290 expands, first barbed portion 391 and second barbed portion 393 engage notch-like portions 395 within base portion 290, which prevents relative movement and back-out and helps ensure that driving portion 274 and base portion 290 do not move apart along the axial direction. Moreover, these features work together to lock prosthesis 270 in a fully expanded position once the implantation process is complete.

Figure 24:
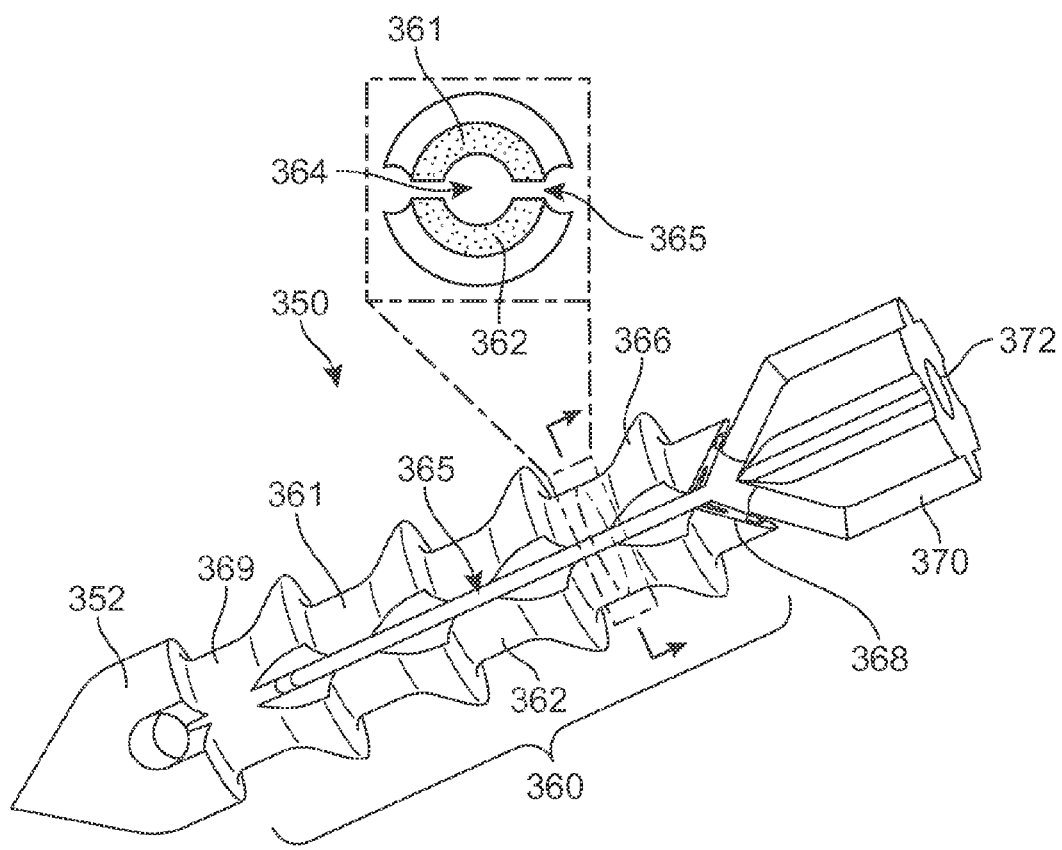
FIG. 24 is a schematic diagram illustrating an isometric view of another embodiment of a prosthesis.

FIG. 24 illustrates an isometric view of an alternative embodiment of a prosthesis 350. Prosthesis 350 could share some similar characteristics with prosthesis 270 described above. For example, prosthesis 350 may include a driving portion 352 and a base portion 360. Moreover, base portion 360 can be divided into a first longitudinal portion 361 and a second longitudinal portion 362 that are separated by longitudinal cavity 364 as well as longitudinal slot 365. In some embodiments, base portion 360 may also include plurality of ridged portions 366.

In contrast to the previous embodiment, however, the embodiment shown in FIG. 24 includes a separate wedge portion 370. In some embodiments, wedge portion 370 and driving portion 352 may be disposed on opposing end portions of base portion 360. In addition, first longitudinal portion 361 and second longitudinal portion 362 are separated at rearward portion 368, which is disposed adjacent to wedge portion 370. Also, first longitudinal portion 361 and second longitudinal portion 362 may be connected at forward portion 369, which is disposed adjacent to driving portion 352.

In some embodiments, wedge portion 370 can include one or more channels or holes. In some embodiments, wedge portion 370 can include hole 372 that extends through the entirety of wedge portion 370. In some embodiments, hole 372 may be aligned with longitudinal cavity 364 of base portion 360. In one embodiment, hole 372 and longitudinal cavity 364 may be configured to receive a rod, pin, or similar device that can be inserted through base portion 360. This allows a force to be applied directly to forward portion 369 of base portion 360, which is adjacent to driving portion 352.

FIGS. 25 through 28 illustrate schematic side views of several configurations of prosthesis 350 during implantation into tissue 380. As with the previous embodiment, the process of implanting prosthesis 350 may generally occur in two stages. During a first stage, prosthesis 350 may be driven to a predetermined depth D2 into tissue 380 (as seen in FIG. 26). Following this, during a second stage, base portion 360 of prosthesis 350 may undergo expansion within tissue 380 (as seen in FIGS. 27 and 28).

Referring to FIG. 25, prior to implantation, prosthesis 350 may be aligned with the desired region of tissue 380. Next, as seen in FIG. 26, a first force 390 may be applied to forward portion 369. In some embodiments, a second force 392 may be simultaneously applied to wedge portion 370. The application of first force 390 and second force 392 may help to drive prosthesis 350 into tissue 380. This comprises the first stage of implantation in which driving portion 352 is inserted to a depth D2.

As seen in FIG. 27, the second stage of implantation begins as first force 390 ceases or substantially decreases in magnitude while second force 392 continues to be applied to wedge portion 370. At this point, the magnitude of second force 392 may be such that wedge portion 370 separates from base portion 360. Once separated from base portion 360, wedge portion 370 may be driven into rearward portion 368. Moreover, as shown in FIG. 27, wedge portion 370 acts to separate first longitudinal portion 361 and second longitudinal portion 362 of base portion 360. Finally, as seen in FIG. 28, wedge portion 370 may be disposed adjacent to driving portion 352 after the implantation process has been completed.

The configuration of prosthesis 350 following the first and second stages of implantation helps anchor prosthesis 350 within tissue 380. Any suture secured at driving portion 352 could extend around wedge portion 370 and apply tension along an outward direction from tissue 380. The splayed configuration of first longitudinal portion 361 and second longitudinal portion 362 helps resist outward movement of prosthesis 350. In some embodiments, plurality of ridged portions 366 may further help to secure prosthesis 350 within tissue 380.

As described earlier, some embodiments of a prosthesis can include portions that have corresponding or cooperating surfaces (including both textures and/or other surface features). In the embodiments shown in FIGS. 24 through 28, wedge portion 370 and base portion 360 may be configured with cooperating surface textures or features in order to reduce or substantially eliminate movement that may otherwise separate wedge portion 370 and base portion 360 both during and after implantation. Examples of various cooperating or corresponding surfaces and/or surface features may include, but are not limited to, protrusions that engage corresponding recesses, corresponding ridged surfaces, corresponding teeth, track-like features, as well as any other features. In some embodiments, for example, wedge portion 370 includes surface textures or features that cooperate with corresponding textures or features of an interior surface of longitudinal cavity 364. Therefore, as wedge portion 370 drives into base portion 360 and acts to expand or splay base portion 360, surface features of wedge portion 370 may engage surface features of the interior surface of longitudinal cavity 364 to help prevent wedge portion 370 from axial misalignment with base portion 360 during or after implantation. In particular, these provisions help resist movement in a direction opposite of implantation, once prosthesis 350 has been fully implanted.

The prostheses of the above described embodiments (including the embodiments shown in FIGS. 17 through 23 as well as the embodiments shown in FIGS. 24 through 28) are configured to split, or splay, into two portions. In other embodiments, a prosthesis could be configured to split into three or more portions. In some embodiments, for example, the base portion of a prosthesis could be configured as three or more distinct portions that are separated by various slots as well as a longitudinal cavity.

Figure 29:
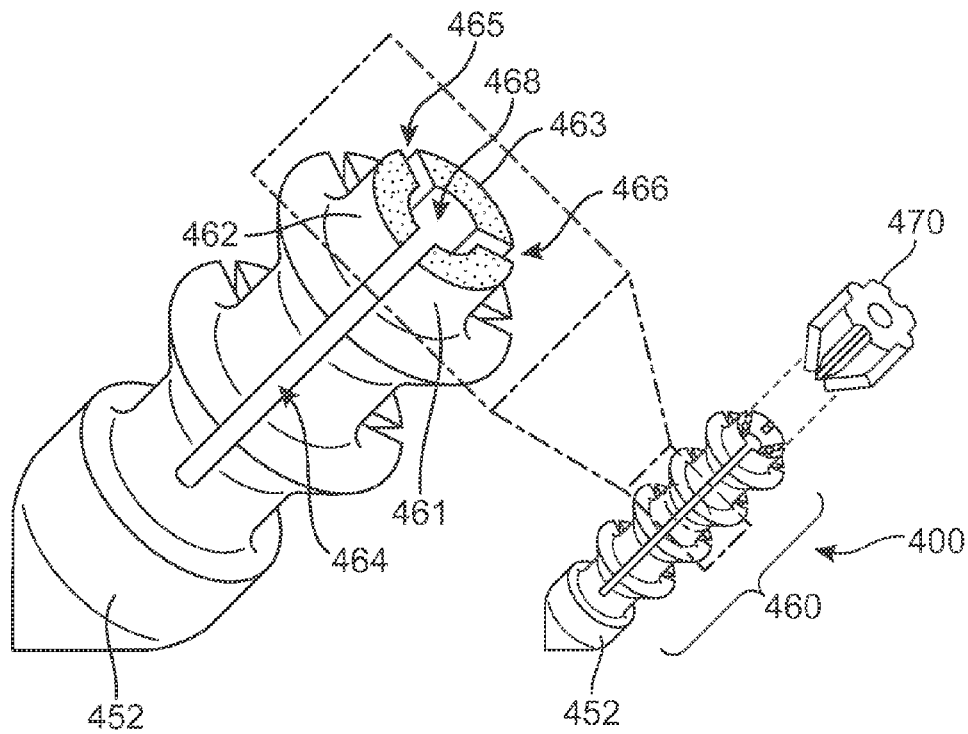
FIG. 29 is a schematic diagram illustrating an isometric view of an embodiment of a prosthesis including three separated portions as well as an enlarged cut-away view of the prosthesis.
Figure 30:
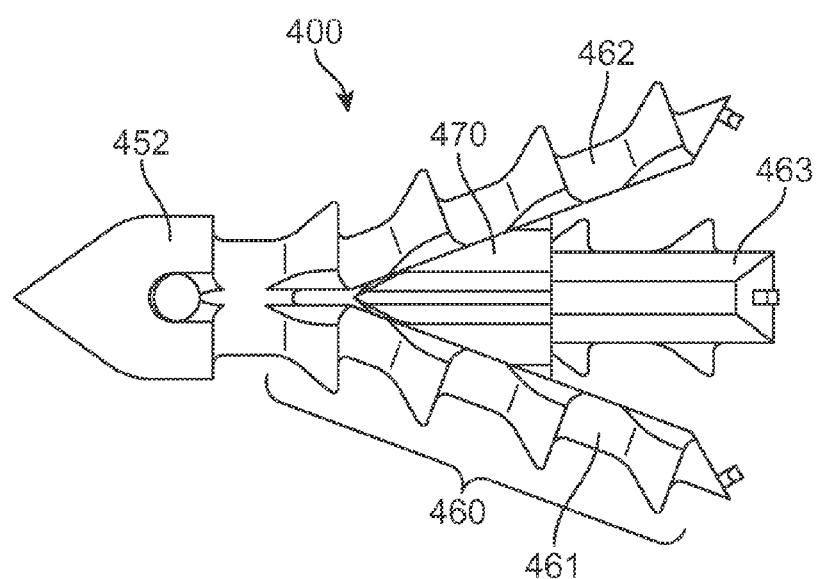
FIG. 30 is a schematic diagram illustrating a side view of an embodiment of the prosthesis of FIG. 29 split into three portions.

FIGS. 29 and 30 illustrate schematic views of an embodiment of a prosthesis 400 that is configured to separate into three distinct portions under a predetermined force. In particular, FIG. 29 illustrates a schematic isometric view of prosthesis 400 including an enlarged cut-away view. FIG. 30 illustrates a schematic view of prosthesis 400 where base portion 460 has been expanded. Referring to FIGS. 29 and 30, prosthesis 400 may share some similar characteristics with prosthesis 350 described above. For example, prosthesis 400 may include a driving portion 452 and a base portion 460. For purposes of clarity, only some of the shared features between prosthesis 400 and prosthesis 350 are described here.

In the current embodiment, base portion 460 comprises three distinct portions. Specifically, in this case, base portion 460 comprises first longitudinal portion 461, second longitudinal portion 462, and third longitudinal portion 463. First longitudinal portion 461, second longitudinal portion 462, and third longitudinal portion 463 may be separated by first longitudinal slot 464, second longitudinal slot 465, and third longitudinal slot 466, as well as longitudinal cavity 468.

As shown in FIG. 30, first longitudinal portion 461, second longitudinal portion 462, and third longitudinal portion 463 may each be configured to expand, or splay, outwardly. In some embodiments, the splaying of first longitudinal portion 461, second longitudinal portion 462, and third longitudinal portion 463 occurs as splitting member 470 is driven into base portion 460. Splitting member 470 could be similar in some respects to wedge portion 370 of the previous embodiment. In some embodiments, splitting member 470 may be configured with a geometry to apply approximately equal outward forces against first longitudinal portion 461, second longitudinal portion 462, and third longitudinal portion 463.

FIG. 31 illustrates schematic cut-away views of two more alternative embodiments of prostheses with expandable base portions. Referring to FIG. 31, prosthesis 430 is configured with four distinct portions that may split apart from one another during implantation. Prosthesis 440 is configured with five distinct portions that may split apart during implantation. Moreover, prosthesis 430 and prosthesis 440 are only shown as further possible embodiments. Additional embodiments are not limited to any particular number of distinct portions and could include, for example, six separate portions, seven separate portions, or any other number of portions. It should be understood that the number of portions of a prosthesis that may be pre-configured to split apart as the prosthesis is implanted may depend on a variety of factors including geometry and material of the prosthesis, the method of repair employed by the surgeon, as well as the type of tissue into which a prosthesis may be deployed. Furthermore, while the embodiments described above include portions that are generally arranged in a symmetric manner about a central axis of the prosthesis, other embodiments could incorporate portions that are arranged in an asymmetric manner about a central axis.

In different embodiments, the size, shape, and other characteristics of a prosthesis may vary. Generally, the size, shape, and other characteristics could be determined based on a number of factors. These factors may potentially include the size and shape of the corresponding imperfection; the condition and type of tissue into which the prosthesis is to be deployed; the type and amount of stress that is to be exerted by the prosthesis on the surrounding tissue; and the method of repair employed by the surgeon.

The prostheses described above and shown in the figures may be made of a variety of materials. In some cases, a prosthesis may be made using a biocompatible material that is sufficiently rigid to anchor a suture for repairing tendons, yet sufficiently compliant so as to avoid further damaging the tendon should slight relative motion between the tendon (or adjacent tissue) and the prosthesis occur. Examples of suitable materials include polymers such as nylon, prolene, dacron, ultra high molecular weight polyethylene (UHMWPE), and other suitable materials. Some examples of suitable bioabsorbable materials are: poly L-lactic acid (PLLA), polyglycolic acid (PGA). A prosthesis can also be formed of other possible materials, including polymers and metals such as polytetrafluorethylene (PTFE), polyaryletherketone (PAEK), polyetheretherketone (PEEK), polyoxymethylene (acetal), polycarbonate, polysulfone, silicone elastomers, commercially pure titanium, titanium alloys, CoCr alloys, nickel titanium (nitinol) alloys, and implant grade stainless steels. In some embodiments, a prosthesis may be formed of a bioabsorbable polymer that is gradually absorbed by the body. Still other possible materials for a prosthesis include composites, such as carbon fiber composites and ceramics. It will be understood that the materials used for a prosthesis are not limited and a variety of different materials could be used according to desired characteristics for the prosthesis.

Prostheses including multiple longitudinal portions can be manufactured as single monolithic parts in some cases. For example, some embodiments may include prostheses comprising a substantially monolithic material, such as a bioabsorbable polymer that may be molded to the desired shape. In still other embodiments, however, longitudinal portions of a prosthesis could be formed separately and joined in a later stage of manufacturing.

Impact System

A surgeon may install one or more prostheses during a surgical procedure to repair damaged or otherwise imperfect tissue by manually inserting the one or more prostheses, with or without the help of additional tools. As previously discussed, however, a deployment device may also be used to install one or more prostheses.

Figure 32:
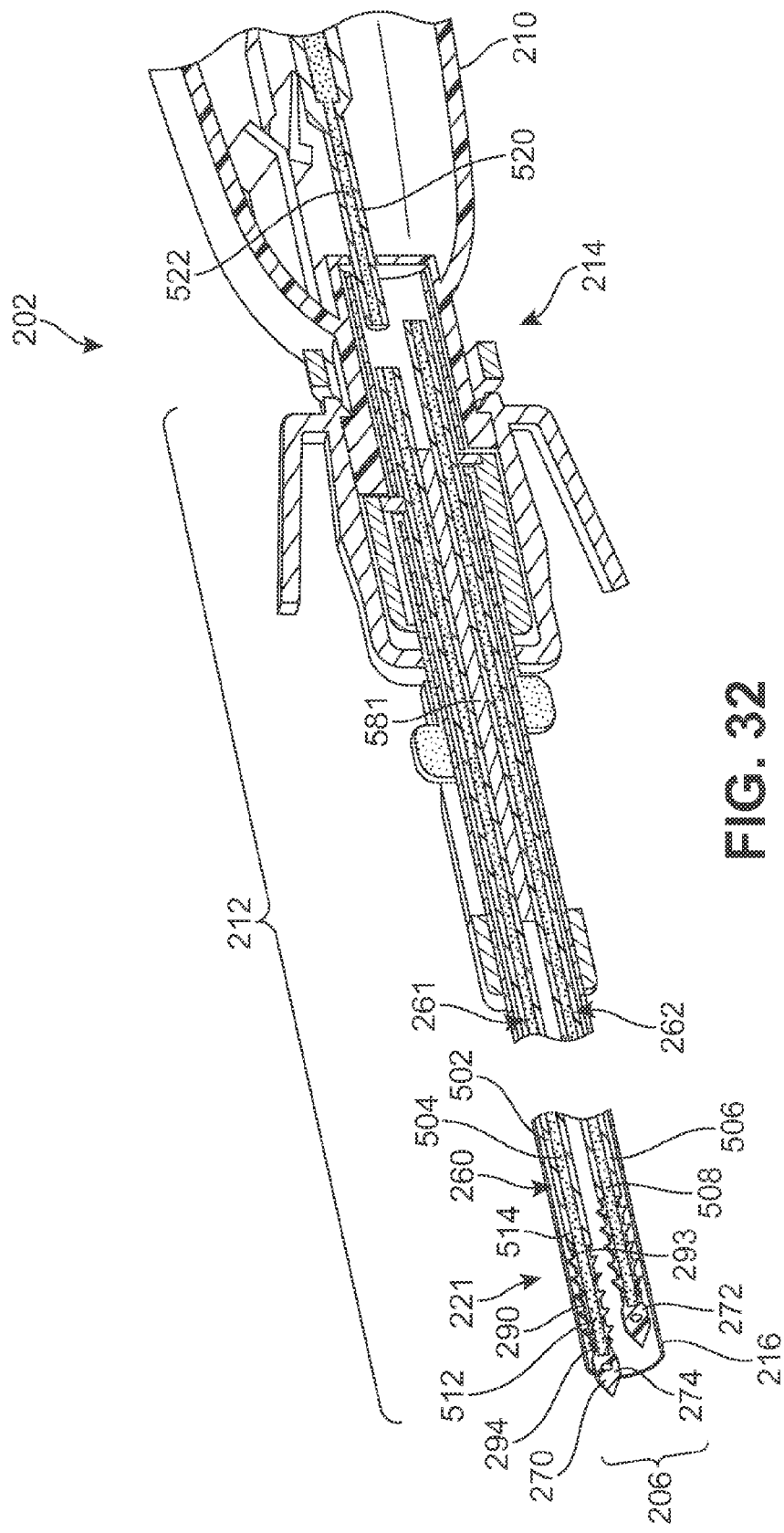
FIG. 32 is a schematic diagram illustrating an isometric cut-away view of portions of a front delivery assembly according to an embodiment.
Figure 33:
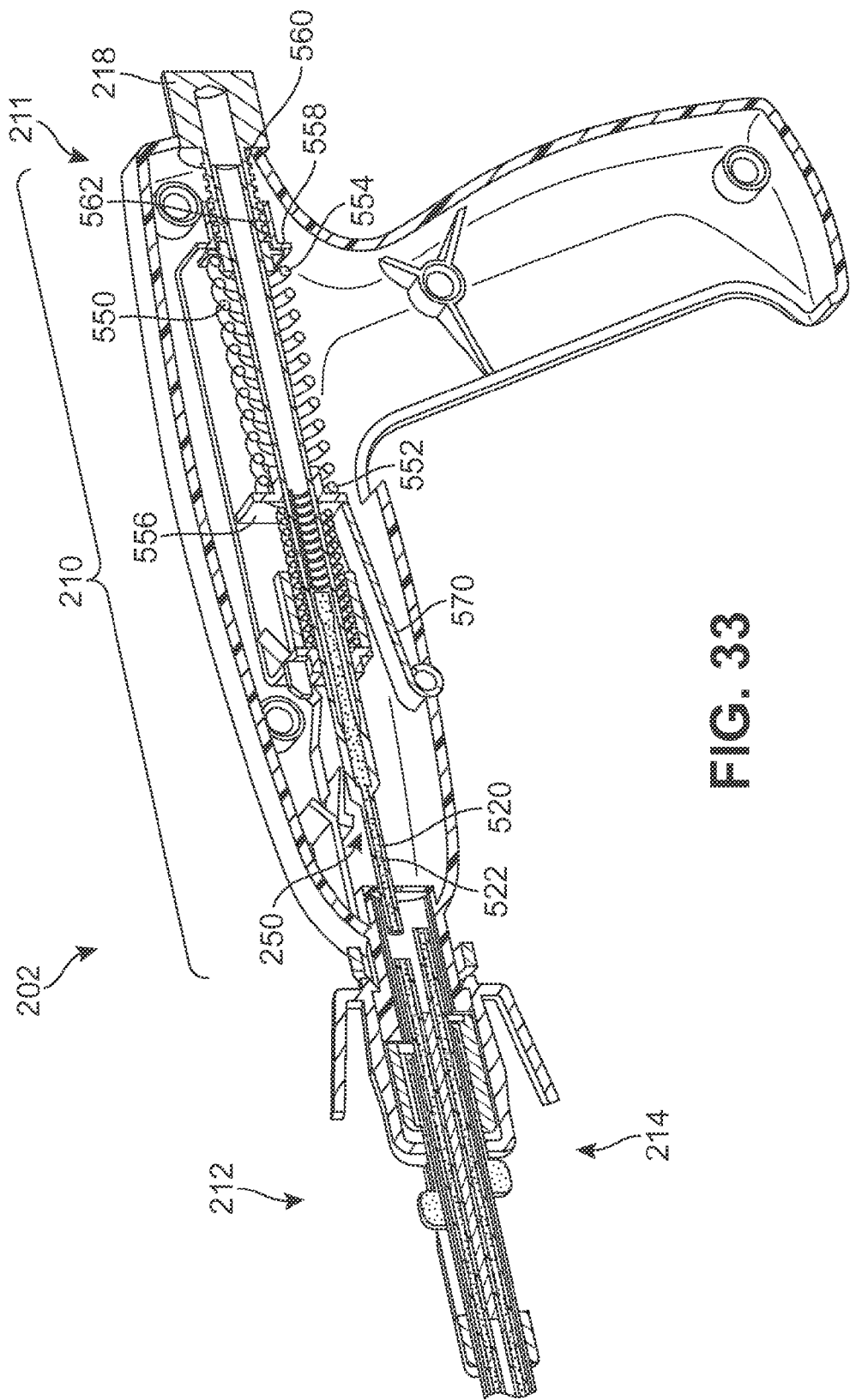
FIG. 33 is a schematic diagram illustrating an isometric cut-away view of an embodiment of a portion of a deployment device including views of components internal to a base assembly.

FIGS. 32 and 33 illustrate isometric cut-away views of deployment device 202 according to one embodiment. In particular, FIG. 32 illustrates an isometric cut-away view of forward end portion 221 of front delivery assembly 212 as well as the rearward end portion 214 of front delivery assembly 212. FIG. 33 illustrates an isometric cut-away view of a portion of deployment device 202 including base assembly 210 and rearward end portion 214 of front delivery assembly 212.

Referring first to FIG. 32, components of base assembly 210 and front delivery assembly 212 may cooperate to implant one or more prostheses. As described earlier and shown in FIGS. 19 through 23, first prosthesis 270 may be implanted into tissue through a two stage implantation process. During a first stage a first force may be applied directly to driving portion 274 and base portion 290 of prosthesis 270 to drive first prosthesis 270 to a predetermined depth within a tissue. During a second stage a force may be applied only to base portion 290 of prosthesis 270 in order to expand base portion 290 within the tissue. To accommodate this two stage process, deployment device 202 can incorporate a two stage impact and driving mechanism to implant first prosthesis 270. This two stage impact and driving mechanism may similarly be used to implant second prosthesis 272.

In some embodiments, plurality of prostheses 206 may be associated with components of plurality of driven assemblies 260. In some embodiments, first prosthesis 270 may be associated with first driven tube 502 and first driven pin 504. First driven pin 504 may be coaxially located within a hollow longitudinal cavity 510 (see FIG. 34) of first driven tube 502. In some embodiments, first driven pin 504 may be capable of translating through hollow longitudinal cavity 510 of first driven tube 502.

In some embodiments, first prosthesis 270 may be associated with end portions of first driven tube 502 and first driven pin 504. In some embodiments, first end portion 512 (see FIG. 32) of first driven pin 504 may be inserted into longitudinal cavity 296 (see FIG. 17) of first prosthesis 270. In some cases, first end portion 512 may further be disposed adjacent to driving portion 274, which may allow first driven pin 504 (FIG. 32) to apply a force directly to driving portion 274 during implantation. Additionally, in some embodiments, first end portion 514 of first driven tube 502 may be disposed adjacent to rearward portion 293 of base portion 290. This arrangement may allow first driven tube 502 to apply a force directly to base portion 290 during implantation.

Referring to FIG. 32, in some embodiments, second prosthesis 272 may likewise be associated with second driven tube 506 and second driven pin 508. In some cases, the arrangement of second prosthesis 272 with second driven tube 506 and second driven pin 508 may be substantially similar to the relationship described above between first prosthesis 270, first driven tube 502 and first driven pin 504. In some embodiments, for example, second driven tube 506 may include a hollow longitudinal cavity through which second driven pin 508 may translate. For purposes of reference, first driven tube 502 and first driven pin 504 may be collectively referred to as first driven assembly 261 while second drive tube 506 and second driven pin 508 may be collectively referred to as second driven assembly 262.

First prosthesis 270 may or may not be joined with first driven tube 502 and/or first driven pin 504. In some embodiments, for example, first driven pin 504 may simply be inserted within first prosthesis 270, without being directly attached. In some embodiments, a frictional fit could be formed between first driven pin 504 and first prosthesis 270. Likewise, in some embodiments, first driven tube 502 could be disposed adjacent to, but not joined with, first prosthesis 270. In other embodiments, first prosthesis 270 could be temporarily joined with first driven pin 504 and/or first driven tube 502. Various joining methods could be used including, but not limited to, adhesives and mechanical connectors. Further examples of provisions for joining first prosthesis 270 with first driven pin 504 and/or first drive tube 502 include, but are not limited to: ridges, annular rings, frictional fits and threading. For example, in some embodiments, a driven pin and a prosthesis could have corresponding threaded portions, which could allow the driven pin to be screwed into the prosthesis. It will be understood that in embodiments where first prosthesis 270 may be attached to first driven tube 502 and/or first driven pin 504, this attachment could be temporary and these components may be easily and/or automatically separated during the implantation process so that only first prosthesis 270 remains implanted in the tissue. The specific provisions used for retaining the prosthesis on the driven pin can vary and in different embodiments could be selected according to: materials of the pin and/or prosthesis; type of tissue into which the prosthesis is to be implanted as well as possibly other factors.

As seen in FIG. 32, some embodiments of front delivery assembly 212 may include guide member 581. In some embodiments, guide member 581 is configured to control the alignment of first driven tube 502, first driven pin 504, second driven tube 506 and second driven pin 508. Moreover, in some cases, guide member 581 is configured with a groove for receiving one or more o-rings. One or more o-rings may be used to seal out fluids and may also provide sufficient friction to maintain axial advancement of each driven tube during impact with driving tube 520.

The following discussion makes reference to the implantation of first prosthesis 270 using first driven tube 502 and first driven pin 504, in combination with other components of deployment device 202. However, it should be understood that the discussion may equally apply to the implantation of second prosthesis 272. As discussed later, the locations of second prosthesis 272, second driven tube 506 and second driven pin 508 within front delivery assembly 212 can be interchanged with first prosthesis 270, first driven tube 502, and first driven pin 504, respectively. Therefore, the operation of implanting second prosthesis 272 may be substantially similar to the operation of implanting first prosthesis 270. Moreover, in some embodiments, the process of implanting first prosthesis 270 and second prosthesis 272 makes use of the same components within base assembly 210 for impacting and driving the associated driven pin and driven tube.

Using the arrangement described here for first prosthesis 270, base assembly 210 can include provisions for applying the desired forces to first driven tube 502 and first driven pin 504. Specifically, in some cases, base assembly 210 may be configured to deliver at least two forces of possibly varying magnitudes and in a predetermined sequence that coincide with the two stage implantation of first prosthesis 270. In some embodiments, this is accomplished using a driving tube 520 and driving pin 522 that generally comprise portions of the driving assembly 250 mentioned earlier. Driving tube 520 and driving pin 522 may be aligned with first driven tube 502 and first driven pin 504, respectively. In some embodiments, driving pin 522 may be coaxially located within a hollow longitudinal cavity 526 (see FIG. 35) of driving tube 520. Driving pin 522 may be capable of translating through hollow longitudinal cavity 526 of driving tube 520.

In different embodiments, the relative movement of driving tube 520 and driving pin 522 could vary. In some embodiments, driving tube 520 may move independently of driving pin 522. In other embodiments, however, driving tube 520 and driving pin 522 may be configured to move together. In one embodiment, driving tube 520 and driving pin 522 may move together during some stages of implantation and may move independently during other stages of implantation. For example, during some stages of implantation driving pin 522 may remain approximately stationary with respect to base assembly 210, while driving tube 520 is in motion. As an alternative example, during some stages of implantation driving tube 520 may remain approximately stationary with respect to base assembly 210, while driving pin 522 is in motion.

Referring now to FIG. 33, base assembly 210 may include provisions that control the driving motions of driving tube 520 and driving pin 522, including the relative motions between driving tube 520 and driving pin 522. These motions are generally initiated and controlled by various other components including components for storing energy, components for releasing the stored energy and components for transforming the released energy into a particular sequence of motions accomplished by driving tube 520 and driving pin 522.

The following discussion describes one possible configuration of base assembly 210 that may facilitate the actuation of driving tube 520 and driving pin 522. In some embodiments, some of the following components are optional and could be omitted. In other embodiments, additional components not shown or described here may be added. Moreover, it should be understood that the particular components used to initiate actuation, store energy, and/or control the resulting movement of driving assembly 250 could vary in other embodiments.

Base assembly 210 can include provisions for storing energy. In some embodiments, energy could be stored using one or more springs. In one embodiment, base assembly 210 includes impact spring 550. Generally, impact spring 550 could be any type of spring including, for example, a tension spring, a torsion spring, wave spring, and/or a compression spring. In one embodiment, impact spring 550 is a compression spring that stores mechanical energy.

Impact spring 550 may include first end portion 552 and second end portion 554. In some cases, first end portion 552 may be disposed adjacent to impact collar 556 that generally translates with first end portion 552. In some cases, second end portion 554 may be disposed adjacent to rear bushing 558. As discussed below, the absolute positions of impact collar 556 and rear bushing 558 within base assembly 210 can be made to vary.

In some embodiments, impact spring 550 is associated with various additional components that facilitate the storage of energy in, and the release of energy from, impact spring 550. The compression and/or extension of impact spring 550 occurs when the relative distance between impact collar 556 and rear bushing 558, which are generally associated with the positions of first end portion 552 and second end portion 554, varies. In some cases, the absolute position of rear bushing 558 within base assembly 210 can be controlled using control knob 218 in order to adjust the force. In some cases, for example, a threaded portion 560 of control knob 218 engages a thread receiving portion 562 of rear bushing 558. As control knob 218 is turned, the position of rear bushing 558 can be moved towards or away from impact collar 556, which adjusts the force that is applied to one or more prostheses.

In some embodiments, the absolute position of impact collar 556 may depend on several components, including positioning ram 570. In some cases, as positioning ram 570 is moved towards rearward portion 211 of base assembly 210, impact collar 556 also translates rearwardly. This causes impact spring 550 to compress and store mechanical energy.

In some embodiments, impact collar 556 may be connected to driving tube 520. As seen in FIG. 33, driving tube 520 may generally extend rearwardly through base assembly 210 and may terminate within rearward portion 211. Therefore, as impact collar 556 is translated within base assembly 210 (for example, by manipulating positioning ram 570 and/or under the forces of impact spring 550) driving tube 520 may be similarly translated with respect to base assembly 210. Furthermore, as described in detail below, loading impact spring 550 and releasing impact spring 550 generates an impacting force at impact collar 556, which is translated to an impacting force within driving tube 520.

A deployment device can include provisions for retaining an impact spring and associated components of a driving assembly. In some embodiments, a deployment device can be configured with a brace member that houses an impact spring as well as a return spring. The brace member may help to retain the driving assembly relative to a base assembly. In some embodiments, the brace member may be made of a substantially rigid material, such as metal, in order to help limit plastic deformation.

Figure 34:
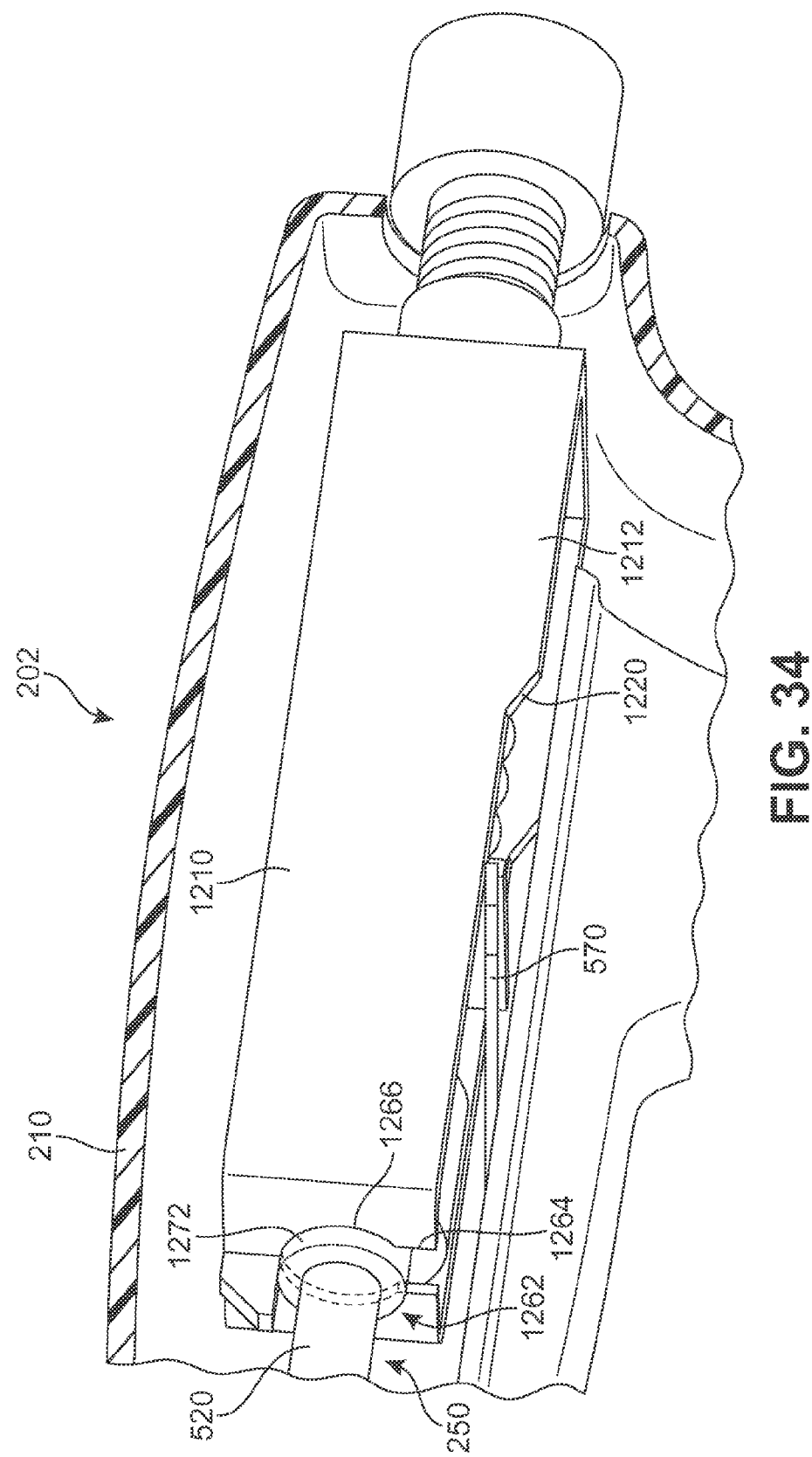
FIG. 34 is a schematic diagram illustrating an isometric cut away view of a portion of a deployment device including a brace member.

FIG. 34 illustrates a schematic isometric view of an embodiment of a portion of deployment device 202. Referring to FIG. 34, brace member 1210 comprises a rectangular box-like structure that includes vertical sidewalls and which is substantially open at its upper and lower surfaces. As seen in FIG. 34, positioning ram 570 is configured to rest against lower peripheral edge 1212 of brace member 1210. Moreover, brace member 1210 may be fixed within base assembly 210 through one or more fastening means (not shown).

Referring to FIG. 34, brace member 1210 may include slot 1262 that is disposed at a forward end of brace member 1210. Slot 1262 may include a peripheral slot portion 1264 and a central hole slot portion 1266. In some cases, central hole slot portion 1266 has an approximately circular shape and is configured to receive a portion of front bushing 1272.

In addition, peripheral slot portion 1264 connects central hole slot portion 1266 with lower peripheral edge 1212 and generally has a width that is substantially less than the diameter of central hole slot portion 1266.

In some embodiments, slot 1262 provides a way of assembling driving assembly 250 with brace member 1210. In particular, driving tube 520, which extends throughout the length of base assembly 210, may fit through peripheral slot portion 1264. Once driving tube 520 is disposed within central hole slot portion 1266, front bushing 1272 may be pushed into place through central hole slot portion 1266. Front bushing 1272 may be sized so that it is too large to slide down through peripheral slot portion 1264. Furthermore, the tension provided by impact spring 550 (see FIG. 33) and return spring 815 (see FIG. 43) provides a restraining force that prevents front bushing 1272 from backing out of central hole slot portion 1266 and thereby helps retain driving tube 520 within brace member 1210.

Figure 35:
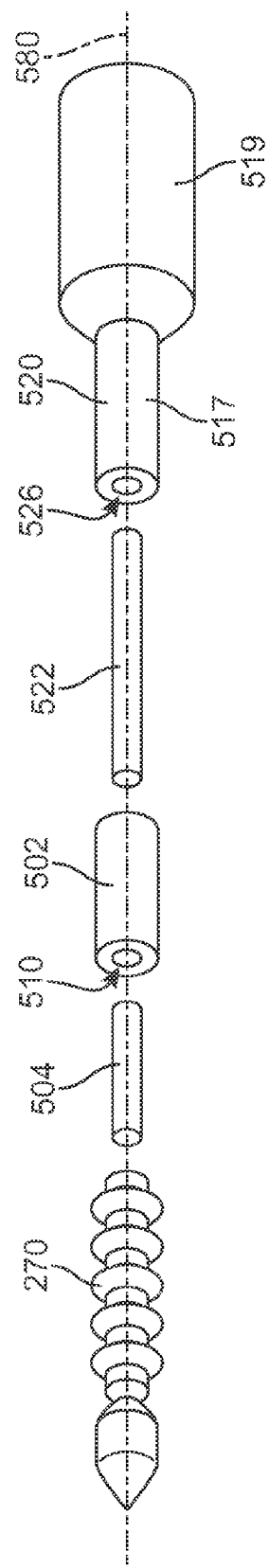
FIG. 35 is a schematic diagram illustrating an isometric view of an embodiment of the coaxial alignment of several components of a tissue repair system.

FIG. 35 illustrates a schematic view of an embodiment of some components of driving assembly 250 (see FIG. 33), plurality of driven assemblies 260 (see FIG. 32), and prosthesis 270. For purposes of illustrating the general arrangement of these components, the components of driving assembly 250 and plurality of driven assemblies 260 are shown schematically. For example, the general dimensions of the components, including length and thickness, have been modified to clearly illustrate the relative positions and orientations of the components to one another.

Referring to FIG. 35, each of prosthesis 270, first driven tube 502, first driven pin 504, first driving tube 520, and first driving pin 522 may be approximately aligned along axis 580. Moreover, the general arrangement of these components may be such that first driven pin 504 is disposed coaxially within first driven tube 502 and driving pin 522 is disposed coaxially within driving tube 520. In particular, first driven pin 504 may be disposed within hollow longitudinal cavity 510 of first driven tube 502. Likewise, driving pin 522 may be disposed within hollow longitudinal cavity 526 of driving tube 520. This coaxial arrangement for first driven tube 502 and first driven pin 504 may facilitate the two stage implantation process required to properly install prosthesis 270 into tissue. Additionally, the coaxial arrangement for driving tube 520 and driving pin 522 may ensure that first driven tube 502 and first driven pin 504 are properly actuated during the implantation of prosthesis 270.

In some embodiments, driving assembly 250 and plurality of driven assemblies 260 may be configured such that driving tube 520 can interact directly with first driven tube 502, but not with first driven pin 504. Likewise, in some cases, driving pin 522 may be configured to interact directly with first driven pin 504, but not with first driven tube 502. This allows a configuration in which driving tube 520 applies a driving force directly to first driven tube 502, while driving pin 522 applies a driving force directly to first driven pin 504. Moreover, it is possible for driving tube 520 to pass over first driven pin 504 without affecting the motion of first driven pin 504. In some embodiments, therefore, the dimensions of first driven pin 504 and driving pin 522 may be selected so that first driven pin 504 and driving pin 522 have substantially similar diameters. Then, as first driven pin 504 and driving pin 522 are aligned along the same axis 580, driving pin 522 can engage driven pin 504 without also engaging first driven tube 502. Likewise, in some embodiments, the dimensions of first driven tube 502 and a portion of driving tube 520 may be selected so that first driven tube 502 and driving tube have substantially similar cross-sectional dimensions. In some embodiments, driving tube 520 includes a forward portion 517 and a rearward portion 519 that have substantially different diameters. In one embodiment, for example, first driven tube 502 and forward portion 517 of driving tube 520 may have substantially similar inner diameters and outer diameters that characterize the corresponding ring-like cross-sectional shapes of both tubes. This allows driving tube 520 to engage first driven tube 502 without also engaging first driven pin 504.

FIGS. 36 through 40 illustrate schematic side views of a method of implanting prosthesis 270 into tissue 600 according to one embodiment. For purposes of clarifying the operation of plurality of driven assemblies 260 (see FIG. 32) and driving assembly 250 (see FIG. 33) during implantation, prosthesis 270, first driven pin 504, first driven tube 502, first driving pin 522, and first driving tube 520 are shown here in isolation, without any other components of deployment device 202 (see FIG. 32). Moreover, as discussed above with reference to FIG. 35, these figures are not intended to accurately represent dimensions including, for example, length and width, of the components.

Figure 36:
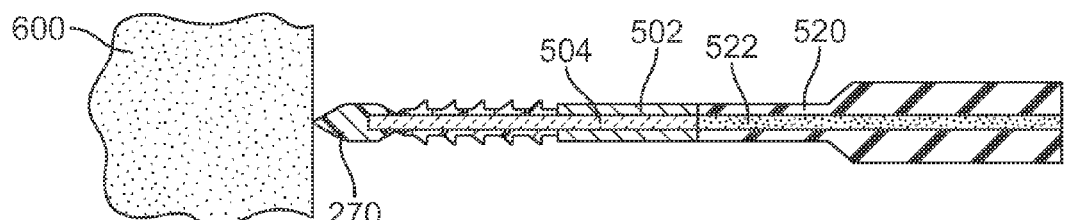
FIG. 36 is a schematic diagram illustrating a side view of some components of a deployment device being aligned with a tissue according to one embodiment.
Figure 37:
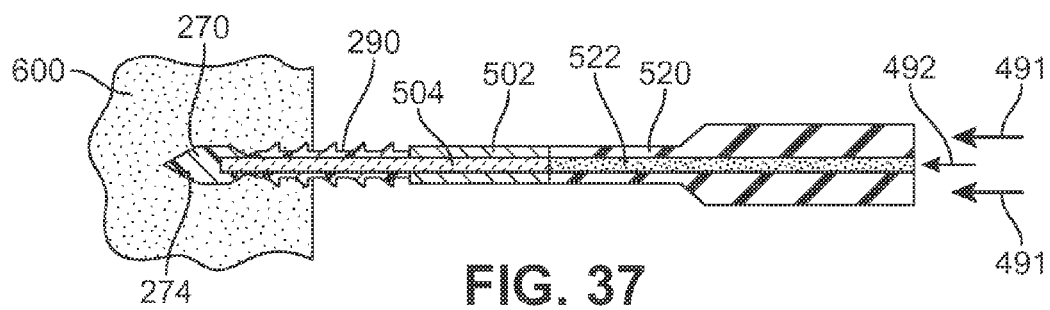
FIG. 37 is a schematic diagram illustrating a side view of the components of FIG. 36, in which a prosthesis is driven into the tissue.

As seen in FIG. 36, as a first step in the process, prosthesis 270 may be aligned with a desired region of tissue 600. Next, as shown in FIG. 37, driving tube 520 and driving pin 522 may apply approximately equivalent driving forces to first driven tube 502 and first driven pin 504. For purposes of reference the forces applied by driving tube 520 are indicated schematically by arrows 491, while forces applied by driving pin 522 are indicated schematically by arrow 492. These driving forces are then transferred by first driven pin 504 and first driven tube 502 to driving portion 274 and base portion 290, respectively, of prosthesis 270. During this first stage of the process, prosthesis 270 may be driven into tissue 600.

Figure 38:
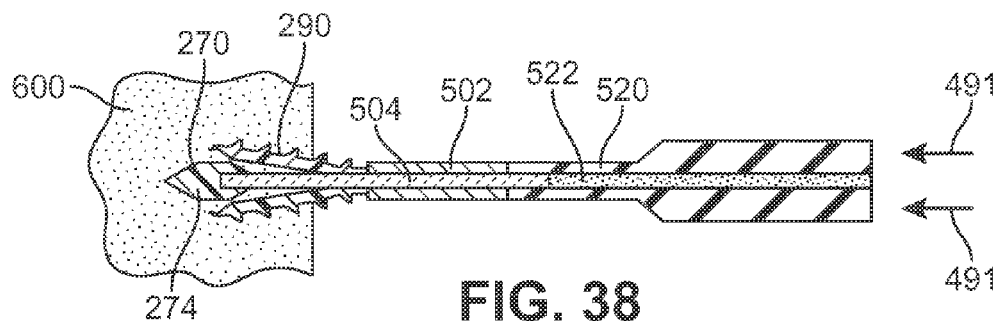
FIG. 38 is a schematic diagram illustrating a side view of the components of FIG. 37, in which a portion of the prosthesis begins to expand.
Figure 39:
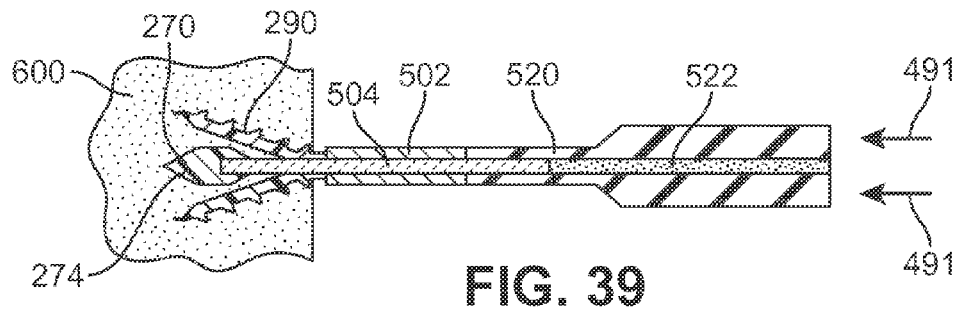
FIG. 39 is a schematic diagram illustrating a side view of the components of FIG. 38, in which a portion of the prosthesis continues to expand.

FIGS. 38 and 39 illustrate schematic views of a second stage in the process in which the motion of driving pin 522 and first driven pin 504 is halted. Driving tube 520, however, continues to move and applies a driving force to first driven tube 502, which is represented by arrows 491. This creates an imbalance of forces across prosthesis 270 as base portion 290 is driven further into tissue 600 while driving portion 274 remains in place. Eventually, base portion 290 separates away from driving portion 274 and begins to expand under the driving force of driving tube 504.

Figure 40:
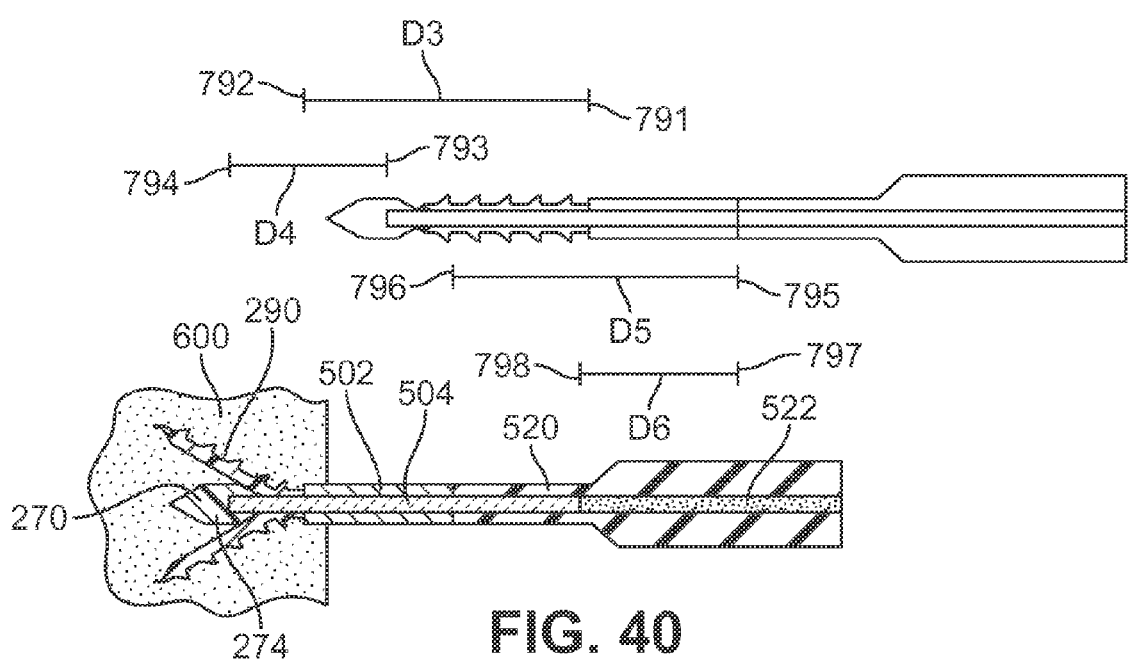
FIG. 40 is a schematic diagram illustrating a side view of the components of FIG. 39, in which the prosthesis has been fully implanted into the tissue.

FIG. 40 illustrates a schematic view of prosthesis 270 fully implanted into tissue 600. At this point, prosthesis 270 may be separated from first driven pin 504 and first driven tube 502. In embodiments where a suture thread is used with prosthesis 270, the suture thread may extend from driving portion 274 out through a newly formed opening in tissue 600.

As can be seen from comparing the positions of first driven tube 502 and first driven pin 504 in FIGS. 36 through 40, first driven tube 502 and first driven pin 504 undergo different amounts of displacement during the implantation process. For example, referring to FIG. 40, first driven tube 502 starts at an initial position 791 prior to implantation and moves to final position 792 once the implantation is complete. In some cases, final position 792 may be disposed distally farther from a deployment device (not shown) than initial position 791. The distance D3 traveled by first driven tube 502 is indicated schematically in FIG. 40. Additionally, first driven pin 504 starts at an initial position 793 prior to implantation and moves to final position 794 once the implantation is complete. In some cases, final position 794 may be disposed distally farther from the deployment device (not shown) than initial position 793. The distance D4 traveled by first driven pin 504 is indicated schematically in FIG. 40. In one embodiment, distance D3 may be substantially greater than distance D4. In other words, first driven tube 502 may travel substantially farther than first driven pin 504 during the implantation process.

Similar to the arrangement described above for first driven tube 502 and first driven pin 504, driving tube 520 may generally travel farther than driving pin 522 during implantation. For example, referring to FIG. 40, driving tube 520 starts at an initial position 795 prior to implantation and moves to final position 796 once the implantation is complete. In some cases, final position 796 may be disposed distally farther from a deployment device (not shown) than initial position 795. The distance D5 traveled by driving tube 520 is indicated schematically in FIG. 40. Additionally, driving pin 522 starts at an initial position 797 prior to implantation and moves to final position 798 once the implantation is complete. In some cases, final position 798 may be disposed distally farther from the deployment device (not shown) than initial position 797. Additionally, in some cases, initial position 797 of driving pin 522 may coincide with initial position 795 of driving tube 520. The distance D6 traveled by driving pin 522 is indicated schematically in FIG. 40. In one embodiment, distance D5 may be substantially greater than distance D6. In other words, driving tube 520 may travel substantially farther than driving pin 522 during the implantation process.

Figure 41:
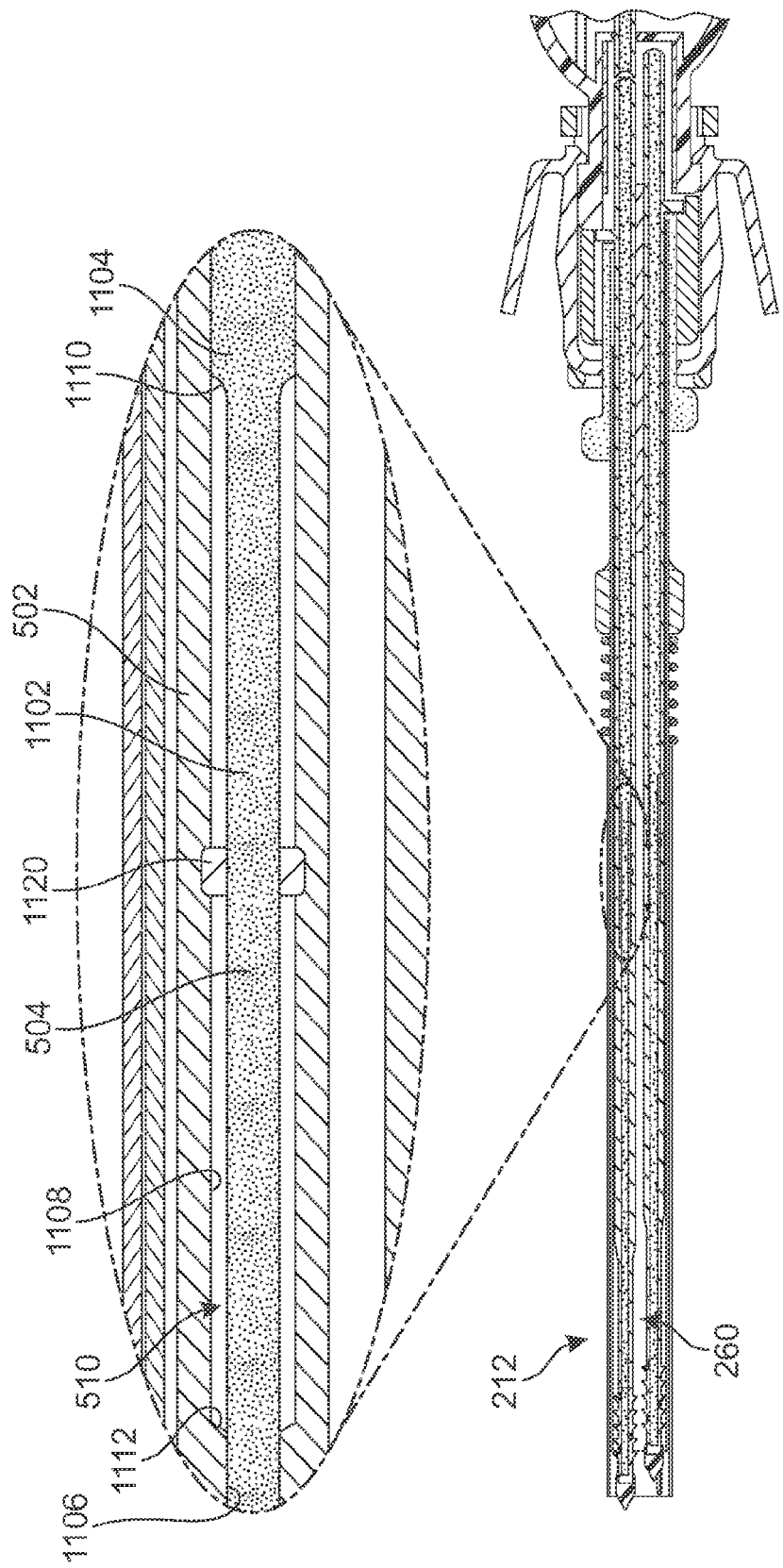
FIG. 41 is a schematic diagram illustrating a side cross-sectional view of a portion of a deployment device according to one embodiment.

FIG. 41 illustrates a side cross-sectional view of front delivery assembly 212 for purposes of describing the geometry of plurality of driven assemblies 260. Referring to FIG. 41, some embodiments may incorporate provisions that help prevent a driven pin from falling out of a driven tube. In some embodiments, a driven pin and driven tube may be configured with corresponding geometries that help restrict the maximum distance that the driven pin may move within the driven tube. As one possible example, the current embodiment illustrates first driven pin 504 having a first portion 1102 and a second portion 1104. In this case, first portion 1102 has a substantially smaller diameter than second portion 1104. Moreover, hollow longitudinal cavity 510 of first driven tube 502 may be configured with a first cavity section 1106 and a second cavity section 1108. In this case, first cavity section 1106 may have a substantially smaller diameter than second cavity section 1108. Moreover, the diameters of first cavity section 1106 and second cavity section 1108 may be selected so that both first portion 1102 and second portion 1104 of first driven pin 504 may translate through second cavity section 1108, but only first portion 1102 may translate through first cavity section 1106. In particular, first driven pin 504 includes shoulder portion 1110 that may abut an o-ring associated with interior surface 1112 of hollow longitudinal cavity 510, which prevents first driven pin 504 from translating further in the axial direction. Using this arrangement, first driven pin 504 is prevented from falling out of first driven tube 502, for example, under the force of gravity. It will be understood that other assemblies of driven assemblies 260 may be configured in a similar manner so that each driven pin is prevented from falling out of, or over extending from, the corresponding driven tube.

As seen in FIG. 41, some embodiments can further include a ring member 1120. Ring member 1120 may be configured to fit around first portion 1102 of first driven pin 504 and within second cavity section 1108. In some cases, ring member 1120 may be configured as a friction ring that helps to provide a predetermined amount of resistance against the relative movement of first driven pin 504 within first driven tube 502.

Figure 42:
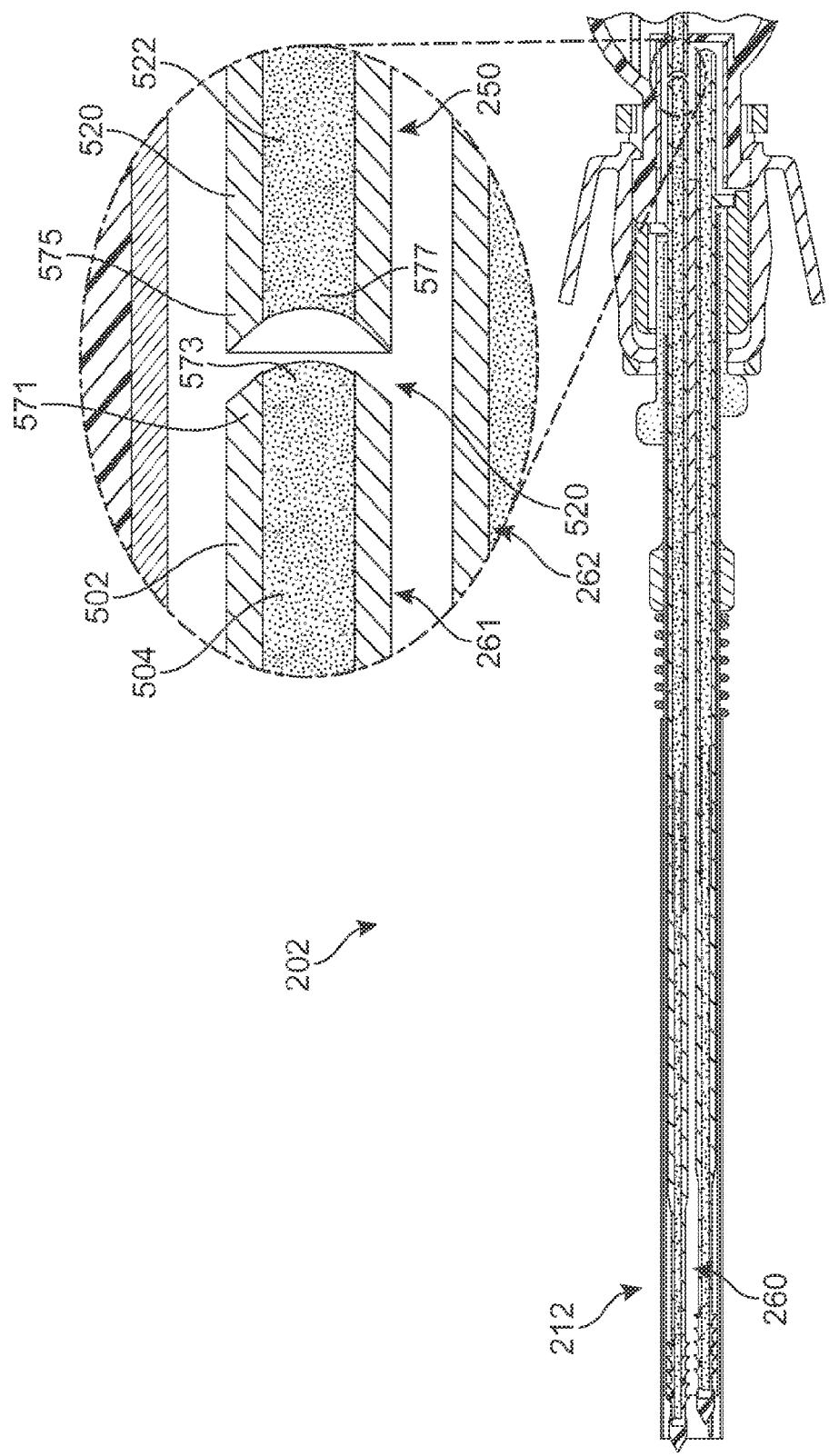
FIG. 42 is a schematic diagram illustrating a side cross-sectional view of a portion of a deployment device according to one embodiment.

FIG. 42 illustrates a schematic cross-sectional view of a portion of deployment device 202 in order to illustrate one possible provision for ensuring concentric alignment of driving assembly 250 and one or more of driven assemblies 260. In one embodiment, each of driving tube 520, driving pin 522, first driven tube 502 and first driven pin 504 may be configured with corresponding approximately conical geometries. For example, forward end portion 575 of driving tube 520 and forward end portion 577 of driving pin 522 may have concave shapes that receive the convex shapes of rearward end portion 571 of first driven tube 502 and rearward end portion 573 of first driven pin 504, respectively. Using this arrangement, as driving assembly 250 impacts first driven assembly 261, these corresponding geometries act to concentrically align first driven assembly 261 and driving assembly 250. Of course, it will be understood that second driven assembly 262 may be configured with a substantially similar geometry to first driven assembly 261 so that second driven assembly 262 likewise may have a corresponding geometry with driving assembly 250 that facilitates concentric alignment.

Figure 43:
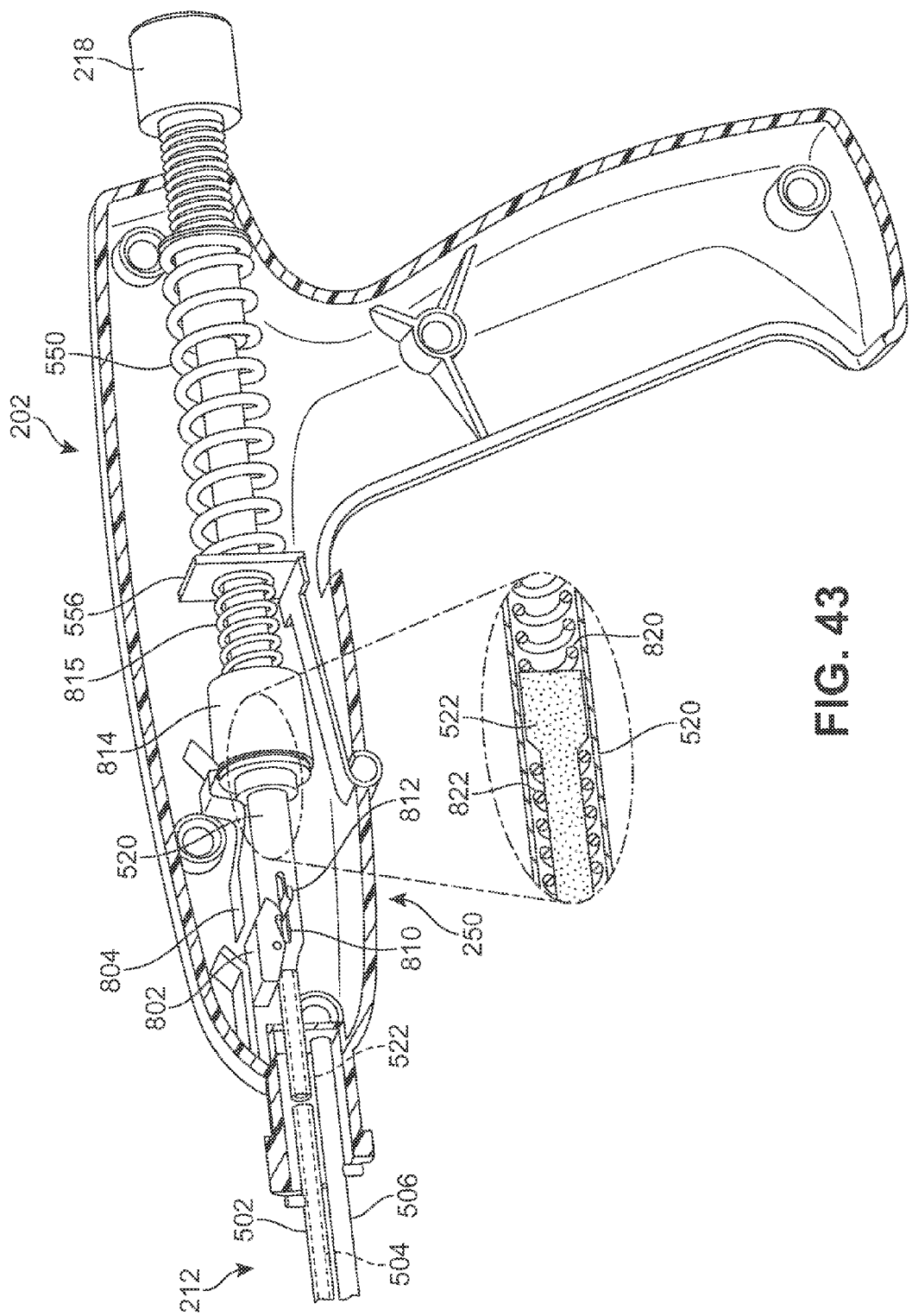
FIG. 43 is a schematic diagram illustrating an isometric cut-away view of an embodiment of a portion of a base assembly including components used to generate and control an impact force.

FIG. 43 illustrates an isometric cut-away view of a portion of deployment device 202. For purposes of clarity, only some components of deployment device 202 are shown. For example, only some components of front delivery assembly 212 are shown, including first driven tube 502, first driven pin 504 (shown in phantom), and second driven tube 506.

Referring to FIG. 43, driving assembly 250 may comprise various components that facilitate the two stage implantation process for one or more prostheses. In some embodiments, driving assembly 250 includes provisions to control and/or constrain the relative movement between driving tube 520 and driving pin 522. In some embodiments, driving tube 520 may include longitudinal slot 810. In addition, driving pin 522 may include protruding portion 812 that is perpendicular to the length of driving pin 522. In some cases, protruding portion 812 extends through longitudinal slot 810. In some cases, protruding portion 812 extends laterally through longitudinal slot 810. This configuration may limit the relative movement between driving tube 520 and driving pin 522, as longitudinal slot 810 constrains the position of protruding portion 812 and thereby limits the relative movement of driving pin 522.

Figure 45:
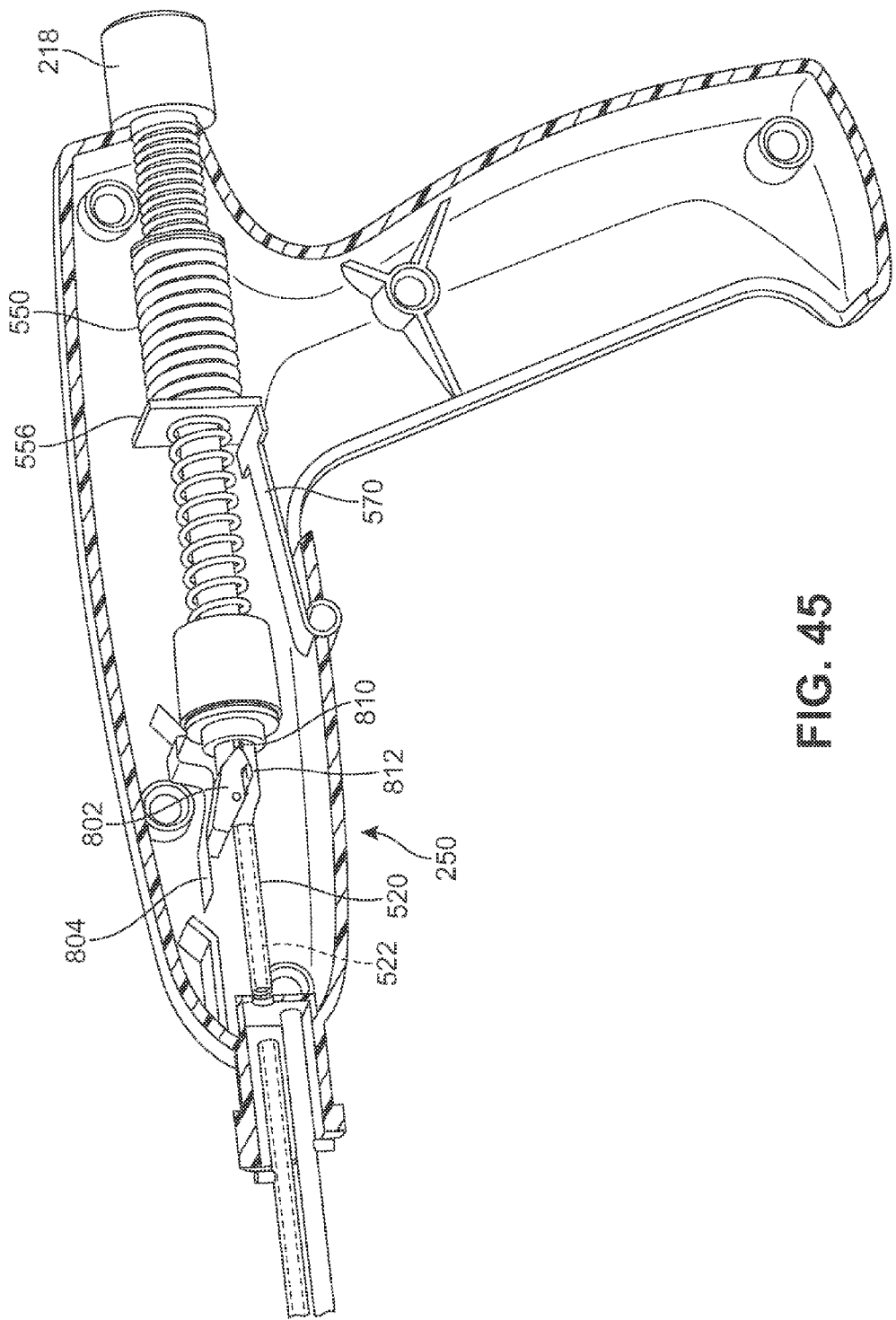
FIG. 45 is an isometric cut-away view of the base assembly of FIG. 43, in which an impact spring has been loaded.

In some embodiments, driving assembly 250 includes control hook 802 that is attached to driving tube 520. In some cases, control hook 802 may be attached to driving tube 520 in a manner that allows control hook 802 to pivot about driving tube 520. Moreover, in some embodiments, control hook 802 may be rotatable between an engaged position and a disengaged position. As is shown in FIG. 45, in the engaged position, control hook 802 may engage protruding portion 812 of driving pin 522. As is shown in FIG. 43, in the disengaged position, control hook 802 may be disengaged from protruding portion 812 of driving pin 522. As discussed in further detail below, placing control hook 802 in the engaged position around protruding portion 812 acts to prevent any relative movement between driving tube 520 and driving pin 522. Also, with control hook 802 in the disengaged position, driving pin 522 may move relative to driving tube 520.

In some embodiments, driving assembly 250 may further include hook biasing spring 804. In some embodiments, hook biasing spring 804 may be configured to interact with control hook 802. In some cases, the geometry of hook biasing spring 804 is configured such that control hook 802 is rotated into an engaged position when control hook 802 is disposed beneath hook biasing spring 804.

In some embodiments, driving assembly 250 can include bumper member 814. In some embodiments, bumper member 814 may help to terminate the stroke of impact collar 556 at the end of the impact stroke. Bumper member 814 could be configured with any shape, size, and/or material. The shape, size, and material could be selected to absorb a predetermined amount of force generated by impact collar 556 at the end of the impact stroke.

In some embodiments, driving assembly 250 can also include impact return spring 815. In some embodiments, impact return spring 815 may be positioned between impact collar 556 and bumper member 814. In some embodiments, return spring 815 may help bias impact collar 556 in a default position that is spaced apart from bumper member 814.

Some embodiments can include one or more biasing springs that help bias the position of driving pin 522 within driving tube 520. For example, as shown in the enlarged cut-away view in FIG. 43, driving assembly 250 may include first biasing spring 820 and second biasing spring 822. In some embodiments, first biasing spring 820 and second biasing spring 822 may act to bias the position of driving pin 522 within driving tube 520 such that the default position of protruding portion 812 is aligned with, and capable of being engaged by, control hook 810.

Figure 44:
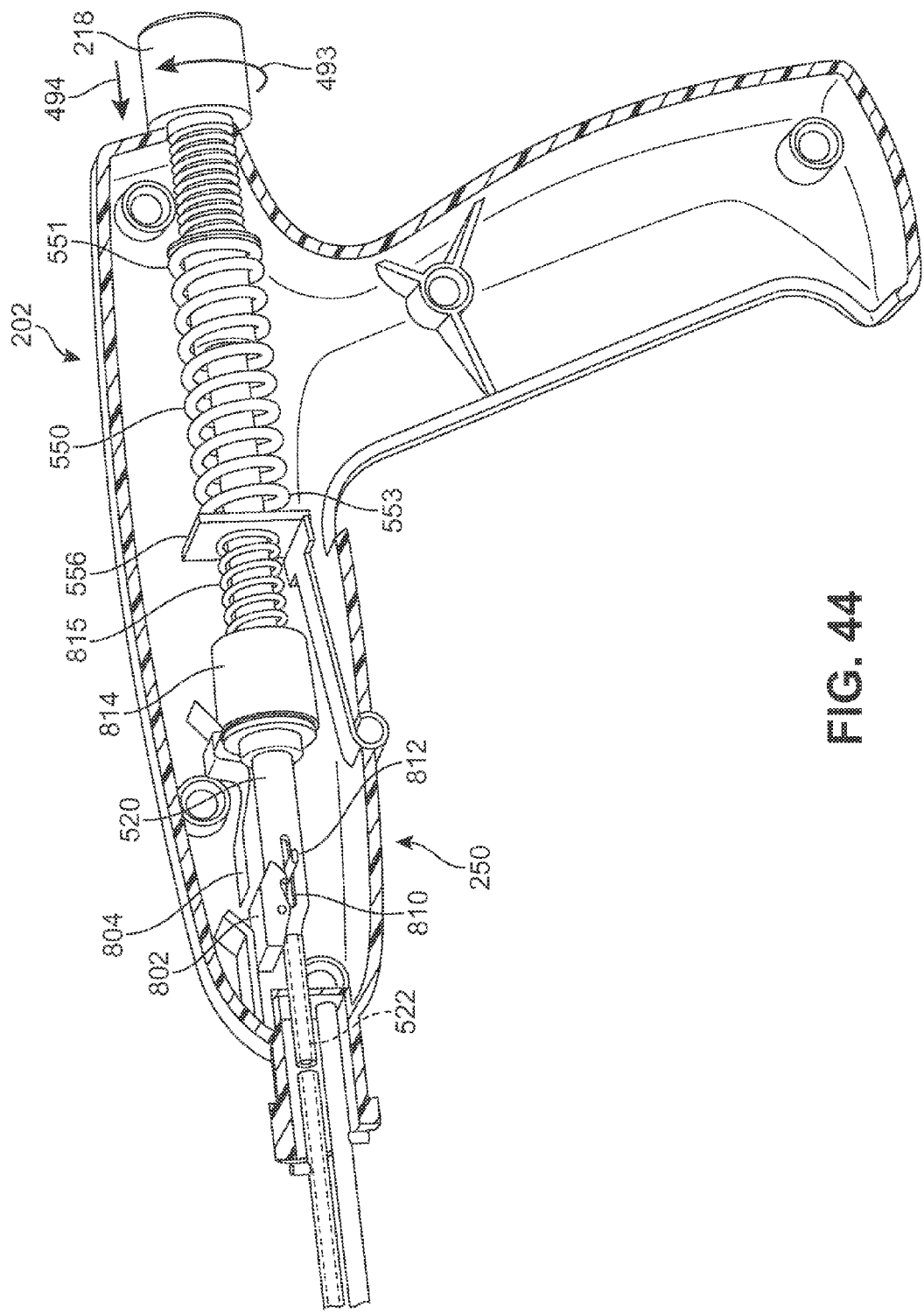
FIG. 44 is a schematic diagram illustrating an isometric cut-away view of the base assembly of FIG. 43, in which a control knob has been adjusted.

As previously discussed, delivery device 202 may include provisions that allow a surgeon to control the impact force generated by delivery device 202. In some embodiments, control knob 218 can be used to adjust the impact force. In one embodiment, control knob 218 can be used to adjust the compression of impact spring 550. For example, FIG. 44 illustrates a possible configuration for control knob 218, where control knob 218 has been rotated in a direction represented by arrow 493 in order to adjust the position of rearward end portion 551 of impact spring 550. In this case, rearward end portion 551 may be moved towards forward end portion 553 of impact spring 550, which is a direction schematically indicated by arrow 494, in order to increase the amount that impact spring 550 is compressed from the free length of impact spring 550. This provides a surgeon with some control of the position of rearward end portion 551, which can be used to adjust the impact force generated during implantation. As previously discussed, the position of control knob 218, and thus the amount of impact force generated during implantation, can be selected according to various factors including the type of implantation tissue, the geometry and/or material construction of a prosthesis, the type of tissue repair, and the method of repair employed by the surgeon, as well as other factors.

For purposes of reference, the term "impact cycle" is used throughout the remainder of this detailed description and in the figures to refer to a sequence of events in which a driving assembly is retracted and then propelled forward to impact a driven assembly. The impact cycle may include an energy storage stage where the driving assembly is retracted away from a driven assembly and energy is stored in an energy storage device (such as an impact spring). The impact cycle can also include a driving stage where the driving assembly is projected forward to impact a driven assembly as energy is released from the energy storage device. In some cases, the impact cycle starts with the driving assembly in an initial or pre-actuated position and likewise ends with the driving assembly in a final position that is substantially the same as the initial position.

FIGS. 45 through 48 illustrate views of a possible actuating sequence for driving assembly 250 that allows for the two stage implantation process described above and shown schematically in FIGS. 36 through 40. As seen in FIG. 45, positioning ram 570 may be used to adjust the position of impact collar 556. In some cases, a surgeon may interact with a trigger or other mechanism in order to move positioning ram 570.

As positioning ram 570 and impact collar 556 are translated rearwardly, impact spring 550 may be compressed, thereby storing mechanical energy within impact spring 550. Since impact collar 556 is fixedly attached to driving tube 520, control hook 802 may also translate rearwardly until control hook 802 is disposed beneath hook biasing spring 804. This causes control hook 802 to rotate into a position such that control hook engages protruding portion 812, which is positioned at a distal most portion of longitudinal slot 810.

Figure 46:
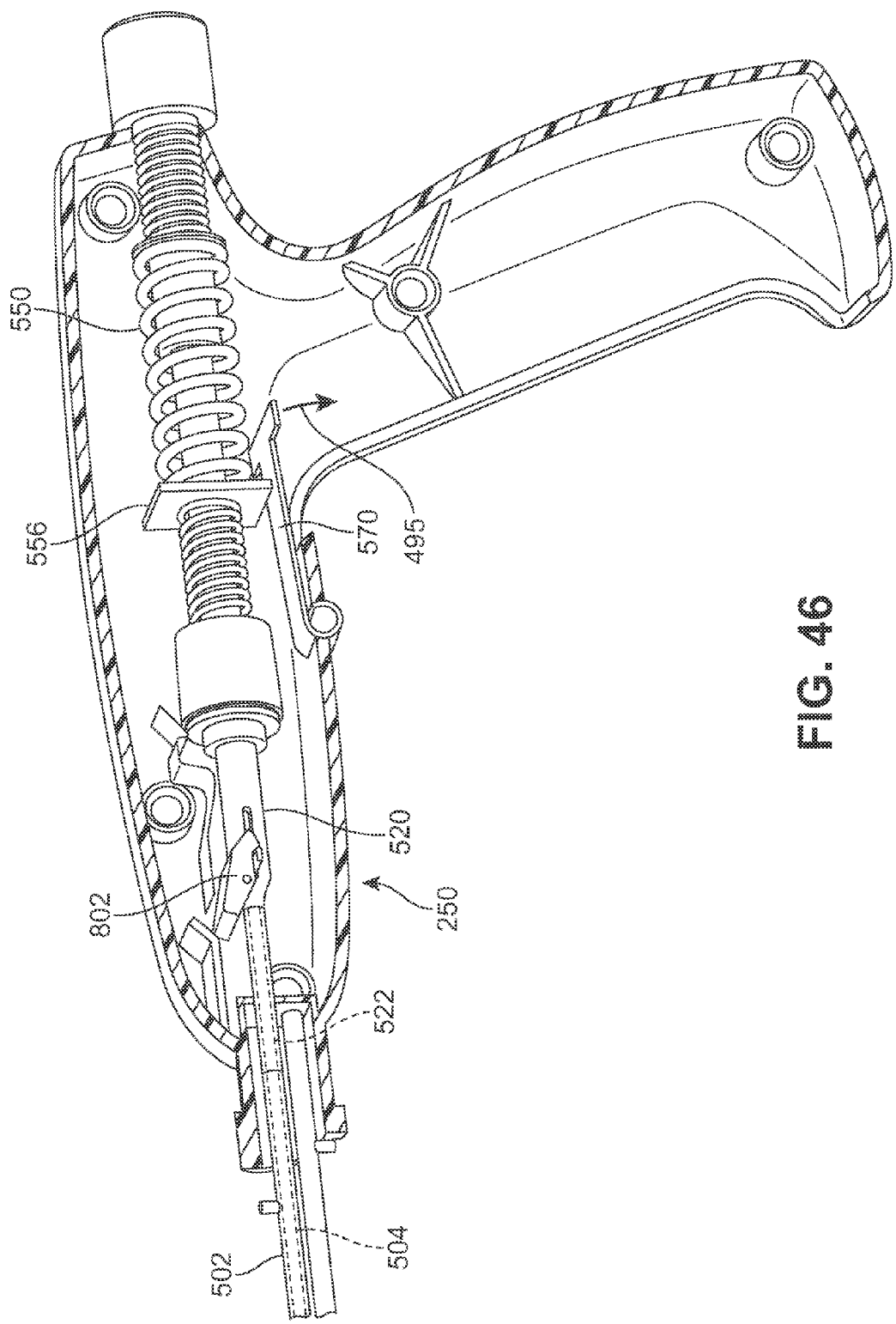
FIG. 46 is a schematic diagram illustrating an isometric cut-away view of the base assembly of FIG. 43, in which an impact spring has been released and a driving pin and driving tube move together.

Following this, as shown in FIG. 46, positioning ram 570 may rotate out of the way of impact collar 556 as represented by arrow 495, which allows impact collar 556 to be released. This may occur at the end of a trigger event that includes loading and then releasing impact spring 550, or as a separate trigger event that occurs an indefinite period of time after impact spring 550 has been loaded. Once released, the energy stored within impact spring 550 is transferred to impact collar 556 in the form of mechanical energy. Thus, impact collar 556 may be quickly accelerated, which accelerates driving tube 520 and driving pin 522 towards driven tube 502 and driven pin 504. With driving tube 520 and driving pin 522 locked together by control hook 802, driven tube 502 and driven pin 504 may be impacted simultaneously. This acts to drive a corresponding prosthesis (not shown) into a tissue during the first stage of implantation. As an example, the corresponding motions of driving tube 520, driving pin 522, first driven tube 502, and first driven pin 504 at this point may be similar to the scenario depicted in FIG. 37.

Figure 47:
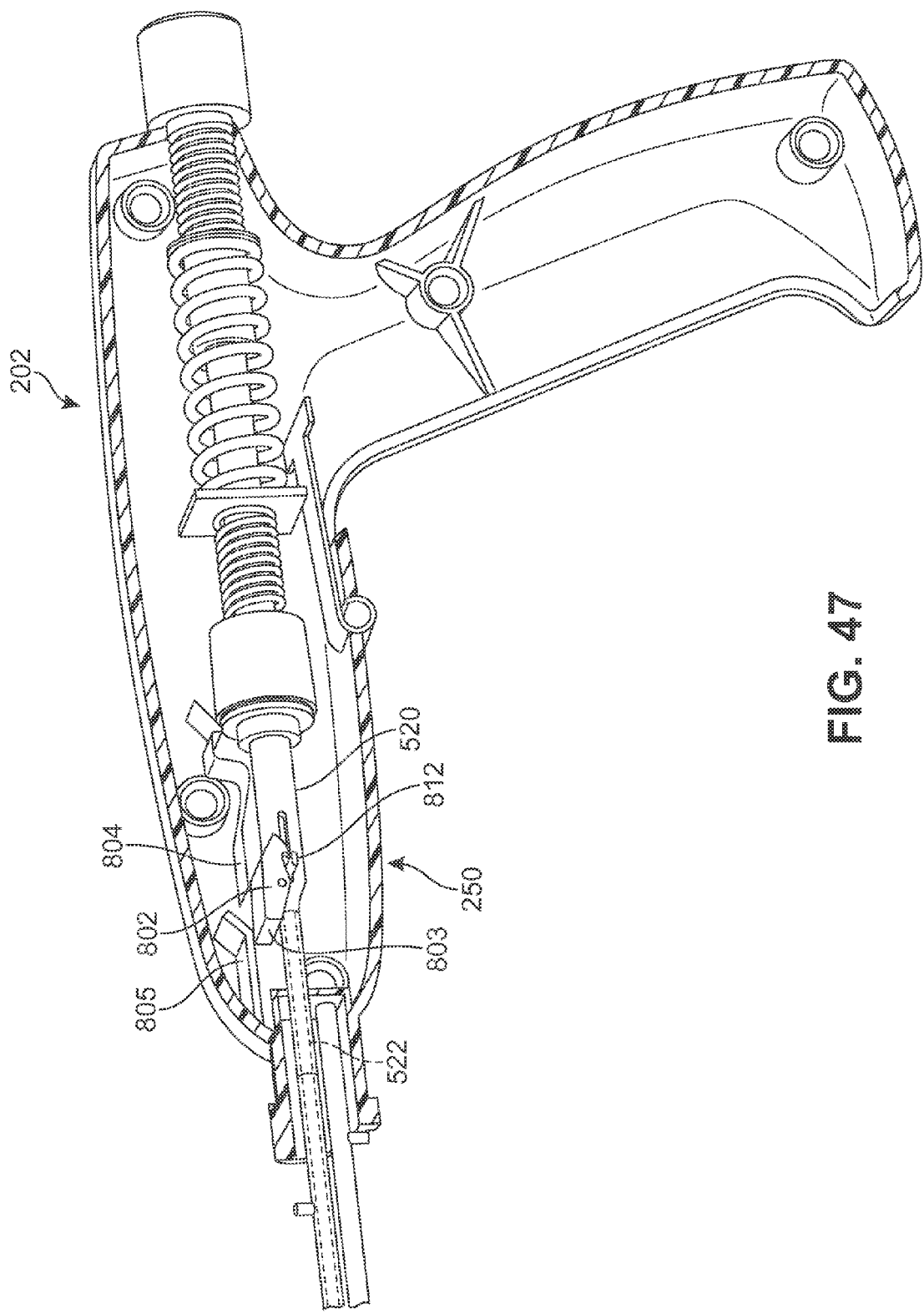
FIG. 47 is a schematic diagram illustrating an isometric cut-away view of the base assembly of FIG. 43, in which a control hook releases a projecting portion of the driving pin.

Referring now to FIG. 47, as driving assembly 250 continues to move in the forward direction, control hook 802 may disengage with hook biasing spring 804. Moreover, at some point distal end 803 of control hook 802 may engage with hook biasing ramp 805 of delivery device 202. Upon engaging with hook biasing ramp 805, control hook 802 may be automatically rotated from the engaged position to the disengaged position, which releases protruding portion 812.

Figure 48:
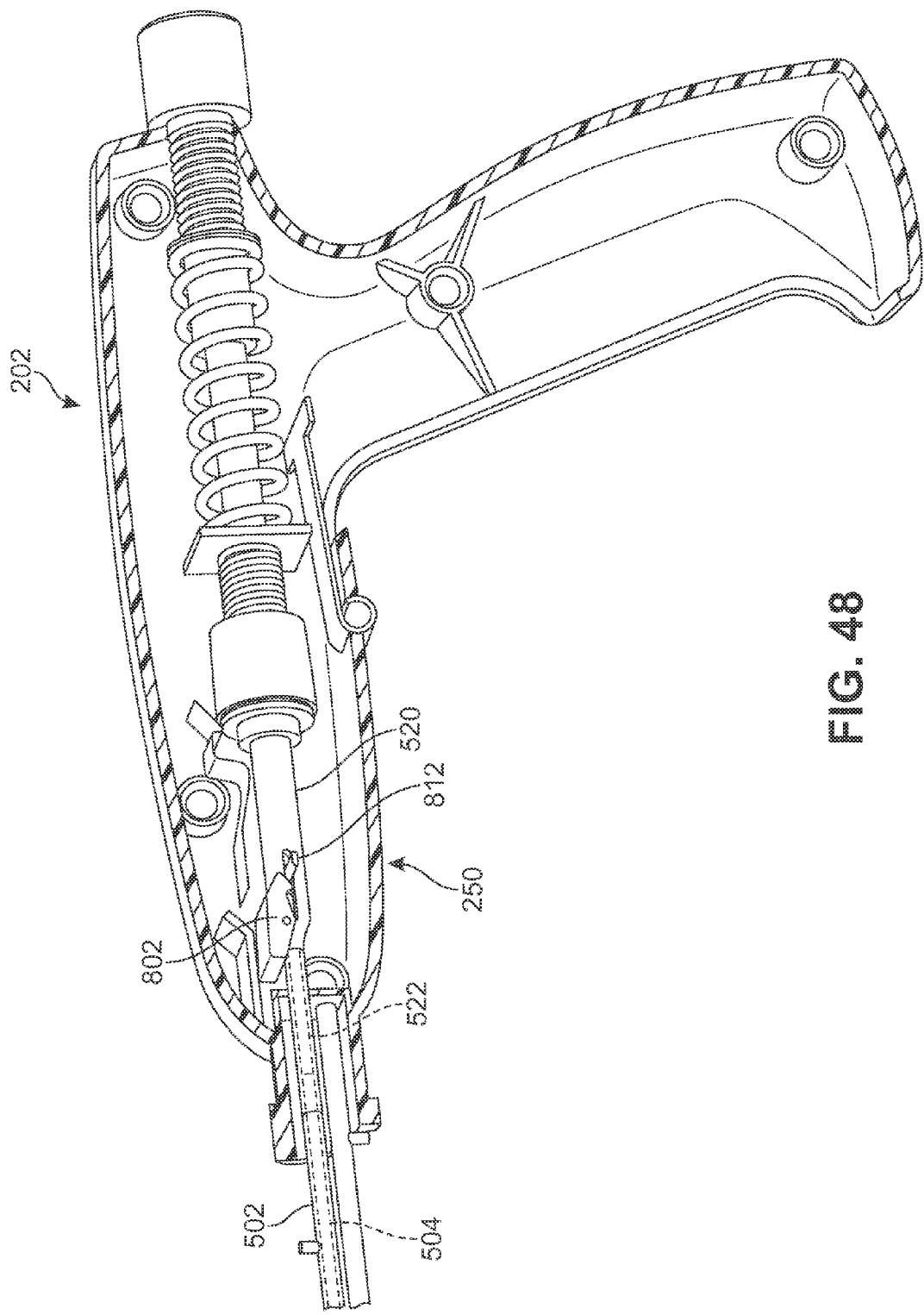
FIG. 48 is a schematic diagram illustrating an isometric cut-away view of the base assembly of FIG. 43, in which a driving pin and a driving tube can move independently.

Referring now to FIG. 48, with protruding portion 812 released from control hook 802, driving pin 522 and driving tube 520 may translate with respect to one another. At this point, driving tube 520 may continue to move forward while the motion of driving pin 522 is approximately stopped or substantially decreased, which starts the second stage of the implantation process. In some embodiments, any further motion of driving pin 522 at this point in the impact cycle may be impeded as protruding portion 812 reaches the end of retaining slot 267 (see FIGS. 13 and 14). An example of the corresponding motions of driving tube 520, driving pin 522, first driven tube 502, and first driven pin 504 at this point may be similar to the scenario depicted in FIGS. 38 and 39. Driving tube 520 may continue to push against driven tube 502, while the degree of forces transferred from driving pin 522 to driven pin 520 is drastically reduced. Therefore, driven tube 502 continues to deliver an impacting force to a prosthesis while driven pin 504 ceases to deliver any substantial impacting force to the prosthesis. This may have the effect of expanding a base portion of a prosthesis (as show, for example, in FIGS. 38 and 39).

The process described here for applying an impacting force in order to implant a prosthesis can be repeated. In some cases, this process can be repeated so that multiple impacts are applied to the same prosthesis, as discussed in further detail below. In other cases, this process can be repeated by implanting a first prosthesis, rotating front delivery assembly 212 (see FIG. 54) so as to align a second prosthesis in a driving position, and implanting the second prosthesis. Moreover, for embodiments utilizing N anchors, the process could be repeated at least N times to implant the N anchors in succession.

A trigger assembly can include provisions for automatically returning to a ready position. In some embodiments, a trigger assembly may be configured with provisions to automatically reengage a positioning ram with an impact collar immediately after actuation of the driving assembly, once the surgeon has released the trigger portion. This configuration allows the driving assembly to be conveniently actuated multiple times in a given surgical procedure.

Figure 49:
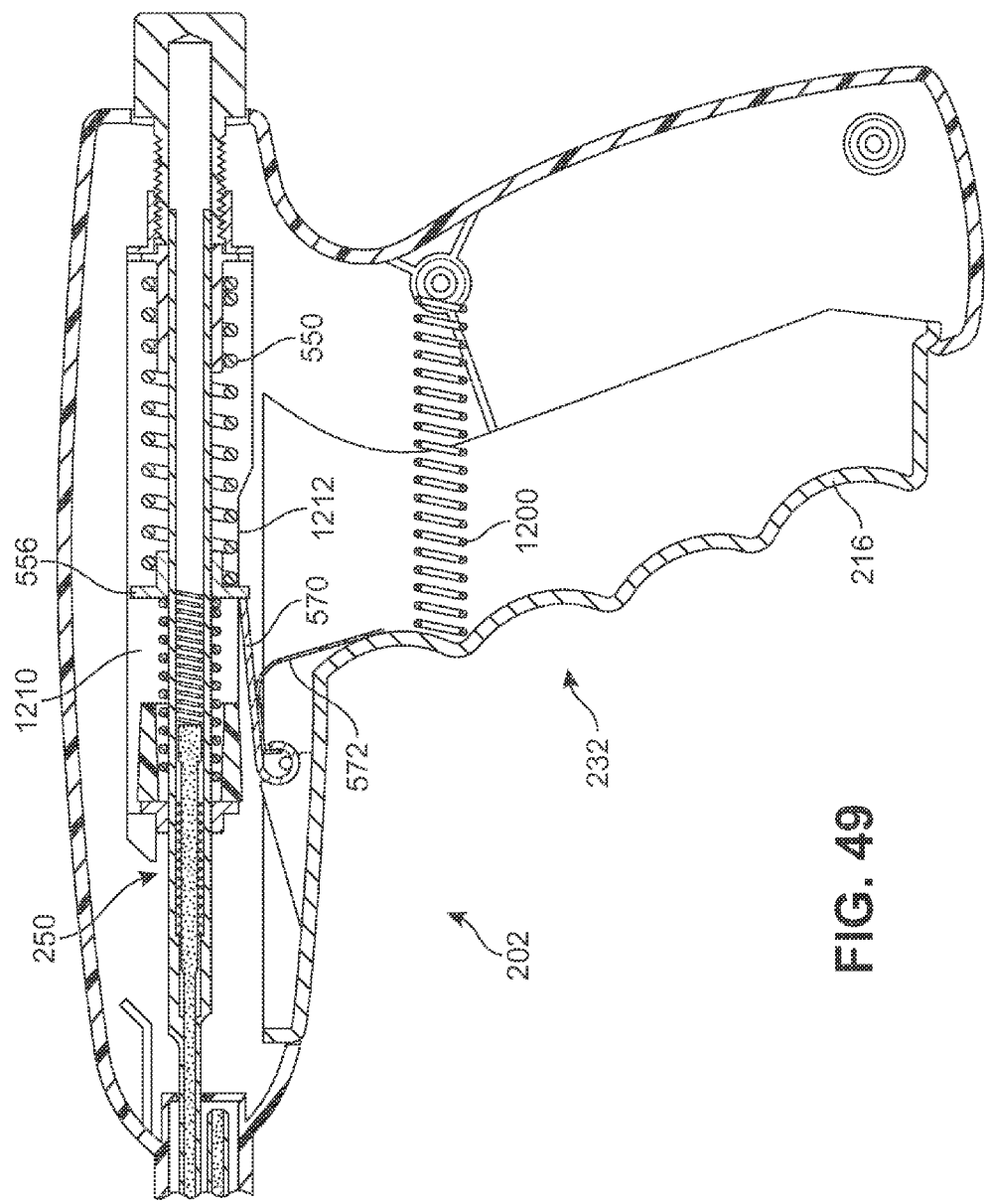
FIG. 49 is a schematic diagram illustrating an embodiment of a base assembly including a trigger assembly.

FIGS. 49-52 illustrate schematic cut-away views of a portion of deployment device 202, in order to demonstrate the detailed operation of trigger assembly 232 and driving assembly 250. Referring first to FIG. 49, trigger assembly 232 comprises trigger portion 216, trigger biasing spring 1200, positioning ram 570 and ram biasing spring 572. The components of trigger assembly 232 may act to move impact collar 556 in a rearward direction in order to compress impact spring 550.

As previously mentioned, portions of driving assembly 250, including impact spring 550 and impact collar 556 are housed within brace member 1210. Moreover, positioning ram 570 is biased upwardly by ram biasing spring 572 until it contacts lower peripheral edge 1212 of brace member 1210.

In the pre-impact configuration shown in FIG. 49, positioning ram 570 of trigger assembly 232 is engaged with impact collar 556 of driving assembly 250. This ensures that as trigger assembly 232 is engaged (for example, when a surgeon squeezes trigger portion 216) positioning ram 570 (which translates with trigger portion 216) will translate impact collar 556 rearwardly.

Figure 50:
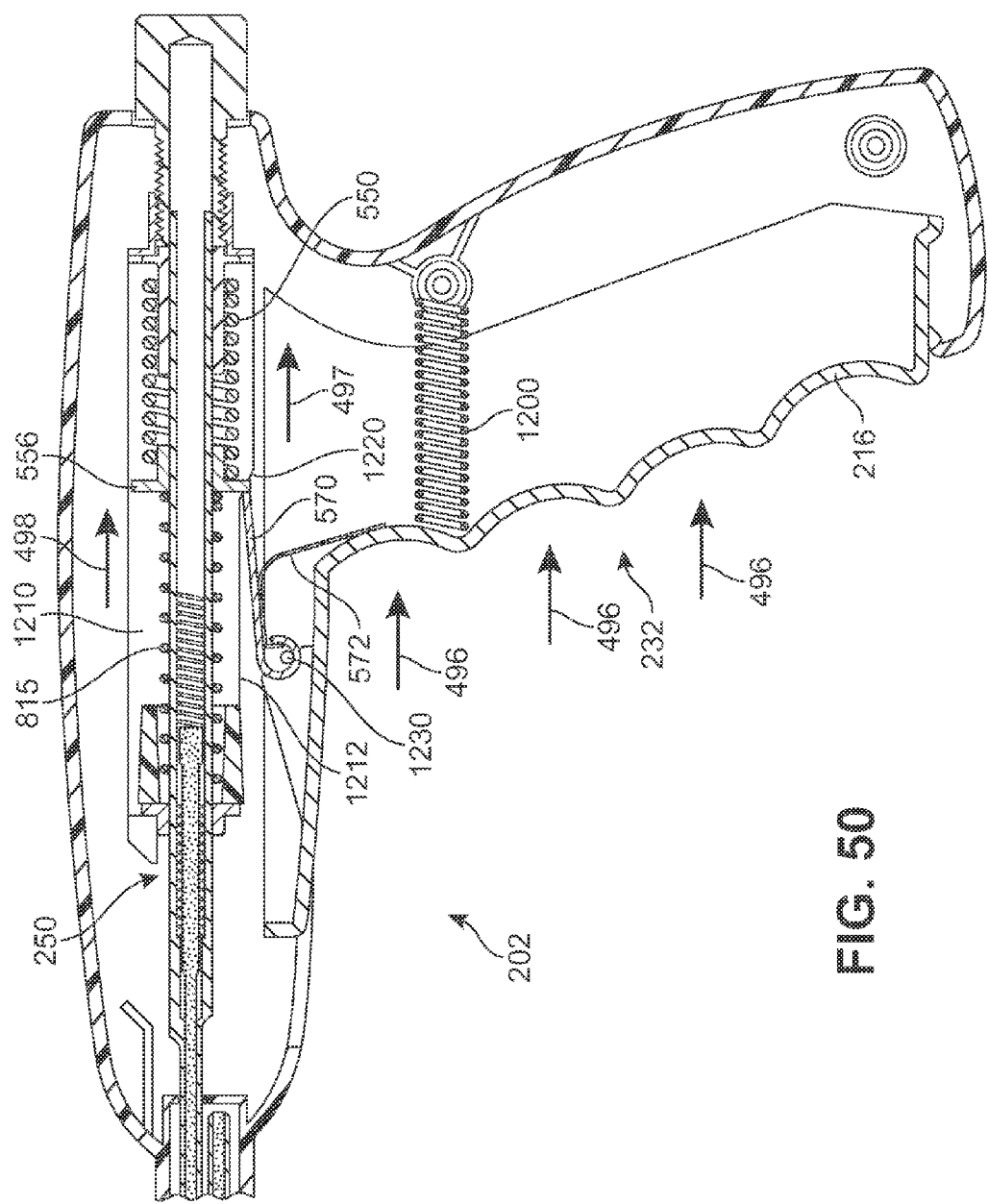
FIG. 50 is a schematic diagram of the base assembly of FIG. 49, in which the trigger assembly is engaged.
Figure 51:
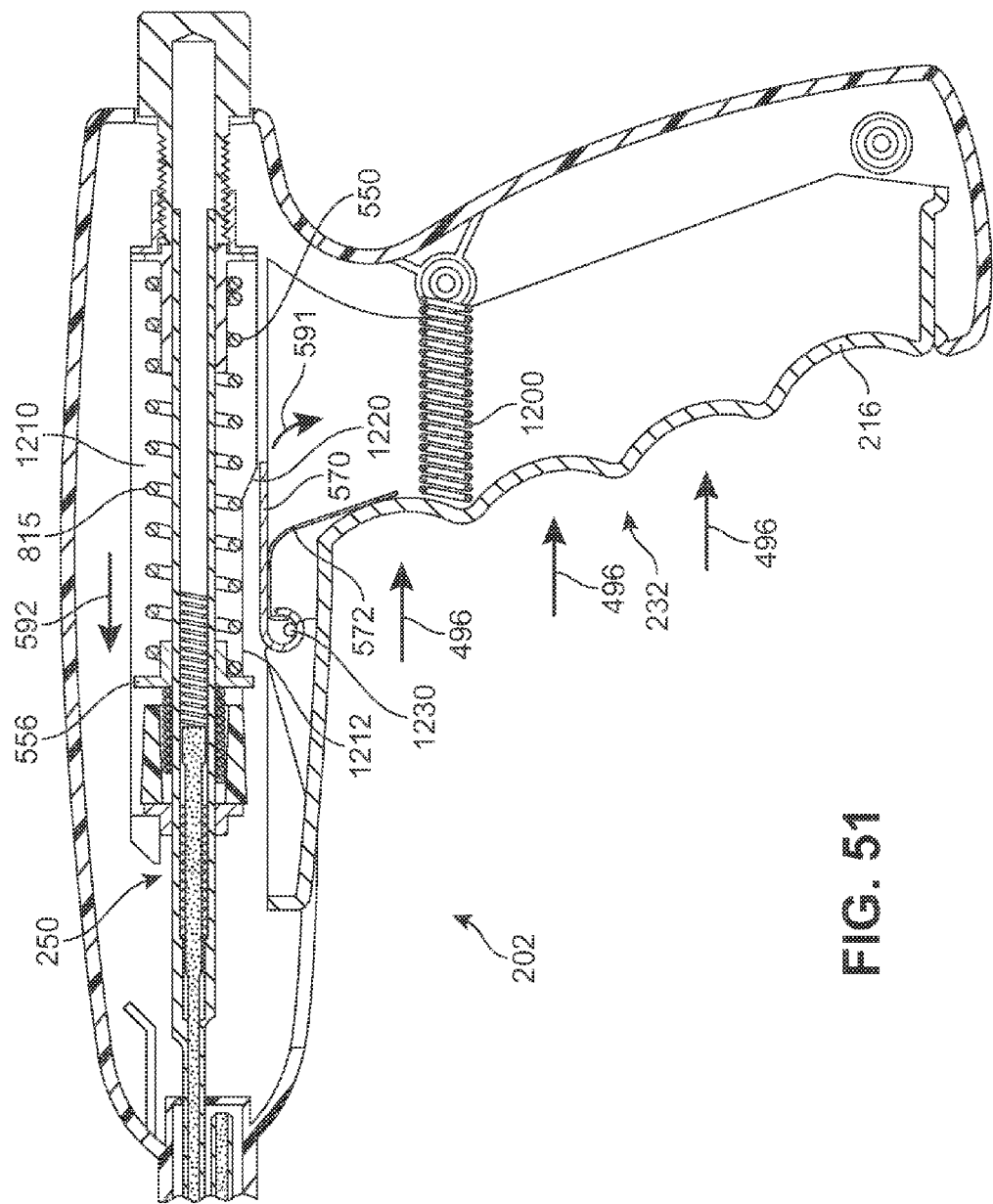
FIG. 51 is a schematic diagram of the base assembly of FIG. 49, in which the trigger assembly is engaged and an impact spring has been released.

Referring next to FIGS. 50 and 51, as trigger portion 216 is squeezed by a surgeon in a direction represented by arrows 496, positioning ram 570 is translated along lower peripheral edge 1212 of brace member 1210. As seen in FIG. 50, positioning ram 570 translates rearwardly in the direction indicated by arrow 497 and causes impact collar 556 to move in a similar rearward direction indicated by arrow 498, which acts to compress impact spring 550 and store energy. As positioning ram 570 translates down sloped section 1220 of lower peripheral edge 1212, positioning ram 570 is rotated about pivoting portion 1230, as represented by arrow 591 (see FIG. 51), until it is below impact collar 556. Once positioning ram 570 is rotated out of contact with impact collar 556, impact spring 550 may rapidly expand. This moves impact collar 556 in a forward direction represented by arrow 592 in order to supply an impacting force for driving assembly 250.

Figure 52:
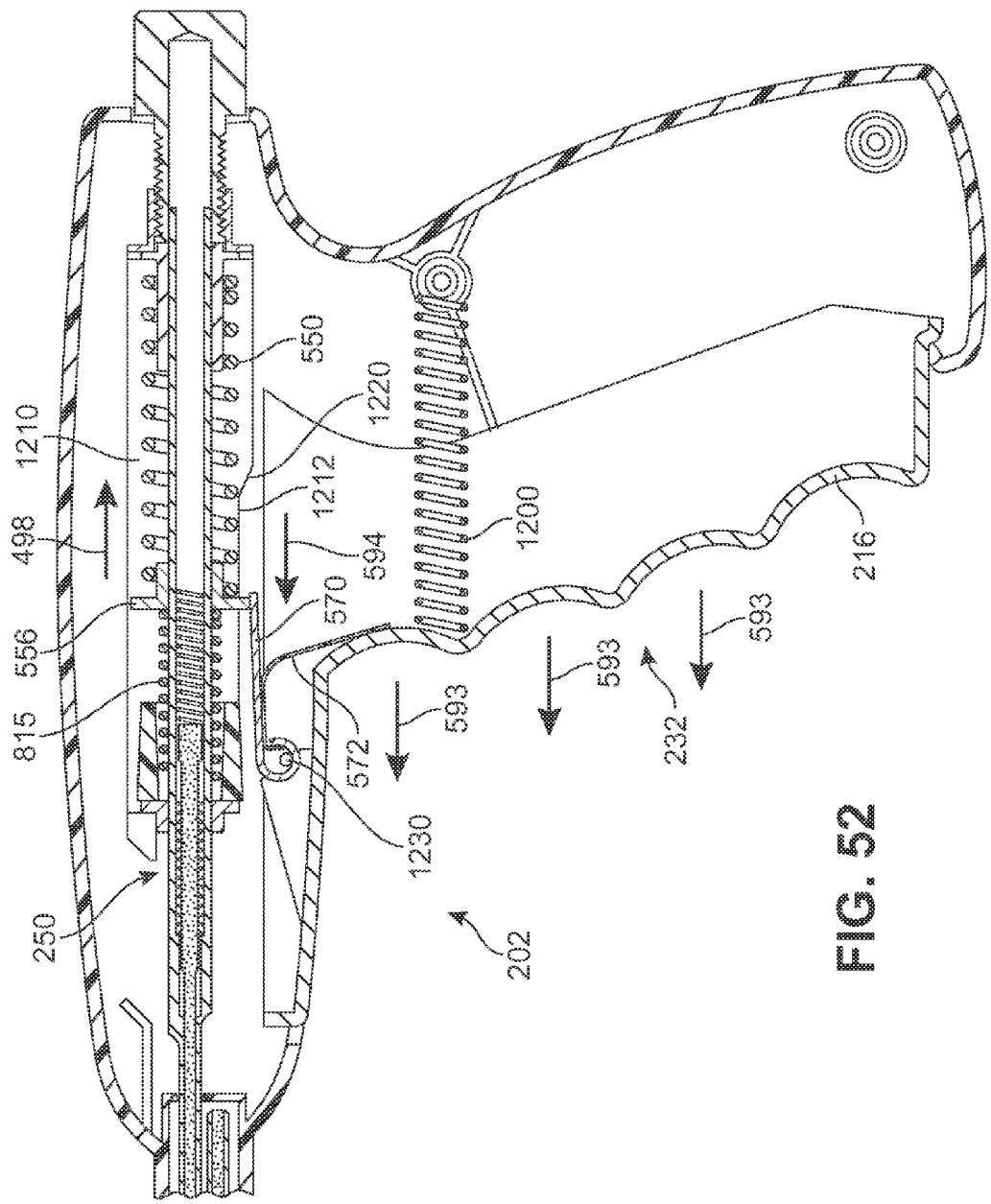
FIG. 52 is a schematic diagram of the base assembly of FIG. 49, in which the trigger assembly and a driving assembly are returning to a default position.

Referring next to FIG. 52, following the impacting event, impact collar 556 may be moved towards a default position under the force of impact return spring 815. In particular, impact collar 556 may travel rearwardly, as represented by arrow 498, towards a default position. Additionally, once trigger portion 216 has been released by the surgeon, trigger biasing spring 1200 biases or urges trigger portion 216 and positioning ram 570 forwards, as represented by arrows 593 and arrow 594. Eventually, following the stage shown in FIG. 52, positioning ram 570 is pushed forwards of impact collar 556 and rotated up into an engaged position by ram biasing spring 572. At this point, trigger assembly 232 and driving assembly 250 have been reset so that driving assembly 250 can be re-engaged when a surgeon depresses trigger portion 216 again. In some cases, the final position of deployment device following a trigger event is substantially identical to the initial configuration, which is shown in FIG. 49.

Configuring a deployment device to allow multiple impacts to be applied to the same prosthesis can improve the versatility of the deployment device. As an example, this configuration may enable a surgeon to adapt to variations in tissue during surgery (e.g. variations in bone density). Rather than requiring the deployment device to be tuned so that the surgeon can be assured the prosthesis will be implanted during a single impact, the multi-impact design of the embodiments described here allow for a surgeon to iteratively implant a prosthesis to the desired depth through the application of one, two or more impacts to the prosthesis.

Detachable Front Delivery Assembly

Figure 53:
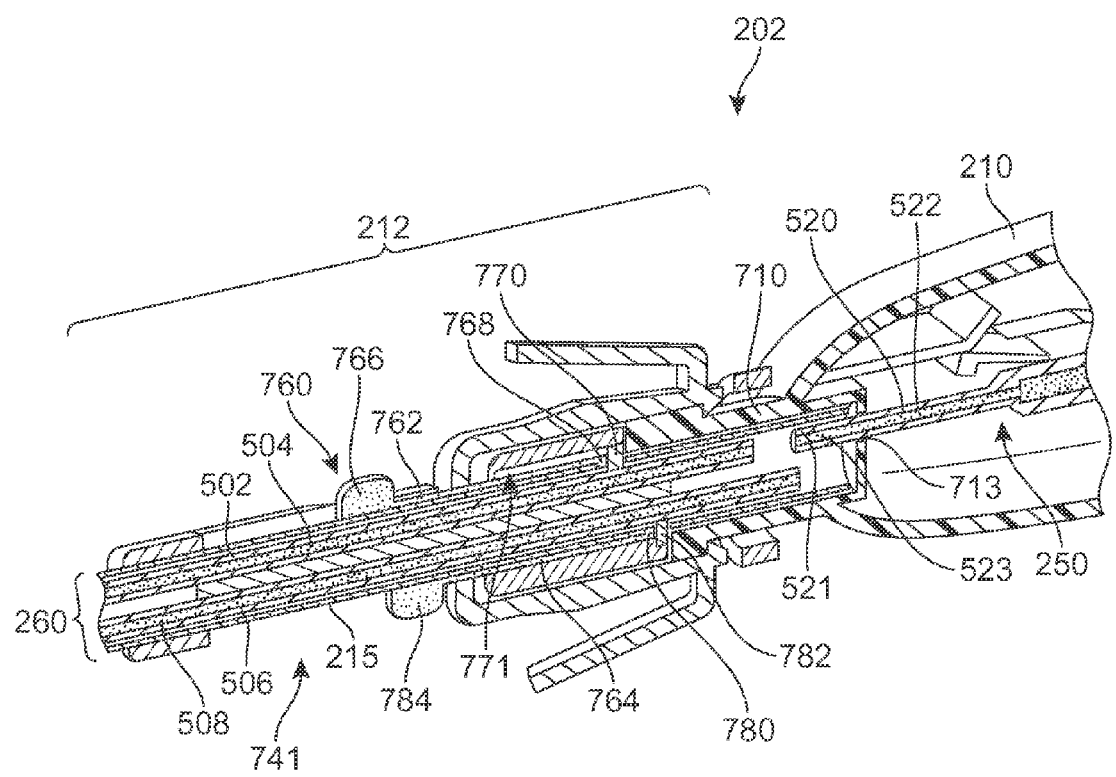
FIG. 53 is a schematic diagram illustrating an isometric cut-away view of an embodiment of a portion of a front delivery assembly and a portion of a base assembly.

FIG. 53 illustrates a cut-away view of adjacent portions of front delivery assembly 212 and base assembly 210. In addition to housing portions of plurality of driven assemblies 260 as well as plurality of prostheses 206 (see FIG. 16), front delivery assembly 212 can also include various components to facilitate ease of use and further enhance the functionality of deployment device 202.

With front delivery assembly 212 mounted to base assembly 210, portions of front delivery assembly 212 may be inserted within forward mounting portion 710. In some cases, a portion of cannula 215 may be inserted into an interior of forward mounting portion 710. Likewise, in some cases, end portions of first driven pin 504 and first driven tube 502 may be disposed within forward mounting portion 710. In a similar manner, end portions of second driven tube 506 and second driven pin 508 could also be disposed within forward mounting portion 710. In addition, first end portion 521 of driving tube 520 and first end portion 523 of driving pin 522 may extend through an alignment hole 713 and into forward mounting portion 710. This arrangement may facilitate the alignment of driving tube 520 and driving pin 522 with first driven tube 502 and first driven pin 504, respectively, for example.

As previously mentioned, some embodiments can include provisions for implanting multiple prostheses in an efficient manner. In some cases, front delivery assembly 212 may include provisions that allow a surgeon to align various components of plurality of driven assemblies 260 with driving assembly 250. In some cases, for example, front delivery assembly 212 may include provisions for rotating the positions of some components.

Figure 54:
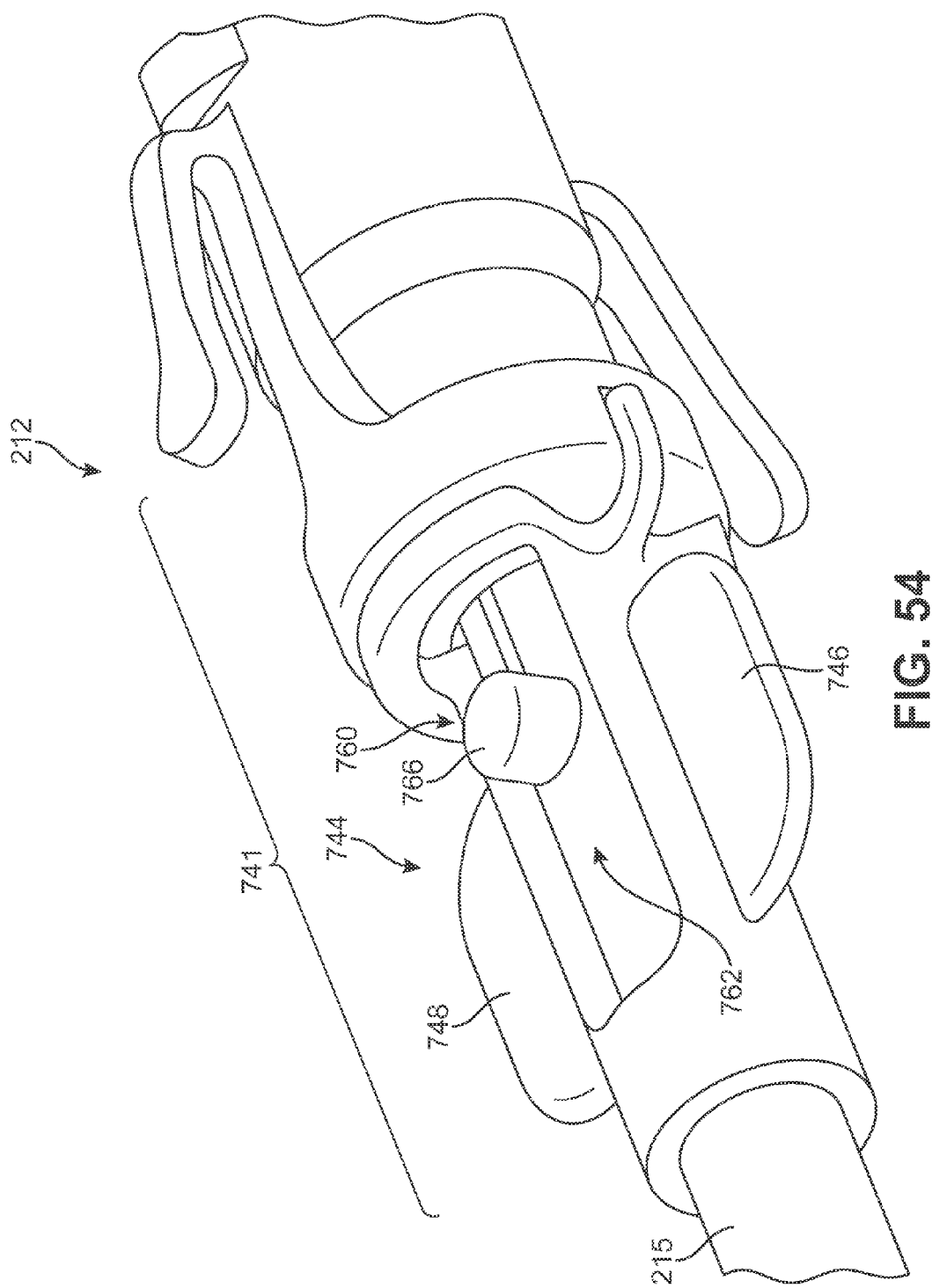
FIG. 54 is a schematic diagram illustrating an isometric view of a portion of a front delivery assembly, which includes a rotating assembly.

FIG. 54 illustrates an enlarged isometric view of portions of front delivery assembly 212, including a rotating assembly 741. Referring to FIG. 54, in some embodiments, rotating assembly 741 could include one or more components that allow a surgeon to rotate the position of plurality of driven assemblies 260. For example, while FIG. 53 is shown with first driven tube 502 and first drive pin 504 positioned to be aligned with driving tube 520 and driving pin 522, front delivery assembly 212 may be adjusted so that second driven tube 506 and second driven pin 508 are aligned with driving tube 520 and driving pin 522 as discussed below. This may allow a single driving assembly 250 to apply driving forces to at least two different sets of driven tubes and driven pins disposed within front delivery system 210.

As seen in FIG. 54, rotating assembly 741 could be mounted around cannula 215. In some embodiments, rotating assembly 741 may be fixedly mounted around cannula 215, so that rotating assembly 741 and cannula 215 are configured to rotate together. Moreover, as plurality of driven assemblies 260 may be fixed in place relative to cannula 215 in some embodiments, plurality of driven assemblies 260 may also be rotated through the use of rotating assembly 741.

In some embodiments, rotating assembly 741 can include rotation control lever 744. In some cases, rotation control lever 744 comprises first lever portion 746 and second lever portion 748. By grasping first lever portion 746 and/or second lever portion 748, a surgeon can apply torque to rotating assembly 741, thereby turning rotating assembly 741 and plurality of driven assemblies 260 to a desired position.

Referring now to FIGS. 53 and 54, front delivery assembly 212 may include retracting assembly 760. In some cases, retracting assembly 760 may comprise first retracting member 762 and second retracting member 764. Each retracting member may include a corresponding retracting slider and driven tube engagement portion. In some cases, first retracting member 762 includes first slider 766 that extends outwardly on front delivery assembly 212. First retracting member 762 may also include first driven tube engaging portion 768. Moreover, first driven tube engaging portion 768 may engage first driven tube control post 770, which extends radially from first driven tube 502. First driven tube control post 770 is able to translate within driven tube control slot 771. With this configuration, as first driven tube 502 is advanced during implantation, first driven tube control post 770 may push first driven tube engaging portion 768. This acts to advance first slider 766. In some cases, as first driven tube control post 770 contacts a forward wall of driven tube control slot 771, first driven tube 502 may be prevented from advancing any further. Following implantation of prosthesis 270 (see FIG. 40), a surgeon may retract first driven tube 502 to the pre-implantation position using first slider 766.

Generally, second retracting member 764 may be configured in a similar manner. In particular, once second driven tube 506 has been aligned with driving assembly 250 (for example, by rotating second driven tube 506 into alignment with driving assembly 250), a second driven tube engaging portion 780 may abut second driven control post 782. As second driven tube 506 is advanced during implantation, second driven control post 782 slides through driven tube control slot 771. Second driven control post 782 further acts to advance second retracting member 764, including second slider 784.

Some embodiments may incorporate provisions that automatically readjust the positions of one or more prostheses as the plurality of driven assemblies 260 is rotated. In some cases, for example, the geometry of forward mounting portion 710 of base portion 210 may help control the advancement and retraction of components of driving assembly 250.

Using this configuration, retracting assembly 760 may serve several purposes that facilitate the efficiency of deployment device 202. First, retracting assembly 760 provides a means for retracting a driven tube and driven pin of plurality of driven assemblies 260 following implantation of a prosthesis. In addition, the sliding portions used to retract a driven tube and driven pin may also function as depth indicators that may be used to determine the approximate depth at which a prosthesis has been implanted.

Figure 55:
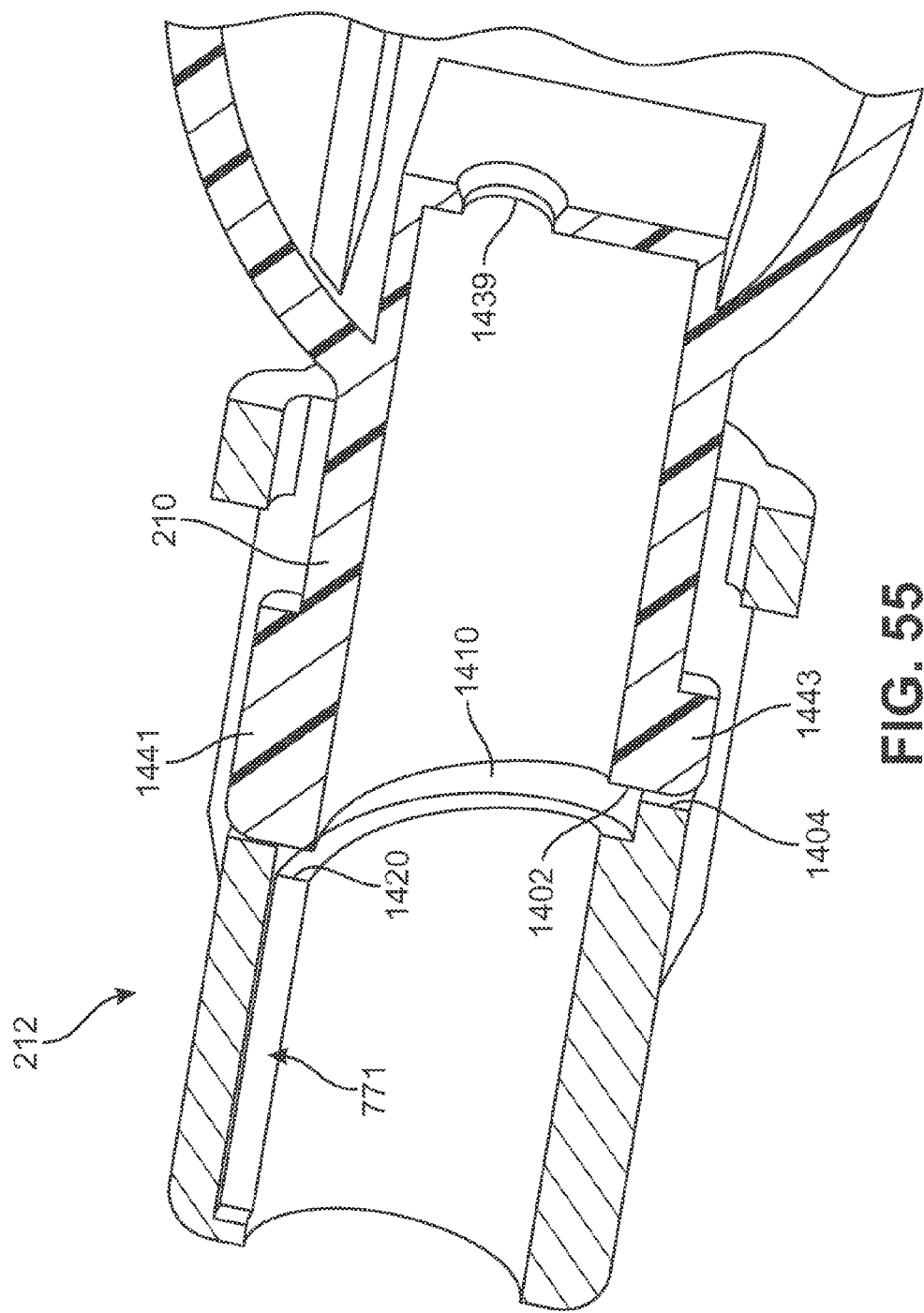
FIG. 55 is a schematic diagram illustrating an isometric cut-away view of a portion of a deployment device according to one embodiment.

FIG. 55 illustrates a schematic isometric cross-sectional view of a portion of base assembly 210 and front assembly 212 for purposes of understanding some features of retracting assembly 760 (see FIG. 53). As seen in FIG. 55, forward edge 1402 of base assembly 210 comprises an approximately helical geometry that matches the approximately helical geometry of interior rearward edge 1404 of front delivery assembly 212. Moreover, front delivery assembly 212 includes an approximately helical rotational slot 1410 that extends between base assembly 210 and front delivery assembly 212. Rotational slot 1410 may be connected with driven tube control slot 771, so that a control post translated to rearward end 1420 of driven tube control slot 771 may be capable of translating through rotational slot 1410. This configuration helps ensure that front delivery assembly 212 may only be rotated when the driven assembly that is aligned with driving assembly 250 (see FIG. 53) is fully retracted, such that the corresponding control post may then move through rotational slot 1410. For example, in the configuration shown in FIG. 53, driven tube control slot 771 may be used to limit and/or prevent the rotation of front delivery assembly 212 until the desired depth is achieved for the current prosthesis, at which time first slider 766 (see FIG. 53) may be retracted to allow rotation.

As seen clearly in FIG. 55, base assembly 210 includes top attachment portion 1441 and bottom attachment portion 1443, which may be configured to facilitate the attachment of front delivery assembly 212 to base portion 210. Furthermore, FIG. 55 also clearly illustrates alignment aperture 1439, which may be contoured to help align a driving assembly. In some cases, alignment aperture 1439 has a contoured geometry that gets narrower in the forwards direction in order to help guide a driving assembly into proper alignment.

A deployment device can include provisions for ensuring a prosthesis is implanted to a desired depth within a tissue for a variety of different conditions. In some embodiments, a deployment device can include provisions for re-applying a driving force to a prosthesis. In some embodiments, a driving assembly may be configured to cycle through an impact cycle two or more times in order to implant a prosthesis to a desired depth.

FIGS. 56 through 60 illustrate schematic views intended to depict a scenario in which two impact cycles are required to fully drive a prosthesis into a tissue. For purposes of illustration, tissue 1300 is shown schematically in these figures, though it should be understood that tissue 1300 could be any kind of tissue including, for example, skin, bone, muscle, or any other kinds of tissue.

Figure 56:
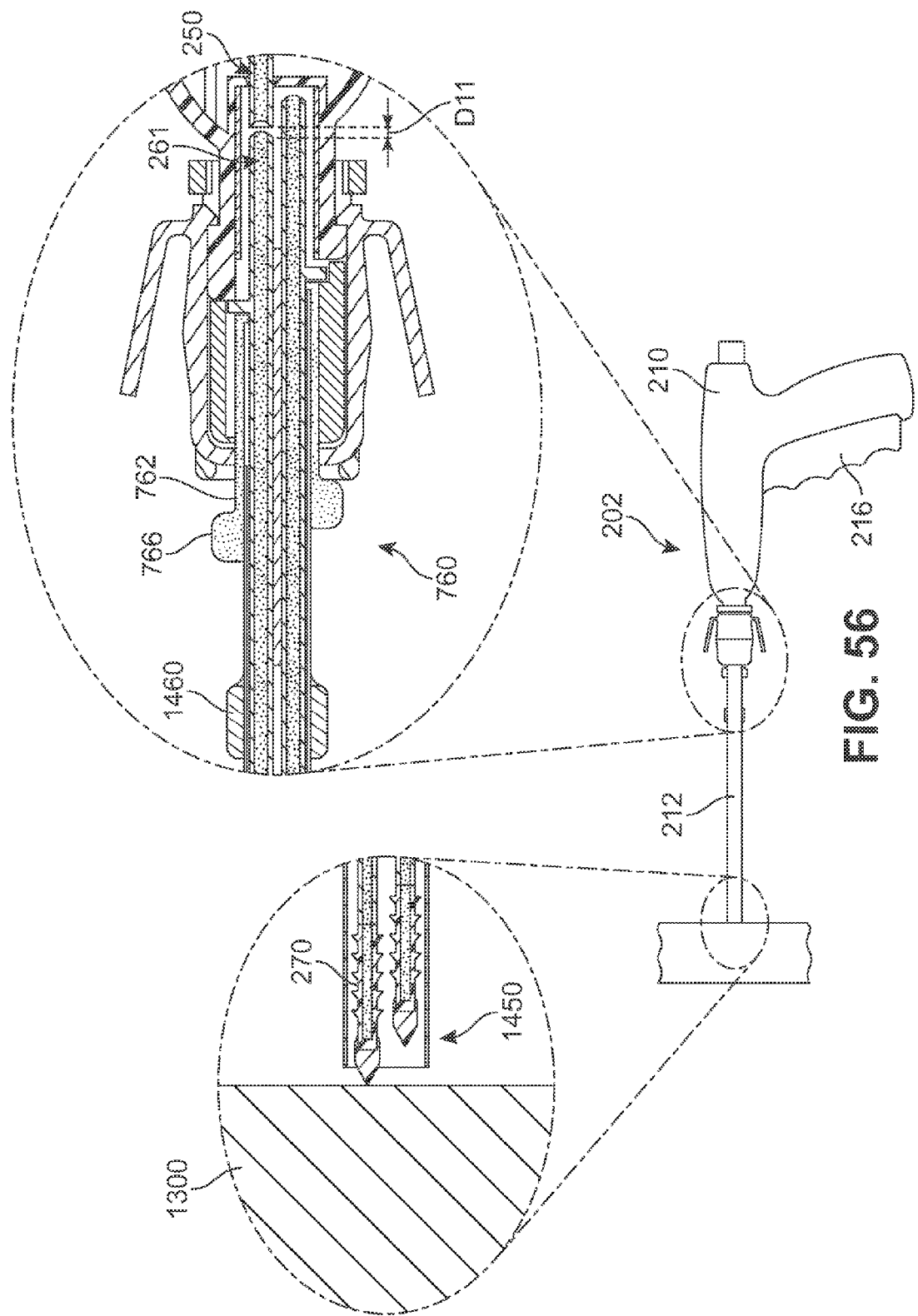
FIG. 56 is a schematic diagram illustrating a detailed side view of an embodiment of a deployment device in a pre-deployment state.

Referring first to FIG. 56, deployment device 202 is in an initial or pre-deployment state. In this state, first prosthesis 270 and first driven assembly 261 are aligned with driving assembly 250, but have not been engaged by driving assembly 250. In this initial state, first driven assembly 261 and driving assembly 250 are separated by a distance D11. Moreover, in this initial state, first retracting member 762 may be disposed in a rearward-most position.

Figure 57:
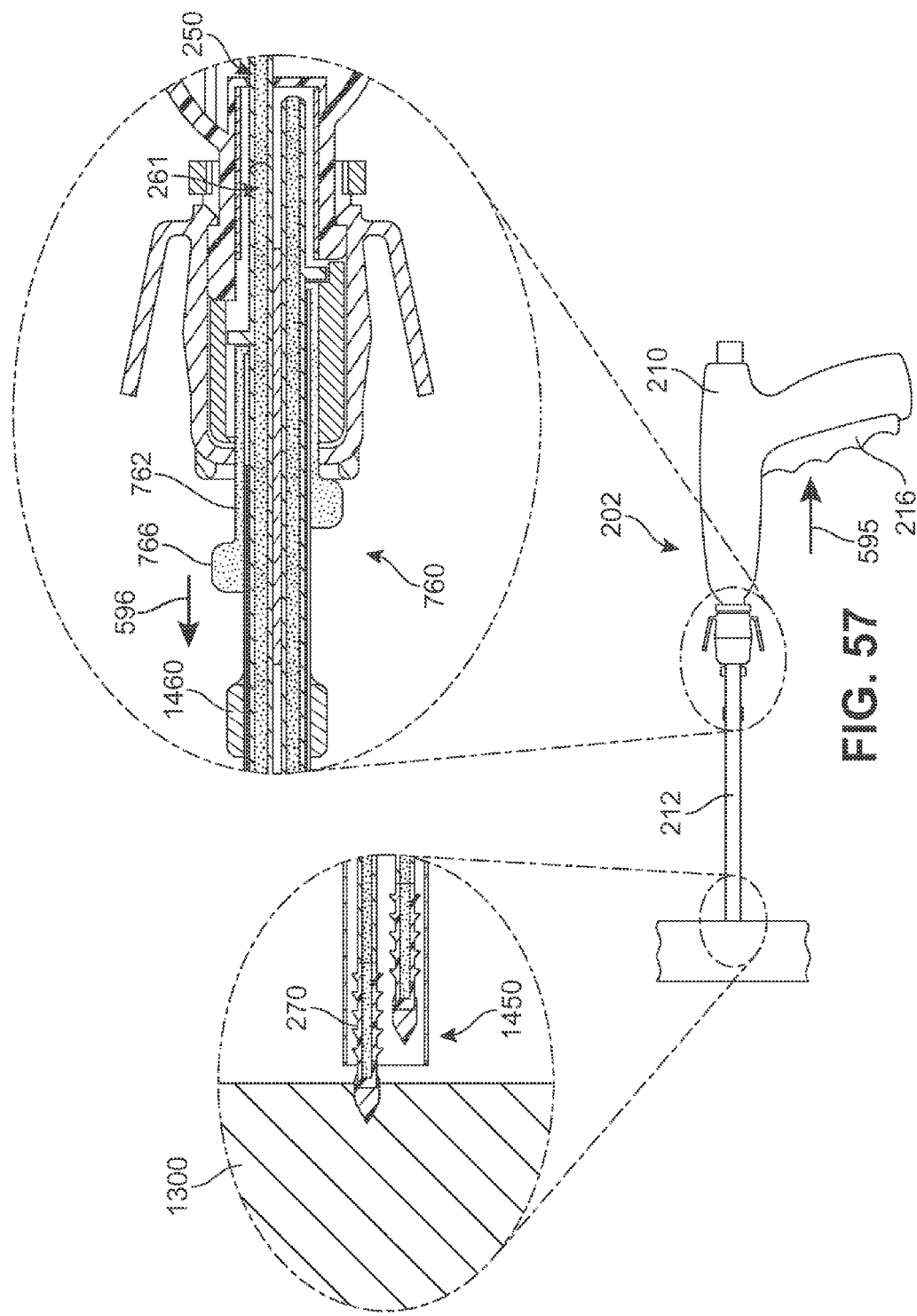
FIG. 57 is a schematic diagram of the deployment device of FIG. 56, in which the prosthesis is being driven into a tissue.
Figure 58:
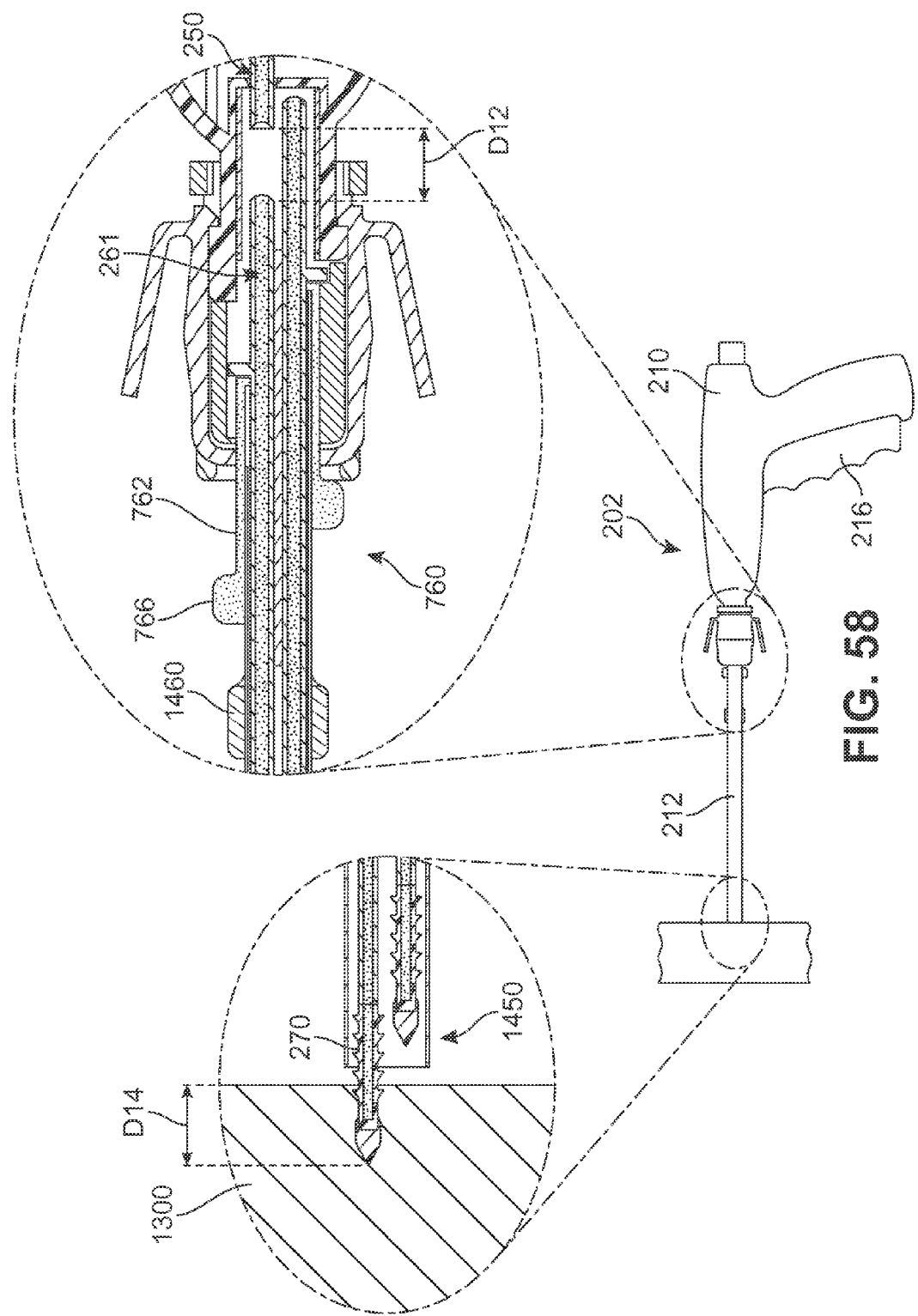
FIG. 58 is a schematic diagram of the deployment device of FIG. 57, in which the prosthesis has been partially implanted into the tissue.

Referring next to FIG. 57, as trigger portion 216 is squeezed in a direction represented by arrow 595, driving assembly 250 may proceed through an impacting cycle, as described above, which results in an impact between driving assembly 250 and first driven assembly 261. This impact displaces first driven assembly 261 and provides enough force to begin implanting first prosthesis 270 into tissue 1300. Moreover, as previously mentioned, the motion of first driven assembly 261 may cause first retracting member 762 to similarly move forwards, as represented by arrow 596. As seen in FIG. 58, when the impact cycle has completed, driving assembly 250 may return to a default position. In this intermediate state of deployment device 202 where driving assembly 250 is at rest, driving assembly 250 and first driven assembly 261 may be separated by a distance D12. Furthermore, first prosthesis 270 has been driven a distance D14 into tissue 1300. As seen by comparing FIGS. 56 and 58, distance D12 is substantially greater than distance D11. In other words, following the initial impact cycle of driving assembly 250, first driven assembly 261 and driving assembly 250 are spaced farther apart from one another than the initial spacing.

As seen in FIG. 58, first prosthesis 270 has not been fully implanted into tissue 1300. This may occur, for example, when tissue 1300 is bone having a relatively high density. In this case, the amount of energy required to completely implant prosthesis 270 may be greater than the amount of energy supplied by driving assembly 250 during one impact cycle.

To ensure that prosthesis 270 is fully implanted, driving assembly 250 may be actuated a second time so that driving assembly 250 undergoes a second impact cycle during which a second impact between driving assembly 250 and first driven assembly 261 serves to further drive prosthesis 270 into tissue 1300.

Figure 59:
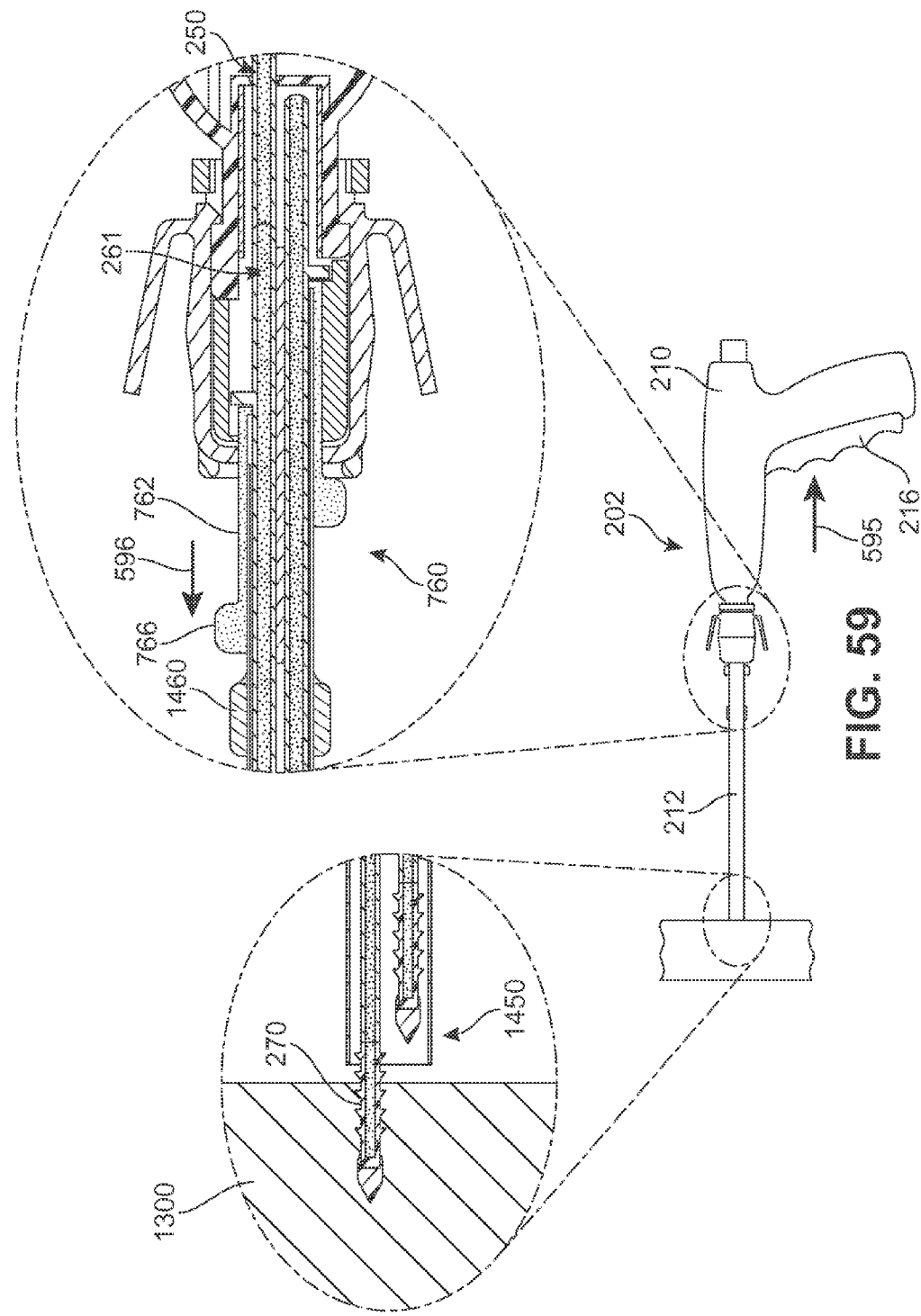
FIG. 59 is a schematic diagram of the deployment device of FIG. 58, in which the prosthesis is being driven further into the tissue.
Figure 60:
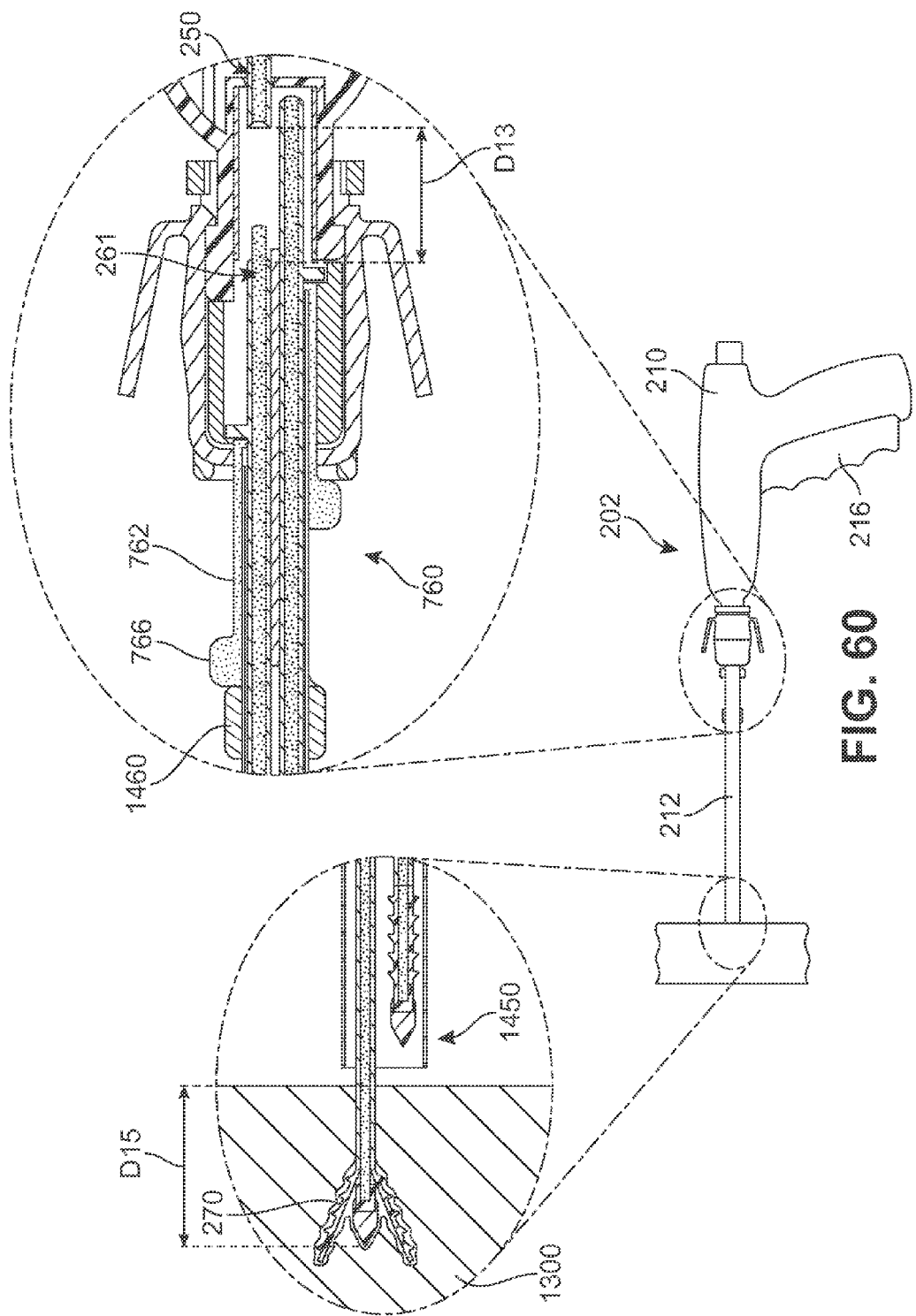
FIG. 60 is a schematic diagram of the deployment device of FIG. 59, in which the prosthesis is fully driven into the tissue.

Referring to FIG. 59, driving assembly 250 re-impacts first driven assembly 261 as a surgeon depresses trigger portion 216 a second time (represented by arrow 595). As previously mentioned, first retracting member 762 may also translate in a forward direction represented by arrow 596, as first driven assembly 261 is impacted and moves forwards. The result of these two sequential impacts on first driven assembly 261 is to fully drive first prosthesis 270 into tissue 1300, as seen in FIG. 60. In this final state of deployment device 202 where driving assembly 250 is at rest, driving assembly 250 and first driven assembly 261 may be separated by a distance D13. Furthermore, first prosthesis 270 has been driven a distance D15 into tissue 1300. As seen by comparing FIGS. 58 and 60, distance D13 is substantially greater than distance D12. In other words, the relative spacing between driving assembly 250 and first driven assembly 261 increases with each successive impact cycle. Moreover, distance D15 is substantially greater than distance D14 and in particular, distance D15 may approximately correspond to the desired implantation depth of prosthesis 270.

Referring to FIGS. 56 through 60, the depth at which prosthesis 270 has been inserted into a tissue may be obscured by front end portion 1450 of front delivery assembly 212, as well as possibly by features of the surgical environment (for example, skin, other tissue, etc.). Therefore, in order to determine if prosthesis 270 has been implanted to the desired depth, a surgeon may make use of first retracting member 762 and in particular the position of first slider 766 to determine the depth of prosthesis 270. For example, referring to the state of deployment device 202 in FIG. 58, a surgeon may see that first slider 766 has not yet reached, or is spaced apart from, its final position adjacent to forward portion 1460 of retracting assembly 760. At this point, a surgeon may decide to squeeze trigger portion 216 a second time, thereby actuating driving assembly 250 again in order to re-impact first driven assembly 261 and thereby drive first prosthesis 270 further into tissue 1300. In the final state, shown in FIG. 60, the surgeon may see that first slider 766 has reached a final predetermined position that is adjacent to forward portion 1460, which indicates that prosthesis 270 has been implanted to the desired depth within tissue 1300.

As seen in FIG. 60, prosthesis 270 (see FIG. 56) may expand at the end of the implantation sequence. As previously described, prosthesis 270 may expand when driving tube 520 begins to translate relative to driving pin 522, which causes first driven tube 502 to translate relative to first driven pin 504. Therefore, the expansion of prosthesis 270 may be associated with a segment of the full range of motion of driving tube 520. In this case, the distance traveled by both driving tube 520 and first retracting member 762 during the impact cycle may be substantially greater than the implantation depth of prosthesis 270.

The current embodiment illustrates an embodiment that requires two impact cycles to fully implant prosthesis 270 into tissue 1300. However, it should be understood that the embodiments allow for any number of impact cycles to be achieved so that a surgeon can engage trigger assembly 216 as many times as are needed to fully implant a prosthesis.

Using the configuration described here, deployment device 202 may be configured so that driving assembly 250 undergoes a full impact cycle even when a prosthesis is only partially driven into a tissue, as could occur if the prosthesis is driven into a high density tissue. In other words, driving assembly 250 is configured to undergo substantially similar motions associated with an energy storage stage and a driving stage each time that trigger portion 216 is engaged by the surgeon and these motions may be substantially independent of the depth that the prosthesis is driven into a tissue. This helps ensure consistent operation of deployment device 202 between successive impacts of the prosthesis for a variety of implanting conditions, such as various possible densities of the implanting tissue.

FIGS. 61 through 63 illustrate schematic views of the operation of an embodiment of rotating assembly 741 as it facilitates the implantation of multiple prostheses in quick succession. In particular, FIG. 61 illustrates a schematic view of an initial position of rotating assembly 741 following implantation of a first prosthesis 270. FIG. 62 illustrates a schematic view of an intermediate position of rotating assembly 741 as a second prosthesis is repositioned. FIG. 63 illustrates a schematic view of rotating assembly 741 in a final position in which second prosthesis 272 can be implanted. Although the current embodiment illustrates an example in which two prostheses may be implanted, it will be understood that other embodiments could incorporate multiple prostheses in a single front delivery assembly. Moreover, straightforward modifications to rotating assembly 741 could be made to house and allow for the implantation of three or more prostheses.

Referring first to FIG. 61, first prosthesis 270 has been implanted into tissue 800. At this point, first driven tube 502 is fully advanced. In order to implant second prosthesis 272, plurality of driven assemblies 260 may be adjusted so that second driven tube 506 and second driven pin 508 are aligned with driving tube 520 and driving pin 522. As seen in FIG. 62, this realignment may be accomplished by engaging rotating assembly 741. In some embodiments, rotation control lever 744 is used to rotate driving assembly 260. Using control lever 744, portions of front delivery assembly 212 may be rotated in a direction represented by arrows 598 or in a direction opposite of the direction represented by arrows 598. Referring now to FIG. 63, rotating assembly 741 has been turned approximately 180 degrees from the initial position shown in FIG. 61. In this final rotated position, second driven tube 506 and second driven pin 508 may be aligned with driving tube 520 and driving pin 522. In this position, second driven tube 506 and second driven pin 508 can be engaged by driving tube 520 and driving pin 522 in order to implant second prosthesis 272 into tissue 800.

Using the arrangement described here, the components of plurality of driven assemblies 260 may be associated with at least two different configurations. In a first configuration, shown for example in FIGS. 53 and 61, first driven tube 502 and first driven pin 504 may be aligned with driving tube 520 and driving pin 522, respectively. Also, in this first configuration, first prosthesis 270 may generally be aligned with driving tube 520 and driving pin 522. In a second configuration, shown for example in FIG. 63, second driven tube 506 and second driven pin 508 may be aligned with driving tube 520 and driving pin 522, respectively. Also, in this second configuration, second prosthesis 272 may generally be aligned with driving tube 520 and driving pin 522. Moreover, using rotation control lever 744 (see FIG. 62) allows a surgeon to rotate these components between the first configuration and the second configuration.

The arrangement described above allows a plurality of prostheses to be housed within front delivery assembly 212. Moreover, each prosthesis may be disposed in either a driving position, in which the prosthesis is aligned with driving assembly 250 (see FIG. 53), or a storage position, in which the prosthesis is out of alignment with driving assembly 250. Furthermore, in some embodiments, only one prosthesis may be in the driving position. However, for configurations incorporating three or more prostheses within front delivery device 212, two or more prostheses could be in the storage position simultaneously. Thus, front delivery assembly 212 may provide a prosthesis configured for immediate implantation, and may also provide storage for one or more prostheses.

As seen in FIGS. 61 through 63, the process of adjusting second prosthesis 272 from the storage position to the driving position includes rotating front delivery assembly 212 about its own central longitudinal axis 599. Moreover, front delivery assembly 212 is rotated with respect to base assembly 210, which stays in place within the surgeon's hand as the position of second prosthesis 272 is adjusted. Thus, the driving position and the storage position may be characterized as angularly displaced from one another with respect to central longitudinal axis 599 of front delivery assembly 212.

As seen in the enlarged cut-away views included in FIGS. 61 through 63, first prosthesis 270 and second prosthesis 272 may be connected by suture thread 830. Following the insertion of first prosthesis 270, suture thread 830 may remain taut against a side of first prosthesis 270 and may extend back to second prosthesis 272, which is still housed within cannula 215 at this stage. Once second prosthesis 272 is implanted within tissue 800, as seen in FIG. 63, suture thread 830 may be pulled taut along the surface of tissue 830, anchored in place by first prosthesis 270 and second prosthesis 272.

FIGS. 61 through 63 further illustrate indentation 989 of rotating assembly 741. In some embodiments, indentation 989 may be configured to receive first flange portion 991 or second flange portion 993. As front delivery assembly 212 is rotated, first flange portion 991 and second flange portion 993 may rotate, while indentation 989 is fixed in place. Moreover, indentation 989 may be positioned such that first flange portion 991 or second flange portion 993 is received in indentation 989 when either of driven assemblies 260 are aligned with driving tube 520 and driving pin 522. First flange portion 991 and second flange portion 993 may engage indentation 989 in a manner that helps to resist accidental rotation of front delivery assembly 212. Although only one indentation is visible in FIGS. 61 through 63, it should be understood that some embodiments can include at least two corresponding indentations, such as having a pair of indentations disposed 180 degrees apart from one another about central longitudinal axis 599 that both receive either first flange portion 991 or second flange portion 993.

Figure 64:
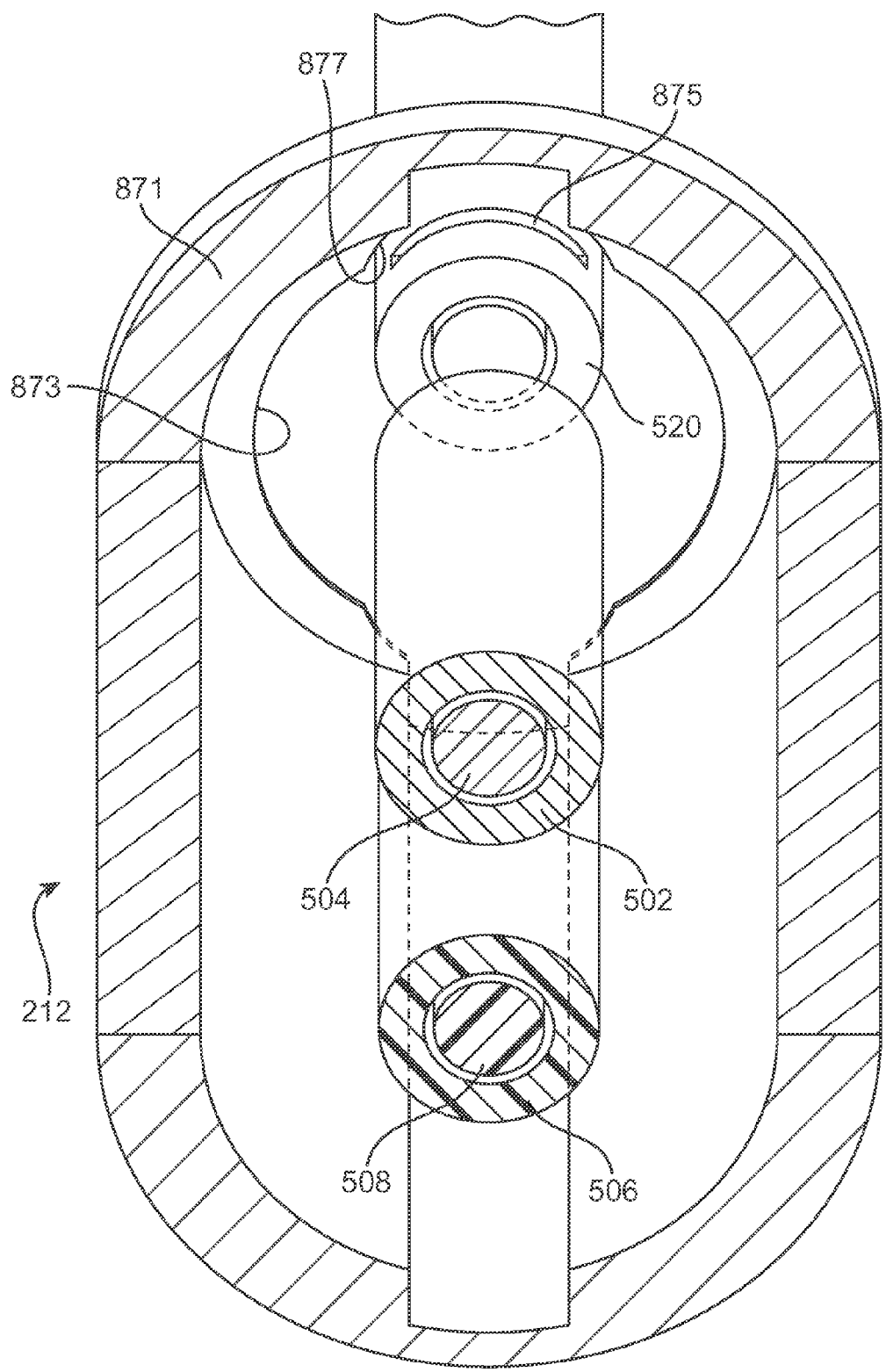
FIG. 64 is a schematic cut-away diagram of a portion of a front delivery assembly, in which the top half of the front delivery assembly has been removed forwards of a locking ring, and which further illustrates the locking ring in a ready to actuate position according to an embodiment.
Figure 65:
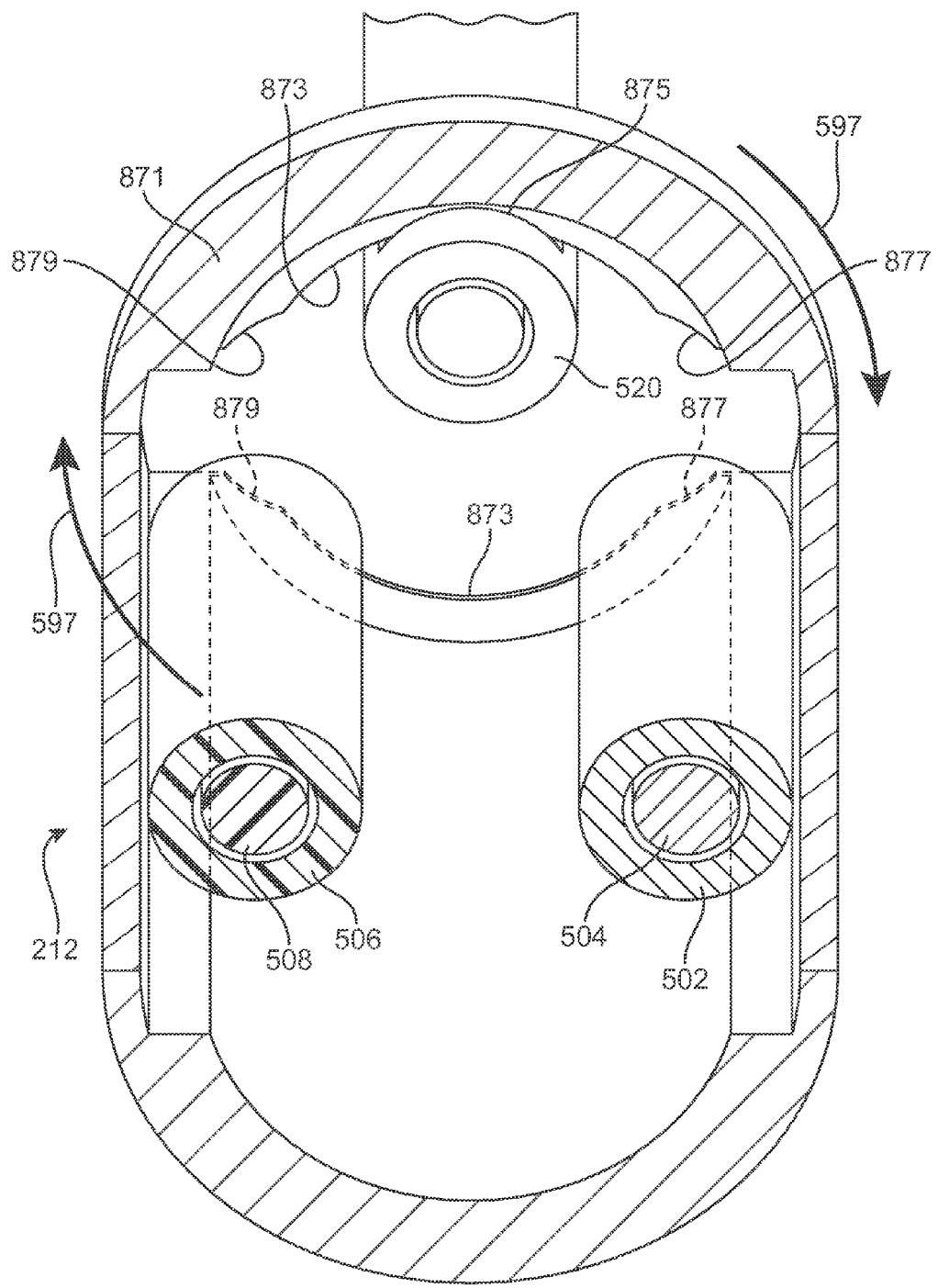
FIG. 65 is a schematic cut-away diagram illustrating the locking ring of FIG. 64 in a locked out position according to an embodiment.

FIGS. 64 and 65 illustrate schematic cut-away views of a portion of front delivery assembly 212 for the purposes of showing the relationship of various components of front delivery assembly 212. The specific views shown in FIGS. 64 and 65 illustrate a region where driving tube 520 enters front delivery assembly 212. Moreover, the cut-away view seen in FIGS. 64 and 65 is taken such that a top half of front delivery assembly 212 (specifically, the top half of cannula 215 that is shown in FIG. 53) has been removed forwards of a locking member 871. Locking member 871 is described in detail below, and in some embodiments it may generally form a rearward end of cannula 215.

Referring to FIGS. 64 and 65, some embodiments can include provisions to help prevent unintentional actuation of a deployment device. In some embodiments, front delivery assembly 212 may include locking member 871. Locking member 871 may comprise a ring-like member including an inner edge 873 that defines an inner diameter for locking member 871. In some cases, inner edge 873 is designed to engage locking groove 875 of driving tube 520. Moreover, locking member 871 may include first gap 877 and second gap 879. When either first gap 877 or second gap 879 are disposed directly over driving tube 520, driving tube 520 is free to translate axially. However, should locking member 871 be rotated to any other angular position (for example, any angular position where first driven tube 502 or second driven tube 506 are out of alignment with driving tube 520), inner edge 873 engages locking groove 875 and prevents axial movement of driving tube 520. For example, FIG. 65 illustrates a configuration where front delivery assembly 212 has been rotated in a direction represented by arrows 597 so that inner edge 873 is engaged with locking groove 875. This state may be described as a locked-out state, in which driving tube 520 is locked and unable to translate. This is in contrast to the ready to actuate state of FIG. 64, where driving tube 520 is free to translate and impact a driven tube. This arrangement may help ensure that driving tube 520 is not accidentally actuated while front delivery assembly 212 is disposed in an intermediate position where neither of the two driving assemblies are properly aligned with driving tube 520.

Figure 66:
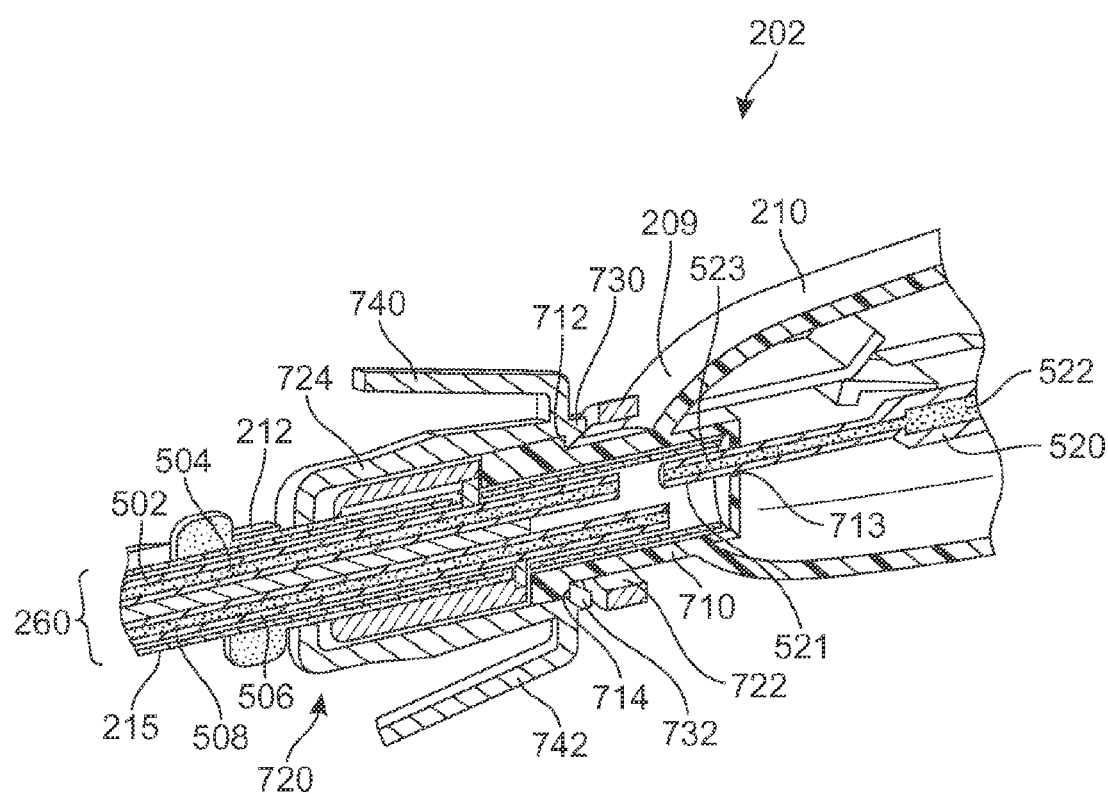
FIG. 66 is a schematic diagram illustrating an isometric cut-away view of a portion of a deployment device according to one embodiment, in which a front delivery assembly is attached to a base assembly.

FIG. 66 illustrates another cut-away view of portions of front delivery assembly and base portion 210. Referring to FIG. 66, in some embodiments, front delivery assembly 212 may be mounted to forward portion 209 of base assembly 210, rather than being integrally formed with base assembly 210. In order to receive front delivery assembly 212, in some cases base assembly 210 can include forward mounting portion 710. In some embodiments, forward mounting portion 710 may be a tube-like portion. Additionally, forward mounting portion 710 may include upper mounting shoulder 712 and lower mounting shoulder 714. In some cases, upper mounting shoulder 712 and lower mounting shoulder 714 may be formed by varying the radial thickness of forward mounting portion 710. Also, the end surfaces between forward mounting portion 710 and second mounting portion 724 of mounting assembly 720 are contoured to facilitate the axial movement of the driven assemblies 260 from the storage position to the deployed position.

In some embodiments, front delivery assembly 212 may include mounting assembly 720 that includes provisions for mounting front delivery assembly 212 to base assembly 210 at forward mounting portion 710. In some cases, mounting assembly 720 may further include first mounting portion 722 and second mounting portion 724 (also shown in FIG. 67). In some cases, first mounting portion 722 may be sized and shaped to slide over an exterior surface of forward mounting portion 710. In addition, second mounting portion 724 may include one or more fastening portions. In one embodiment, second mounting portion 724 may include first fastening portion 730 and second fastening portion 732. In some cases, first fastening portion 730 and second fastening portion 732 may be configured to engage upper mounting shoulder 712 or lower mounting shoulder 714, respectively. In some cases, first fastening portion 730 and second fastening portion 732 comprise snap hooks that rest against upper mounting shoulder 712 and lower mounting shoulder 714, respectively. This configuration helps to prevent front delivery assembly 212 from disengaging with base assembly 210 during use.

Some embodiments may include provisions to facilitate easy detachment of front delivery assembly 212 from base assembly 210. In some embodiments, mounting assembly 720 may include a release mechanism. In some embodiments, second mounting portion 724 may include one or more release levers. In one embodiment, second mounting portion 724 includes first release lever 740 that is associated with first fastening portion 730. Additionally, second mounting portion 724 may include second release lever 742 that is associated with second fastening portion 732. As described in further detail below, first release lever 740 and second release lever 742 may be depressed by a surgeon in order to disengage first fastening portion 730 and second fastening portion 732, respectively, from forward mounting portion 710 of base portion 210.

The particular features described here for detachably mounting front delivery assembly 212 with base assembly 210 are intended to be exemplary. It should therefore be understood that other embodiments of deployment device 202 can include any other means for detachably mounting front delivery assembly 212 with base assembly 210. Other embodiments could utilize one or more removable fasteners that help to detachably mount front delivery assembly 212 with base assembly 210. In one alternative embodiment, for example, front delivery assembly 212 and base assembly 210 could comprise corresponding threading and thread receiving portions that would provide for front delivery assembly 212 to be screwed onto base assembly 210.

Figure 67:
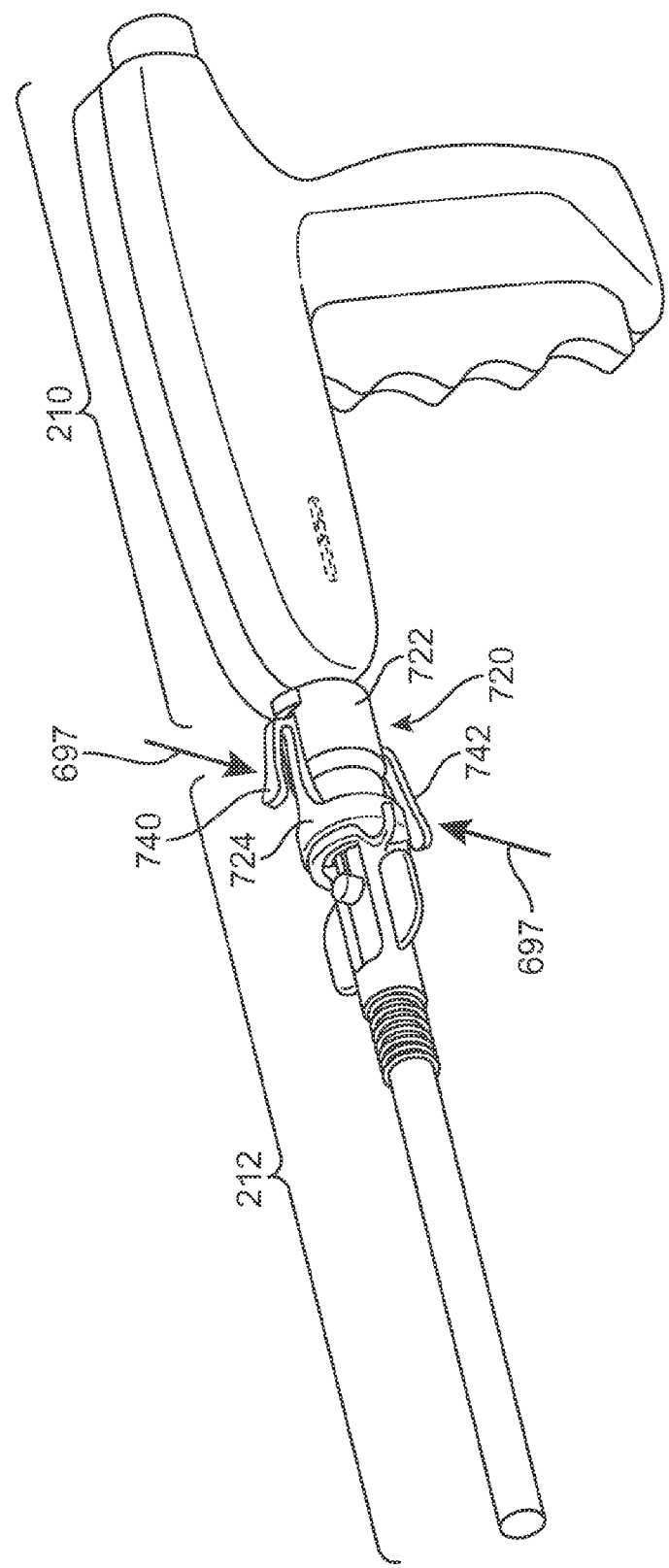
FIG. 67 is a schematic diagram illustrating the location where a surgeon may apply a force to remove a front delivery assembly from a base assembly according to one embodiment.
Figure 68:
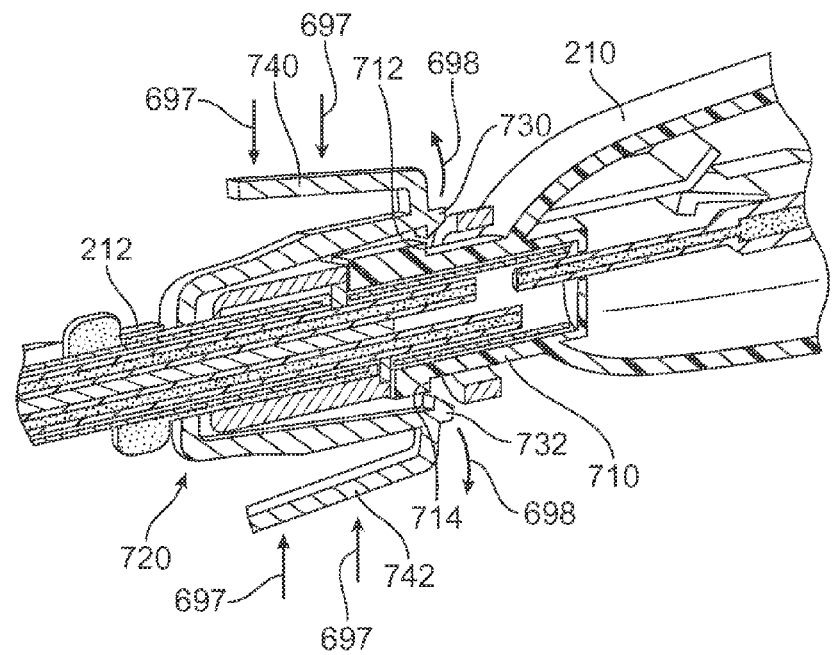
FIG. 68 is a schematic diagram illustrating an isometric cut-away view of a portion of the deployment device of FIG. 66 as a front delivery assembly has started to disengage from a base assembly.
Figure 69:
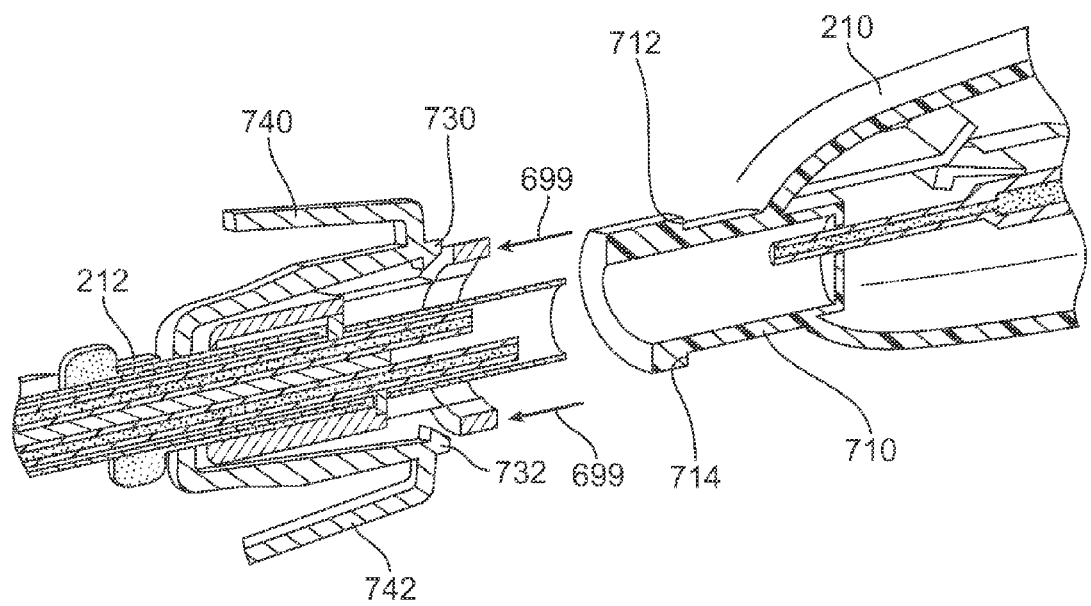
FIG. 69 is a schematic diagram illustrating an isometric cut-away view of a portion of the deployment device of FIG. 66 as a front delivery assembly has been fully disengaged from a base assembly.

FIGS. 67 through 69 illustrate isometric views of a process of detaching front delivery assembly 212 from base assembly 210, according to one embodiment. In order to detach front delivery assembly 212 a surgeon may depress first release lever 740 and second release lever 742, as represented by arrows 697 in FIGS. 67 and 68. As seen in FIG. 68, as first release lever 740 and second release lever 742 are depressed, first fastening portion 730 and second fastening portion 732 may be released from engagement with upper mounting shoulder 712 and lower mounting shoulder 714, respectively, which is represented schematically by arrows 698. At this point, a surgeon is able to pull mounting assembly 720 off of forward mounting portion 710, thereby separating front delivery assembly 212 and base assembly 210, as shown in FIG. 69. Here, the motion of front delivery assembly 212 away from base assembly 210 is represented by arrows 699. Of course, a similar process in reverse order (not shown) could be used to attach front delivery assembly 212 and base assembly 210.

The embodiments described above allow for a detachable front delivery assembly 212 to be used with base assembly 210. To enhance the ease of use, some embodiments may include provisions for associating multiple different front delivery systems with a single base assembly. In particular, some embodiments may make use of multiple front delivery assemblies that may be disposed of after use. This may improve ease of use by removing potentially cumbersome steps of replacing individual prostheses and/or driven assemblies within a front delivery assembly.

Some of the components described above for a front delivery assembly could be optional. In some embodiments, for example, one or more driven assemblies could be optional. In one such alternative embodiment, a detachable front delivery assembly may be configured to house one or more prostheses but may not include any driven assemblies. In such an embodiment it is contemplated that the prostheses of the front delivery assembly may be directly associated with a driving assembly of a deployment device. For example, one such embodiment of a front delivery assembly could include an arrangement such that first prosthesis 270 and second prosthesis 272 may be directly aligned with, and configured to be directly driven by, driving assembly 250 of base assembly 210 (see FIGS. 15 and 16). In such an embodiment, the front delivery assembly could be significantly shorter than front delivery assembly 212 described above, to ensure that first prosthesis 270 and second prosthesis 272 are capable of direct contact with driving assembly 250. Furthermore, it will be understood that such alternative embodiments could incorporate additional changes to accommodate other constraints imposed by the removal of one or more driven assemblies. For example, in the alternative embodiment described here, the step or steps of associating first prosthesis 270 or second prosthesis 272 with driving assembly 250 may further include a step of inserting driving pin 522 into a corresponding longitudinal cavity of first prosthesis 270 or second prosthesis 272 prior to implantation. This additional step may help ensure that driving tube 520 and driving pin 522 provide the desired impacting forces on a driving portion and a base portion, respectively, of a prosthesis during the first stage of implantation.

Figure 70:
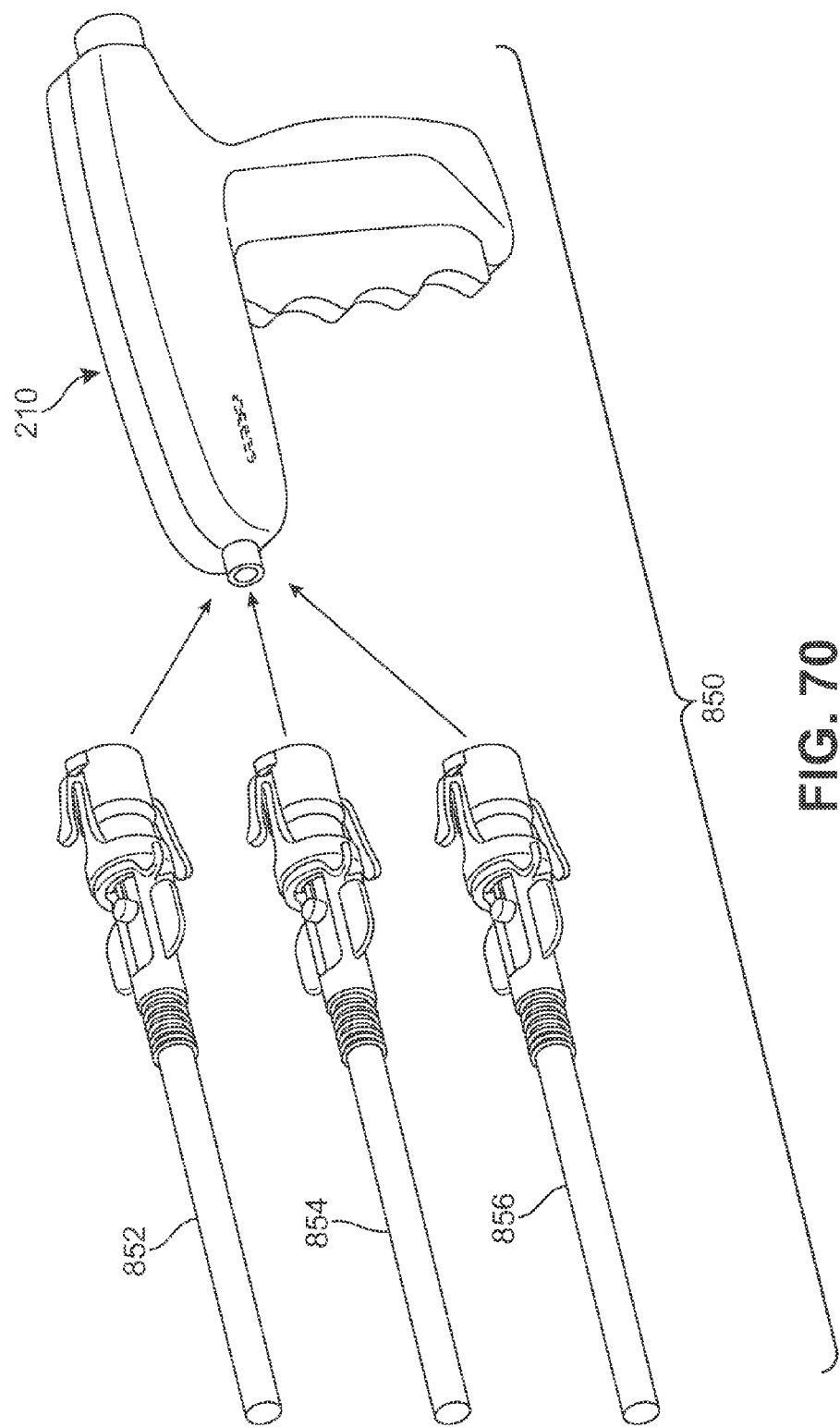
FIG. 70 is a schematic diagram illustrating a schematic view of an embodiment of a kit of parts including a base assembly and a plurality of front delivery assemblies.

FIG. 70 illustrates a schematic view of an exemplary embodiment of kit of parts 850 that comprises various interchangeable front delivery assemblies for use with a single base assembly 210. Referring to FIG. 70, kit of parts 850 may include first front delivery assembly 852, second front delivery assembly 854, and third front delivery assembly 856. Each assembly could be interchangeably used with base assembly 210.

In some embodiments, each of first front delivery assembly 852, second front delivery assembly 854 and third front delivery assembly 856 may be substantially identical. For example, each of first front delivery assembly 852, second front delivery assembly 854, and third front delivery assembly 856 could incorporate similar components including the same number of prostheses for implantation. In other embodiments, however, two or more of first front delivery assembly 852, second front delivery assembly 854, and third front delivery assembly 856 could differ in some aspect including the number of prostheses. For example, one kit could include a front delivery assembly including two prostheses, another front delivery assembly including three prostheses, and still another front delivery assembly including four prostheses.

The kit of parts 850 described here may allow for more flexibility in repairing various forms of tissue imperfections during surgery. Different sterile and prepackaged front delivery assemblies could vary in provisions, including, but not limited to, suture types, suture lengths, anchor types, anchor sizes, anchor materials, anchor number, canula size, canula depth, as well as other features. During surgery, a surgeon may select the most desirable front delivery assembly based on conditions encountered during surgery, rather than relying on a single configuration for a deployment device that is determined using only pre-surgical information. For example, this may allow a surgeon to increase the number of available prostheses for repairing an imperfection based on surgery conditions. Likewise, this may allow a surgeon to change the type or material of prostheses to be used in a repair based on surgery conditions. In each case, a surgeon can simply interchange the currently attached front delivery assembly with a more suitable front delivery assembly according to surgery conditions.

It is contemplated that a method of providing a deployment device to customers could incorporate providing a kit of parts including a single base assembly as well as two or more front delivery assemblies. In terms of retail considerations, in some cases, an intended surgeon could purchase a kit including the base assembly as well as multiple front delivery assemblies. In other cases, some components could be sold separately while still being intended for use together.

A detachable front assembly can include provisions to hold tissue in place prior to implanting one or more prostheses. In some embodiments, for example, a detachable front assembly can include one or more holding members. In some embodiments, a holding member could comprise a pin-like projection that acts to position and/or hold down a tendon and/or muscle over a particular location of a bone. In one embodiment, a holding member could be used to position and/or hold down a portion of a rotator cuff tendon that is being positioned for reattachment to an underlying bone.

Figure 71:
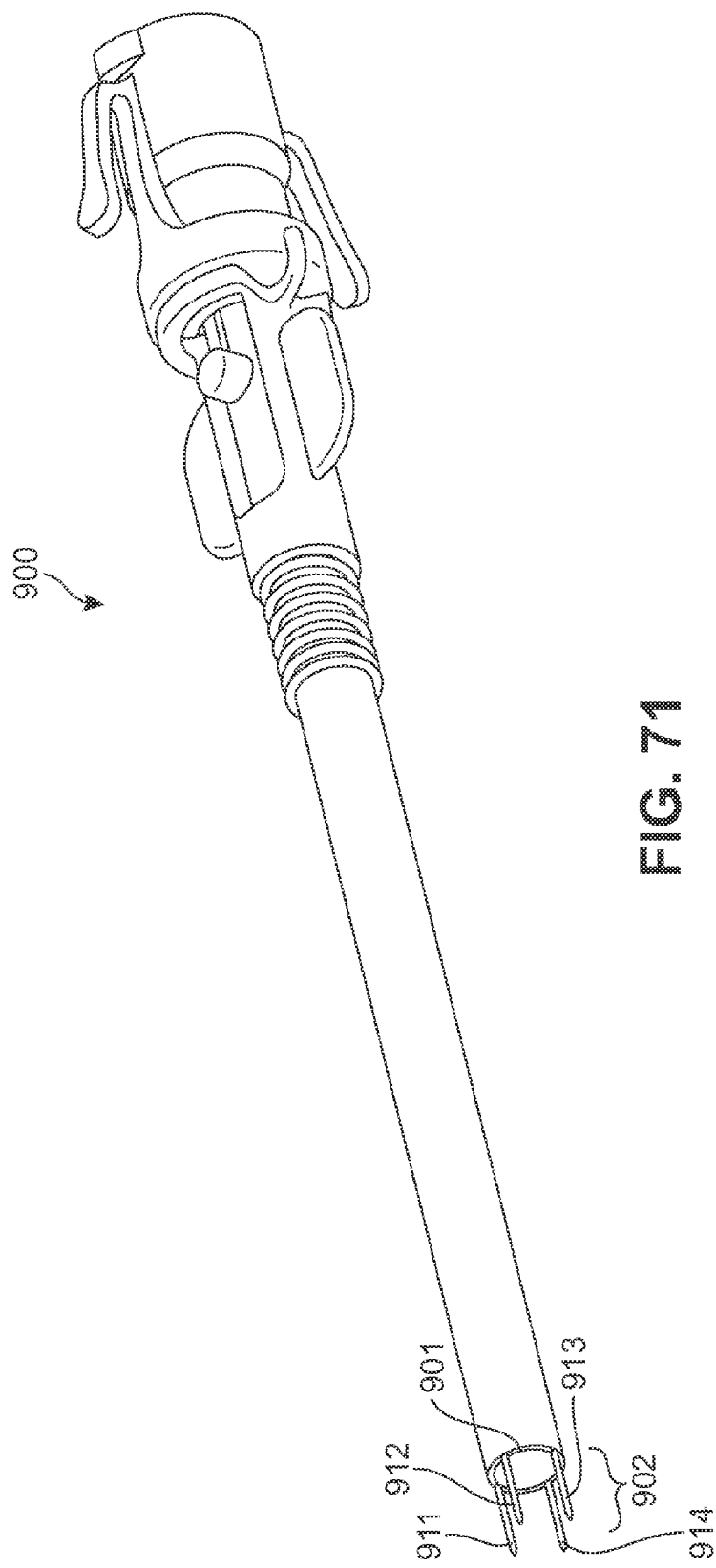
FIG. 71 is a schematic diagram illustrating an isometric view of an embodiment of a front delivery assembly including a plurality of holding members.
Figure 72:
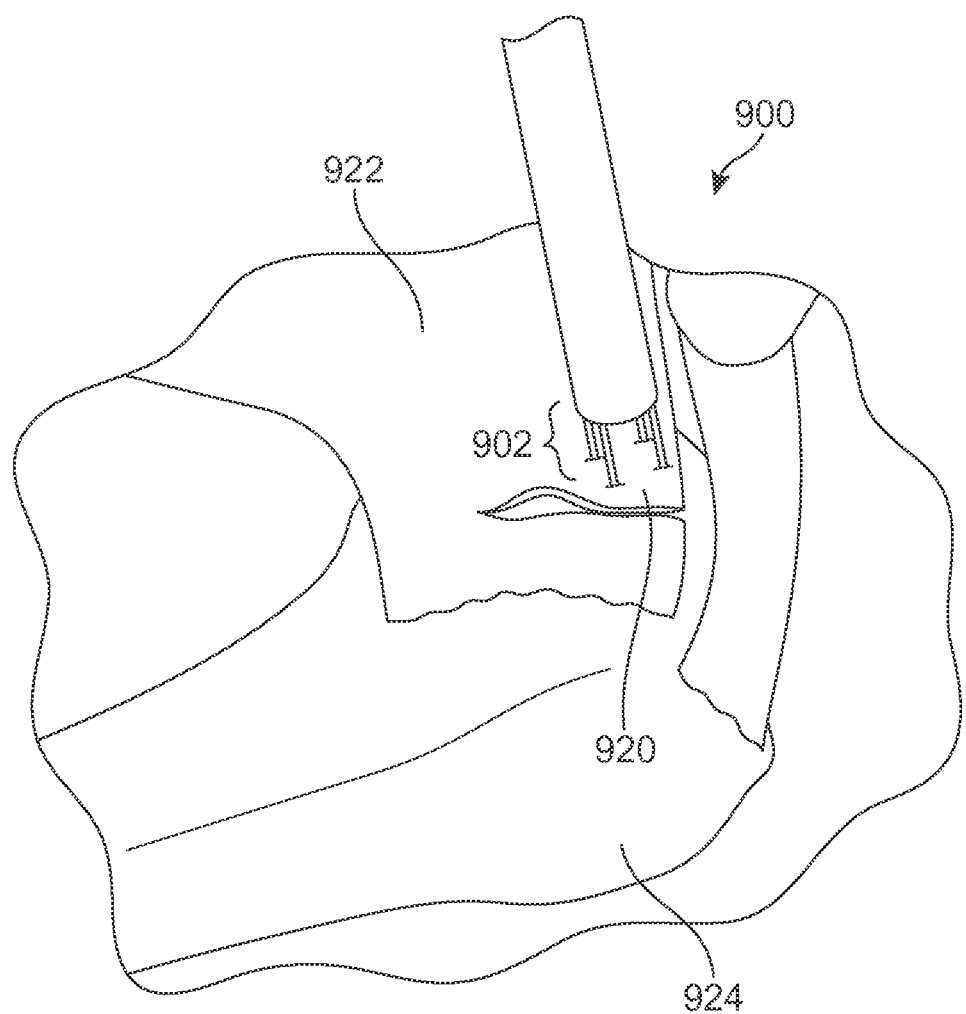
FIG. 72 is a schematic diagram illustrating a possible use for holding members of a front delivery assembly according to one embodiment.

FIGS. 71 and 72 illustrate schematic views of an embodiment of a detachable front system 900 that includes plurality of holding members 902. In some embodiments, plurality of holding members 902 may comprise four individual holding members including first holding member 911, second holding member 912, third holding member 913, and fourth holding member 914. Each of first holding member 911, second holding member 912, third holding member 913, and fourth holding member 914 may be shaped and aligned in a manner that facilitates holding down a tendon or other type of tissue in place over a bone. Moreover, each of first holding member 911, second holding member 912, third holding member 913, and fourth holding member 914 may extend outwardly from forward rim 901 of detachable front delivery system 900.

As seen in FIG. 72, plurality of holding members 902 may be used to pin down portion 920 tendon 922 in a predetermined location of bone 924. As portion 920 may be a portion that of tendon 922 that requires reattachment, plurality of holding members 902 may act to keep portion 920 in place and thereby prevent the natural contraction or recession of portion 920 away from the desired location on bone 924. With this arrangement, a surgeon may operate a delivery device to deploy one or more prostheses through tendon 922 and bone 924 without requiring the surgeon to manipulate the position of portion 920 through an additional tool or means. This may simplify the implantation procedure.

Generally, the number of holding members used with a delivery device could vary in different embodiments. In some cases, a single holding member could be used. In other cases, two or more holding members could be used. In still other cases, three holding members could be used. In still other cases, four holding members could be used. In still other cases, five or more holding members could be used.

The alignment of two or more holding members could vary in different embodiments. Some embodiments could utilize holding members that are approximately evenly spaced around a distal end of detachable front delivery system 900. In other embodiments, the spacing or configuration of holding members could vary and could include asymmetric configurations or configurations with uneven spacing.

The geometry of each holding member could vary in different embodiments. In some embodiments, each holding member could have a substantially similar geometry. In other embodiments, the geometry of at least two holding members could be substantially different. For example, some embodiments could incorporate two or more holding members of different lengths (as measured from the distal end of a delivery device).

Some embodiments may include provisions for retracting one or more holding members. Some embodiments could include holding members that are attached to a moveable tube, cannula, or other similar component that is disposed within a detachable front delivery system. As one example, shown in FIG. 73, detachable front delivery system 1000 includes an outer cannula 1002 and an inner cannula 1004. Plurality of holding members 1006 may be attached to, and/or formed with, inner cannula 1004. This configuration may allow for holding members 1006 to be protected within movable outer cannula 1002, which is spring loaded via spring 1020. This may help prevent plurality of holding members from engaging tissue until the surgeon has located outer cannula 1002 at the desired location for implantation.

Whatever its ultimate use or features, a deployment device as discussed here (for example, deployment device 202 of FIG. 13) may be adapted for use in a medical environment. For example, some components of deployment device 202 could be detachable from their respective points of connection on base assembly 210 and/or front delivery assembly 212, so as to facilitate autoclaving or other sterilization procedures. In some embodiments, base assembly 210 itself may also be autoclavable or otherwise sterilizable. As previously mentioned, a front delivery assembly could be packaged sterile and/or disposable. In some embodiments, the entire deployment device could be packaged sterile and/or disposable.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

While various embodiments have been described, the description is intended to be exemplary, rather than limiting and it will be apparent to those of ordinary skill in the art that many more embodiments and implementations are possible that are within the scope of the embodiments. Accordingly, the embodiments are not to be restricted except in light of the attached claims and their equivalents. Also, various modifications and changes may be made within the scope of the attached claims.

What is claimed is:

1. A deployment device for tissue repair, comprising:
a first prosthesis;
a second prosthesis; and
a driving assembly comprising at least one of a driving pin and a driving tube, the at least one of the driving pin and the driving tube defining a driving axis, and the driving assembly being configured to provide a driving force approximately along the driving axis;
wherein the first prosthesis and the second prosthesis are positionable within the deployment device at a first configuration and a second configuration;
wherein the first prosthesis is approximately aligned with the driving assembly along the driving axis in the first configuration and wherein the second prosthesis is out of alignment with the driving assembly and the driving axis in the first configuration;
wherein the second prosthesis is approximately aligned with the driving assembly along the driving axis in the second configuration and wherein the first prosthesis is out of alignment with the driving assembly and the driving axis in the second configuration; and
wherein the first prosthesis and the second prosthesis each rotate around a central longitudinal axis that is generally parallel to the driving axis, in moving between the first configuration and the second configuration.

2. The deployment device according to claim 1, further comprising a third prosthesis;
wherein the third prosthesis is approximately aligned with the driving assembly along the driving axis in a third configuration; and
wherein the first prosthesis and the second prosthesis are out of alignment with the driving assembly and the driving axis in the third configuration.

3. The deployment device according to claim 1, wherein the deployment device includes a rotation lever that rotates the first prosthesis and the second prosthesis around the central longitudinal axis within the deployment device.

4. The deployment device according to claim 1, wherein the first prosthesis is associated with a first driven assembly comprising at least one of a first driven pin and a first driven tube,
wherein the second prosthesis is associated with a second driven assembly comprising at least one of a second driven pin and a second driven tube,
wherein, in the first configuration, the at least one of a first driven pin and a first driven tube is approximately aligned along the driving axis with the at least one of a driving pin and a driving tube of the driving assembly, and the at least one of a second driven pin and a second driven tube is out of alignment with the at least one of a driving pin and a driving tube of the driving assembly, and
wherein, in the second configuration, the at least one of a second driven pin and a second driven tube is approximately aligned along the driving axis with the at least one of a driving pin and a driving tube of the driving assembly, and the at least one of a first driven pin and a first driven tube is out of alignment with the at least one of a driving pin and a driving tube of the driving assembly.

5. The deployment device according to claim 4, wherein the first driven assembly comprises the first driven pin and the first driven tube,
wherein the first driven pin is disposed within a hollow longitudinal cavity defined by the first driven tube,
wherein the deployment device includes a retracting member that engages the first driven tube of the first driven assembly and retracts the first driven tube in a direction opposite to the driving force.

6. The deployment device according to claim 1, wherein:
the first prosthesis and the second prosthesis are associated with a front delivery assembly;
the driving assembly is associated with a base assembly; and
the front delivery assembly is detachable from the base assembly.

7. The deployment device according to claim 6, wherein the driving assembly comprises the driving pin and the driving tube, and
wherein the front delivery assembly further includes at least one driven assembly comprising a driven tube and a driven pin that respectively engage the driving tube and the driving pin of the driving assembly.

8. The deployment device according to claim 7, wherein the driven tube and the driving tube comprise shaped end portions that correspond to one another and wherein one end portion is convex and the other end portion is concave.

9. The deployment device according to claim 8, wherein the driven pin and the driving pin comprise shaped end portions that correspond to one another and wherein one end portion is convex and the other end portion is concave.

10. The deployment device according to claim 1, wherein the movement of the driving assembly is restricted when the first prosthesis and the second prosthesis are both out of alignment with the driving assembly.

11. The deployment device according to claim 1, wherein the deployment device includes at least one visual indicator for indicating to a user the depth to which a prosthesis has been implanted into a tissue.

12. A deployment device for tissue repair, comprising:
a first prosthesis;
a second prosthesis; and
a driving assembly comprising at least one of a driving pin and a driving tube, the at least one of the driving pin and the driving tube defining a driving axis, and the driving assembly being configured to provide a driving force approximately along the driving axis,
wherein the first prosthesis and the second prosthesis are positionable within the deployment device at a first configuration and a second configuration,
wherein the first prosthesis is approximately aligned with the driving assembly along the driving axis in the first configuration and wherein the second prosthesis is out of alignment with the driving assembly and the driving axis in the first configuration,
wherein the second prosthesis is approximately aligned with the driving assembly along the driving axis in the second configuration and wherein the first prosthesis is out of alignment with the driving assembly and the driving axis in the second configuration
wherein the first prosthesis is associated with a first driven assembly comprising at least one of a first driven pin and a first driven tube,
wherein the second prosthesis is associated with a second driven assembly comprising at least one of a second driven pin and a second driven tube, wherein, in the first configuration, the at least one of a first driven pin and a first driven tube is approximately aligned along the driving axis with the at least one of a driving pin and a driving tube of the driving assembly, and the at least one of a second driven pin and a second driven tube is out of alignment with the at least one of a driving pin and a driving tube of the driving assembly, wherein, in the second configuration, the at least one of a second driven pin and a second driven tube is approximately aligned along the driving axis with the at least one of a driving pin and a driving tube of the driving assembly, and the at least one of a first driven pin and a first driven tube is out of alignment with the at least one of a driving pin and a driving tube of the driving assembly, and wherein the first driven assembly and the second driven assembly rotate simultaneously around a central longitudinal axis that is generally parallel to the driving axis, in moving between the first configuration and the second configuration.

13. The deployment device according to claim 12, wherein a rotational position of the first driven assembly is locked once the first prosthesis has been at least partially deployed.

14. The deployment device according to claim 12, wherein the driving assembly comprises the driving pin and the driving tube,
wherein the deployment device further includes a locking member having an inner edge disposed around the driving tube of the driving assembly,
wherein the locking member rotates with the first driven assembly and the second driven assembly, and
wherein, when the first driven assembly and the second driven assembly are between the first configuration and the second configuration, the inner edge of the locking member engages an outer surface of the driving tube and prevents movement of the driving tube along the driving axis.

15. The deployment device according to claim 14, wherein the outer surface of the driving tube defines a groove extending substantially lateral to the driving axis, and wherein the inner edge of the locking member slides into the groove between the first configuration and the second configuration.

16. A deployment device for tissue repair, comprising:
a first prosthesis;
a second prosthesis; and
a driving assembly comprising at least one of a driving pin and a driving tube, the at least one of the driving pin and the driving tube defining a driving axis, and the driving assembly being configured to provide a driving force approximately along the driving axis,
wherein the first prosthesis and the second prosthesis are positionable within the deployment device at a first configuration and a second configuration,
wherein the first prosthesis is approximately aligned with the driving assembly along the driving axis in the first configuration and wherein the second prosthesis is out of alignment with the driving assembly and the driving axis in the first configuration,
wherein the second prosthesis is approximately aligned with the driving assembly along the driving axis in the second configuration and wherein the first prosthesis is out of alignment with the driving assembly and the driving axis in the second configuration,
wherein the first prosthesis and the second prosthesis are associated with a front delivery assembly,
wherein the driving assembly is associated with a base assembly,
wherein the front delivery assembly is detachable from the base assembly,
wherein the driving assembly comprises the driving pin and the driving tube,
wherein the front delivery assembly further includes at least one driven assembly comprising a driven tube and a driven pin that respectively engage the driving tube and the driving pin of the driving assembly,
wherein the front delivery assembly includes a cannula and a guide member for retaining and aligning the at least one driven assembly,
wherein the at least one driven assembly and the guide member are disposed inside the cannula, and
wherein the guide member is disposed around an outer surface of the driven tube of the at least one driven assembly.

17. The deployment device according to claim 16, wherein the front delivery assembly further comprises an o-ring disposed between the guide member and the outer surface of the driven tube, and
wherein the o-ring prevents fluid communication between portions of the deployment device disposed forward of the guide member and portions of the deployment device disposed rearward of the guide member.

18. A method of operating a deployment device for tissue repair, comprising:
attaching a front delivery assembly including at least two prostheses to a base assembly to form the deployment device, wherein the deployment device comprises
a first prosthesis,
a second prosthesis, and
a driving assembly comprising at least one of a driving pin and a driving tube, the at least one of the driving pin and the driving tube defining a driving axis, and the driving assembly being configured to provide a driving force approximately along the driving axis,
wherein the first prosthesis and the second prosthesis are positionable within the deployment device at a first configuration and a second configuration,
wherein the first prosthesis is approximately aligned with the driving assembly along the driving axis in the first configuration and wherein the second prosthesis is out of alignment with the driving assembly and the driving axis in the first configuration,
wherein the second prosthesis is approximately aligned with the driving assembly along the driving axis in the second configuration and wherein the first prosthesis is out of alignment with the driving assembly and the driving axis in the second configuration, and
wherein the first prosthesis and the second prosthesis each rotate around a central longitudinal axis that is generally parallel to the driving axis, in moving between the first configuration and the second configuration;
aligning the front delivery assembly with a desired region of tissue;
implanting the first prosthesis using the deployment device in the first configuration;
implanting the second prosthesis using the deployment device in the second configuration; and
detaching the front delivery assembly from the base assembly.

19. The method according to claim 18, wherein attaching the front delivery assembly includes depressing at least one lever on the front delivery assembly.

20. The method according to claim 18, wherein the front delivery assembly includes at least three prostheses.

21. The method according to claim 20, wherein the front delivery assembly includes at least three driven assemblies associated with the at least three prostheses.

22. The method according to claim 18, wherein aligning the front delivery assembly includes using at least one holding member that is disposed on a forward end of the front delivery assembly.

23. The method according to claim 22, further comprising holding a tissue in place using the holding member.

24. The method according to claim 18, wherein detaching the front delivery assembly is followed by attaching another front delivery assembly to the base assembly.

25. A deployment device for tissue repair, comprising:
a first prosthesis;
a second prosthesis; and
a driving assembly comprising at least one of a driving pin and a driving tube, the at least one of the driving pin and the driving tube defining a driving axis, and the driving assembly being configured to provide a driving force approximately along the driving axis,
wherein the first prosthesis and the second prosthesis are positionable within the deployment device at a first configuration and a second configuration,
wherein the first prosthesis is approximately aligned with the driving assembly along the driving axis in the first configuration and wherein the second prosthesis is out of alignment with the driving assembly and the driving axis in the first configuration,
wherein the second prosthesis is approximately aligned with the driving assembly along the driving axis in the second configuration and wherein the first prosthesis is out of alignment with the driving assembly and the driving axis in the second configuration,
wherein the first prosthesis is associated with a first driven assembly comprising at least one of a first driven pin and a first driven tube,
wherein the second prosthesis is associated with a second driven assembly comprising at least one of a second driven pin and a second driven tube,
wherein, in the first configuration, the at least one of a first driven pin and a first driven tube is approximately aligned along the driving axis with the at least one of a driving pin and a driving tube of the driving assembly, and the at least one of a second driven pin and a second driven tube is out of alignment with the at least one of a driving pin and a driving tube of the driving assembly,
wherein, in the second configuration, the at least one of a second driven pin and a second driven tube is approximately aligned along the driving axis with the at least one of a driving pin and a driving tube of the driving assembly, and the at least one of a first driven pin and a first driven tube is out of alignment with the at least one of a driving pin and a driving tube of the driving assembly,
wherein the driving assembly comprises the driving pin and the driving tube,
wherein the first driven assembly comprises the first driven pin and the first driven tube,
wherein the second driven assembly comprises the second driven pin and the second driven tube,
wherein the driving pin is disposed in a hollow longitudinal cavity of the driving tube and moves axially within the hollow longitudinal cavity of the driving tube relative to the driving tube,
wherein the first driven pin is disposed in a hollow longitudinal cavity of the first driven tube and moves axially within the hollow longitudinal cavity of the first driven tube relative to the first driven tube, and
wherein the second driven pin is disposed in a hollow longitudinal cavity of the second driven tube and moves axially within the hollow longitudinal cavity of the second driven tube relative to the second driven tube.

26. The deployment device according to claim 25, wherein, in the first configuration, the driving pin and the driving tube are axially aligned with and separate from the first driven pin and the first driven tube.

27. A deployment device for tissue repair, comprising:
a driving assembly comprising a driving pin and a driving tube,
wherein the driving pin is disposed inside the driving tube and moves relative to the driving tube along a driving axis;
a first driven assembly comprising a first driven pin and a first driven tube,
wherein the first driven pin is disposed inside the first driven tube and moves relative to the first driven tube;
a first prosthesis disposed on the first driven assembly at a forward end portion of the first driven assembly;
a second driven assembly comprising a second driven pin and a second driven tube,
wherein the second driven pin is disposed inside the second driven tube and moves relative to the second driven tube; and
a second prosthesis disposed on the second driven assembly at a forward end portion of the second driven assembly,
wherein the first driven assembly and the second driven assembly rotate around a central longitudinal axis that is generally parallel to the driving axis,
wherein in a first configuration, the first driven pin and the first driven tube are approximately aligned along the driving axis with the first driving pin and the first driving tube, respectively, and the second driven pin and the second driven tube are out of alignment with the first driving pin and the first driving tube, and
wherein in the second configuration, the second driven pin and the second driven tube are approximately aligned along the driving axis with the first driving pin and the first driving tube, respectively, and the first driven pin and the first driven tube are out of alignment with the first driving pin and the first driving tube.

28. The deployment device according to claim 27, wherein the first prosthesis defines a longitudinal cavity and a rearward portion,
wherein the first driven pin extends forward of the rearward portion of the first prosthesis and inside the longitudinal cavity of the first prosthesis, and the first driven tube contacts the rearward portion of the first prosthesis, and
wherein in the first configuration, the driving tube and the first driven tube move in a forward direction along the driving axis a distance greater than the driving pin and the first driven pin move in the forward direction along the driving axis, to implant the first prosthesis.

* * * * *